(12) United States Patent
Taira et al.

(10) Patent No.: US 12,030,790 B2
(45) Date of Patent: Jul. 9, 2024

(54) METHOD FOR REMOVING FLUORINE-CONTAINING COMPOUND FROM WASTE WATER

(71) Applicant: DAIKIN INDUSTRIES, LTD., Osaka (JP)

(72) Inventors: Takahiro Taira, Osaka (JP); Tadao Hayashi, Osaka (JP); Chiaki Okui, Osaka (JP); Ryou Hatayama, Osaka (JP); Michinobu Koizumi, Osaka (JP); Taketo Kato, Osaka (JP); Yuuji Tanaka, Osaka (JP); Hirotoshi Yoshida, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 540 days.

(21) Appl. No.: 17/280,972

(22) PCT Filed: Oct. 3, 2019

(86) PCT No.: PCT/JP2019/039190
§ 371 (c)(1),
(2) Date: Mar. 29, 2021

(87) PCT Pub. No.: WO2020/071505
PCT Pub. Date: Apr. 9, 2020

(65) Prior Publication Data
US 2021/0363031 A1   Nov. 25, 2021

(30) Foreign Application Priority Data
Oct. 3, 2018 (JP) .................. 2018-188701

(51) Int. Cl.
| | |
|---|---|
| *B01J 41/04* | (2017.01) |
| *B01J 20/20* | (2006.01) |
| *B01J 20/28* | (2006.01) |
| *B01J 41/12* | (2017.01) |
| *C02F 1/28* | (2023.01) |
| *C02F 1/42* | (2023.01) |

(Continued)

(52) U.S. Cl.
CPC .............. *C02F 1/283* (2013.01); *B01J 20/20* (2013.01); *B01J 20/28064* (2013.01); *B01J 20/2808* (2013.01); *B01J 20/28083* (2013.01); *B01J 20/28085* (2013.01); *B01J 41/04* (2013.01); *B01J 41/12* (2013.01); *C02F 1/42* (2013.01); *C08F 14/26* (2013.01); *C02F 2001/422* (2013.01); *C02F 2101/36* (2013.01); *C02F 2103/38* (2013.01)

(58) Field of Classification Search
CPC .......... C02F 1/283; C02F 101/34; C02F 1/28; C02F 1/42; C02F 1/66; C02F 2001/422; C02F 2101/36; C02F 2101/363; C02F 2103/38; C02F 2103/36; B01J 20/20; B01J 20/28064; B01J 20/2808; B01J 20/28078; B01J 20/28083; B01J 20/22; B01J 20/34; B01J 41/04; B01J 41/12; C08F 14/26; C08F 14/18; C08F 2/16; C08F 114/18; C11B 3/00; C09D 127/18; C08B 37/16; C07C 51/42; C07C 59/135
See application file for complete search history.

(56) References Cited

U.S. PATENT DOCUMENTS

| | | | |
|---|---|---|---|
| 8,563,670 B2 | 10/2013 | Brothers et al. | |
| 9,074,025 B2 | 7/2015 | Brothers et al. | |

(Continued)

FOREIGN PATENT DOCUMENTS

| | | | | |
|---|---|---|---|---|
| EP | 1323677 A1 | * | 7/2003 | .............. B01J 41/04 |
| EP | 2 929 935 A1 | | 10/2015 | |

(Continued)

OTHER PUBLICATIONS

International Preliminary Report on Patentability dated Mar. 23, 2021 with Written Opinion in International Application No. PCT/JP2019/039190, 8 pages.

(Continued)

*Primary Examiner* — Bradley R Spies
(74) *Attorney, Agent, or Firm* — Sughrue Mion, PLLC

(57) ABSTRACT

A method for removing a fluorine-containing compound from discharge water, which includes bringing discharge water containing two or more fluorine-containing compounds represented by the following general formula (1) or (2) into contact with an adsorbent so as to adsorb the two or more fluorine-containing compounds:

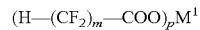

General Formula (1):

wherein m is 3 to 19, $M^1$ is H, a metal atom, $NR^b{}_4$, where $R^b$ is the same or different and is H or an organic group having 1 to 10 carbon atoms, imidazolium optionally having a substituent, pyridinium optionally having a substituent, or phosphonium optionally having a substituent; and p is 1 or 2;

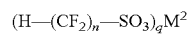

General Formula (2):

wherein n is 4 to 20; $M^2$ is H, a metal atom, $NR^b{}_4$, where $R^b$ is the same as above, imidazolium optionally having a substituent, pyridinium optionally having a substituent, or phosphonium optionally having a substituent; and q is 1 or 2.

10 Claims, No Drawings

(51) Int. Cl.
    *C02F 101/36*   (2006.01)
    *C02F 103/38*   (2006.01)
    *C08F 14/26*    (2006.01)

(56) References Cited

U.S. PATENT DOCUMENTS

| | | |
|---|---|---|
| 9,255,164 B2 | 2/2016 | Brothers et al. |
| 2004/0010156 A1 | 1/2004 | Kondo et al. |
| 2005/0173347 A1 | 8/2005 | Hintzer et al. |
| 2007/0142590 A1 * | 6/2007 | Rasmussen .............. B01J 41/14 526/310 |
| 2011/0021728 A1 | 1/2011 | Higuchi et al. |
| 2011/0040054 A1 | 2/2011 | Higuchi et al. |
| 2012/0029232 A1 | 2/2012 | Kuramitsu et al. |
| 2013/0334140 A1 | 12/2013 | Podesta et al. |
| 2021/0363031 A1 | 11/2021 | Taira et al. |

FOREIGN PATENT DOCUMENTS

| | | |
|---|---|---|
| JP | 2002-059160 A | 2/2002 |
| JP | 2006-181416 A | 7/2006 |
| JP | 2009-235070 A | 10/2009 |
| JP | 2013-180259 A | 9/2013 |
| JP | 2014-039912 A | 3/2014 |
| JP | 7216304 B2 | 2/2023 |
| WO | 2009/128432 A1 | 10/2009 |
| WO | 2009/142080 A1 | 11/2009 |
| WO | 2010/113720 A1 | 10/2010 |
| WO | WO-2014136692 A1 * | 9/2014 ........... B01D 15/203 |

OTHER PUBLICATIONS

Extended European Search Report dated May 25, 2022 from the European Patent Office in EP Application No. 19869375.6, 7 pages.
International Search Report of PCT/JP2019/039190 dated Dec. 3, 2019 [PCT/ISA/210], 5 pages.

* cited by examiner

METHOD FOR REMOVING FLUORINE-CONTAINING COMPOUND FROM WASTE WATER

CROSS REFERENCE TO RELATED APPLICATIONS

This application is a National Stage of International Application No. PCT/JP2019/039190 filed on Oct. 3, 2019, claiming priority based on Japanese Patent Application No. 2018-188701 filed on Oct. 3, 2018.

TECHNICAL FIELD

The present disclosure relates to a method for removing a fluorine-containing compound from discharge water.

BACKGROUND ART

Fluorinated anion surfactants have been used in production of fluorine-containing polymers by emulsion polymerization. Recently, it has been proposed to use hydrocarbon surfactants instead of the fluorinated anion surfactants (see, for example, Patent Documents 1 to 3).

RELATED ART

Patent Documents

Patent Document 1: U.S. Pat. No. 9,255,164
Patent Document 2: U.S. Pat. No. 8,563,670
Patent Document 3: U.S. Pat. No. 9,074,025

SUMMARY OF THE INVENTION

Problem to be Solved by the Invention

The present disclosure provides a method for removing a fluorine-containing compound from discharge water, which can efficiently remove two or more specific fluorine-containing compounds from discharge water.

Means for Solving the Problem

The present disclosure provides a method for removing a fluorine-containing compound from discharge water (hereinafter, may be simply referred to as "the removal method of the present disclosure") including bringing discharge water containing two or more fluorine-containing compounds represented by the following general formula (1) or (2) into contact with an adsorbent to allow the adsorbent to adsorb the two or more fluorine-containing compounds:

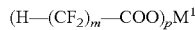  General Formula (1):

wherein m is 3 to 19, $M^1$ is H, a metal atom, $NR^b{}_4$, where $R^b$ is the same or different and is H or an organic group having 1 to 10 carbon atoms, imidazolium optionally having a substituent, pyridinium optionally having a substituent, or phosphonium optionally having a substituent; and p is 1 or 2,

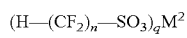  General Formula (2):

wherein n is 4 to 20; $M^2$ is H, a metal atom, $NR^b{}_4$, where $R^b$ is the same as above, imidazolium optionally having a substituent, pyridinium optionally having a substituent, or phosphonium optionally having a substituent; and q is 1 or 2.

The discharge water preferably includes discharge water obtained in a process for producing a fluorine-containing polymer using a hydrocarbon surfactant.

The discharge water preferably further contains a hydrocarbon surfactant.

The hydrocarbon surfactant is preferably a carboxylic acid-type hydrocarbon surfactant.

The adsorbent is preferably at least one selected from the group consisting of an ion exchange resin, activated carbon, a synthetic adsorbent, silica gel, clay, and zeolite.

The adsorbent is an ion exchange resin or a synthetic adsorbent and preferably has a pore diameter of 1 to 5,000 Å.

The adsorbent is activated carbon and preferably has a specific surface area of 500 m²/g or more.

The temperature in the adsorption is preferably 0 to 50° C.

The removal ratio of the fluorine-containing compound in the adsorption is preferably 40% or more.

The method for removing a fluorine-containing compound from discharge water of the present disclosure further preferably includes a pretreatment for removing a solid component from the discharge water before the adsorption.

The fluorine-containing compound preferably includes at least a fluorine-containing compound having m of 7 or more in the general formula (1) or a fluorine-containing compound having n of 8 or more in the general formula (2).

Effects of Invention

Since the removal method of the present disclosure has the above configuration, it is possible to efficiently remove two or more specific fluorine-containing compounds from discharge water.

DESCRIPTION OF EMBODIMENTS

The term "organic group" as used herein, unless otherwise specified, means a group containing one or more carbon atoms or a group obtainable by removing one hydrogen atom from an organic compound.

Examples of the "organic group" include:
an alkyl group optionally having one or more substituents,
an alkenyl group optionally having one or more substituents,
an alkynyl group optionally having one or more substituents,
a cycloalkyl group optionally having one or more substituents,
a cycloalkenyl group optionally having one or more substituents,
a cycloalkadienyl group optionally having one or more substituents,
an aryl group optionally having one or more substituents,
an aralkyl group optionally having one or more substituents,
a non-aromatic heterocyclic group optionally having one or more substituents,
a heteroaryl group optionally having one or more substituents,
a cyano group,
a formyl group,
RaO—,
RaCO—,
RaSO$_2$—,
RaCOO—, RaNRaCO—,
RaCONRa—,
RaOCO—, and
RaOSO$_2$—,
wherein each Ra is independently
an alkyl group optionally having one or more substituents,
an alkenyl group optionally having one or more substituents,
an alkynyl group optionally having one or more substituents,
a cycloalkyl group optionally having one or more substituents,
a cycloalkenyl group optionally having one or more substituents,
a cycloalkadienyl group optionally having one or more substituents,
an aryl group optionally having one or more substituents,
an aralkyl group optionally having one or more substituents,
a non-aromatic heterocyclic group optionally having one or more substituents, or
a heteroaryl group optionally having one or more substituents.

The organic group is preferably an alkyl group optionally having one or more substituents.

The term "substituent" as used herein, unless otherwise specified, means a group capable of replacing another atom or group. Examples of the "substituent" include an aliphatic group, an aromatic group, a heterocyclic group, an acyl group, an acyloxy group, an acylamino group, an aliphatic oxy group, an aromatic oxy group, a heterocyclic oxy group, an aliphatic oxycarbonyl group, an aromatic oxycarbonyl group, a heterocyclic oxycarbonyl group, a carbamoyl group, an aliphatic sulfonyl group, an aromatic sulfonyl group, a heterocyclic sulfonyl group, an aliphatic sulfonyloxy group, an aromatic sulfonyloxy group, a heterocyclic sulfonyloxy group, a sulfamoyl group, an aliphatic sulfonamide group, an aromatic sulfonamide group, a heterocyclic sulfonamide group, an amino group, an aliphatic amino group, an aromatic amino group, a heterocyclic amino group, an aliphatic oxycarbonylamino group, an aromatic oxycarbonylamino group, a heterocyclic oxycarbonylamino group, an aliphatic sulfinyl group, an aromatic sulfinyl group, an aliphatic thio group, an aromatic thio group, a hydroxy group, a cyano group, a sulfo group, a carboxy group, an aliphatic oxyamino group, an aromatic oxy amino group, a carbamoylamino group, a sulfamoylamino group, a halogen atom, a sulfamoylcarbamoyl group, a carbamoyl sulfamoyl group, a dialiphatic oxyphosphinyl group, or a diaromatic oxyphosphinyl group.

The aliphatic group may be saturated or unsaturated, and may have a hydroxy group, an aliphatic oxy group, a carbamoyl group, an aliphatic oxycarbonyl group, an aliphatic thio group, an amino group, an aliphatic amino group, an acylamino group, a carbamoylamino group, or the like. Examples of the aliphatic group include alkyl groups having 1 to 8, preferably 1 to 4 carbon atoms in total, such as a methyl group, an ethyl group, a vinyl group, a cyclohexyl group, and a carbamoylmethyl group.

The aromatic group may have, for example, a nitro group, a halogen atom, an aliphatic oxy group, a carbamoyl group, an aliphatic oxycarbonyl group, an aliphatic thio group, an amino group, an aliphatic amino group, an acylamino group, a carbamoylamino group, or the like. Examples of the aromatic group include aryl groups having 6 to 12 carbon atoms, preferably 6 to 10 carbon atoms in total, such as a phenyl group, a 4-nitrophenyl group, a 4-acetylaminophenyl group, and a 4-methanesulfonylphenyl group.

The heterocyclic group may have a halogen atom, a hydroxy group, an aliphatic oxy group, a carbamoyl group, an aliphatic oxycarbonyl group, an aliphatic thio group, an amino group, an aliphatic amino group, an acylamino group, a carbamoylamino group, or the like. Examples of the heterocyclic group include 5- or 6-membered heterocyclic groups having 2 to 12, preferably 2 to 10 carbon atoms in total, such as a 2-tetrahydrofuryl group and a 2-pyrimidyl group.

The acyl group may have an aliphatic carbonyl group, an arylcarbonyl group, a heterocyclic carbonyl group, a hydroxy group, a halogen atom, an aromatic group, an aliphatic oxy group, a carbamoyl group, an aliphatic oxycarbonyl group, an aliphatic thio group, an amino group, an aliphatic amino group, an acylamino group, a carbamoylamino group, or the like. Examples of the acyl group include acyl groups having 2 to 8, preferably 2 to 4 carbon atoms in total, such as an acetyl group, a propanoyl group, a benzoyl group, and a 3-pyridinecarbonyl group.

The acylamino group may have an aliphatic group, an aromatic group, a heterocyclic group, or the like, and may have, for example, an acetylamino group, a benzoylamino group, a 2-pyridinecarbonylamino group, a propanoylamino group, or the like. Examples of the acylamino group include acylamino groups having 2 to 12, preferably 2 to 8 carbon atoms in total, and alkylcarbonylamino groups having 2 to 8 carbon atoms in total, such as an acetylamino group, a benzoylamino group, a 2-pyridinecarbonylamino group, and a propanoylamino group.

The aliphatic oxycarbonyl group may be saturated or unsaturated, and may have a hydroxy group, an aliphatic oxy group, a carbamoyl group, an aliphatic oxycarbonyl group, an aliphatic thio group, an amino group, an aliphatic amino group, an acylamino group, a carbamoylamino group, or the like. Examples of the aliphatic oxycarbonyl group include alkoxycarbonyl groups having 2 to 8, preferably 2 to 4 carbon atoms in total, such as a methoxycarbonyl group, an ethoxycarbonyl group, and a (t)-butoxycarbonyl group.

The carbamoyl group may have an aliphatic group, an aromatic group, a heterocyclic group, or the like. Examples of the carbamoyl group include an unsubstituted carbamoyl group and alkylcarbamoyl groups having 2 to 9 carbon atoms in total, preferably an unsubstituted carbamoyl group and alkylcarbamoyl groups having 2 to 5 carbon atoms in total, such as a N-methylcarbamoyl group, a N,N-dimethylcarbamoyl group, and a N-phenylcarbamoyl group.

The aliphatic sulfonyl group may be saturated or unsaturated, and may have a hydroxy group, an aromatic group, an aliphatic oxy group, a carbamoyl group, an aliphatic oxycarbonyl group, an aliphatic thio group, an amino group, an aliphatic amino group, an acylamino group, a carbamoylamino group, or the like. Examples of the aliphatic sulfonyl group include alkylsulfonyl groups having 1 to 6 carbon atoms in total, preferably 1 to 4 carbon atoms in total, such as a methanesulfonyl group.

The aromatic sulfonyl group may have a hydroxy group, an aliphatic group, an aliphatic oxy group, a carbamoyl group, an aliphatic oxycarbonyl group, an aliphatic thio group, an amino group, an aliphatic amino group, an acylamino group, a carbamoylamino group, or the like. Examples of the aromatic sulfonyl group include arylsulfonyl groups having 6 to 10 carbon atoms in total, such as a benzenesulfonyl group.

The amino group may have an aliphatic group, an aromatic group, a heterocyclic group, or the like.

The acylamino group may have, for example, an acetylamino group, a benzoylamino group, a 2-pyridinecarbonylamino group, a propanoylamino group, or the like. Examples of the acylamino group include acylamino groups having 2 to 12 carbon atoms in total, preferably 2 to 8 carbon atoms in total, and more preferably alkylcarbonylamino groups having 2 to 8 carbon atoms in total, such as an acetylamino group, a benzoylamino group, a 2-pyridinecarbonylamino group, and a propanoylamino group.

The aliphatic sulfonamide group, aromatic sulfonamide group, and heterocyclic sulfonamide group may be, for example, a methanesulfonamide group, a benzenesulfonamide group, a 2-pyridinesulfonamide group, respectively.

The sulfamoyl group may have an aliphatic group, an aromatic group, a heterocyclic group, or the like. Examples of the sulfamoyl group include a sulfamoyl group, alkylsulfamoyl groups having 1 to 9 carbon atoms in total, dialkylsulfamoyl groups having 2 to 10 carbon atoms in total, arylsulfamoyl groups having 7 to 13 carbon atoms in total, and heterocyclic sulfamoyl groups having 2 to 12 carbon atoms in total, more preferably a sulfamoyl group, alkylsulfamoyl groups having 1 to 7 carbon atoms in total, dialkylsulfamoyl groups having 3 to 6 carbon atoms in total, arylsulfamoyl groups having 6 to 11 carbon atoms in total, and heterocyclic sulfamoyl groups having 2 to 10 carbon atoms in total, such as a sulfamoyl group, a methylsulfamoyl group, a N,N-dimethylsulfamoyl group, a phenylsulfamoyl group, and a 4-pyridinesulfamoyl group.

The aliphatic oxy group may be saturated or unsaturated, and may have a methoxy group, an ethoxy group, an i-propyloxy group, a cyclohexyloxy group, a methoxyethoxy group, or the like. Examples of the aliphatic oxy group include alkoxy groups having 1 to 8, preferably 1 to 6 carbon atoms in total, such as a methoxy group, an ethoxy group, an i-propyloxy group, a cyclohexyloxy group, and a methoxyethoxy group.

The aromatic amino group and the heterocyclic amino group each may have an aliphatic group, an aliphatic oxy group, a halogen atom, a carbamoyl group, a heterocyclic group ring-fused with the aryl group, and an aliphatic oxycarbonyl group, preferably an aliphatic group having 1 to 4 carbon atoms in total, an aliphatic oxy group having 1 to 4 carbon atoms in total, a halogen atom, a carbamoyl group having 1 to 4 carbon atoms in total, a nitro group, or an aliphatic oxycarbonyl group having 2 to 4 carbon atoms in total.

The aliphatic thio group may be saturated or unsaturated, and examples thereof include alkylthio groups having 1 to 8 carbon atoms in total, more preferably 1 to 6 carbon atoms in total, such as a methylthio group, an ethylthio group, a carbamoylmethylthio group, and a t-butylthio group.

The carbamoylamino group may have an aliphatic group, an aryl group, a heterocyclic group or the like. Examples of the carbamoylamino group include a carbamoylamino group, alkylcarbamoylamino groups having 2 to 9 carbon atoms in total, dialkylcarbamoylamino groups having 3 to 10 carbon atoms in total, arylcarbamoylamino groups having 7 to 13 carbon atoms in total, and heterocyclic carbamoylamino groups having 3 to 12 carbon atoms in total, preferably a carbamoylamino group, alkylcarbamoylamino groups having 2 to 7 carbon atoms in total, dialkylcarbamoylamino groups having 3 to 6 carbon atoms in total, arylcarbamoylamino groups having 7 to 11 carbon atoms in total, and heterocyclic carbamoylamino groups having 3 to 10 carbon atoms in total, such as a carbamoylamino group, a methylcarbamoylamino group, a N,N-dimethylcarbamoylamino group, a phenylcarbamoylamino group, and a 4-pyridinecarbamoylamino group.

Hereinafter, specific embodiments of the present disclosure will be described in detail, but the present disclosure is not limited to the following embodiments.

In the production of fluorine-containing polymers using conventional hydrocarbon surfactants, no studies have been conducted focusing on discharge water. It has been found that when a fluorine-containing polymer is produced by polymerization using a hydrocarbon surfactant, the discharge water generated by the process for producing a fluorine-containing polymer contains two or more fluorine-containing compounds represented by the general formula (1) or (2). As a result of diligent studies by the present disclosers and the like, it has been found that two or more kinds of the fluorine-containing compounds can be efficiently removed by a method including the adsorption step, thereby completing the removal method of the present disclosure.

The removal method of the present disclosure includes an adsorption step of bringing discharge water containing two or more fluorine-containing compounds represented by the following general formula (1) or (2) into contact with an adsorbent to allow the adsorbent to adsorb the two or more fluorine-containing compounds:

$$(H-(CF_2)_m-COO)_p M^1 \quad \text{General Formula (1):}$$

wherein m is 3 to 19, $M^1$ is H, a metal atom, $NR^b_4$, where $R^b$ is the same or different and is H or an organic group having 1 to 10 carbon atoms, imidazolium optionally having a substituent, pyridinium optionally having a substituent, or phosphonium optionally having a substituent; and p is 1 or 2, $$(H-(CF_2)_n-SO_3)_q M^2 \quad \text{General Formula (2):}$$

wherein n is 4 to 20; $M^2$ is H, a metal atom, $NR^b_4$, where $R^b$ is the same as above, imidazolium optionally having a substituent, pyridinium optionally having a substituent, or phosphonium optionally having a substituent; and q is 1 or 2.

Examples of the metal atom include monovalent and divalent metal atoms, alkali metals (Group 1) or alkaline earth metals (Group 2), and specific examples thereof include Na, K, and Li.

As $R^b$, the four $R^b$s may be the same as or different from each other. $R^b$ is preferably H or an organic group having 1 to 10 carbon atoms, and more preferably H or an organic group having 1 to 4 carbon atoms. Further, an alkyl group having 1 to 10 carbon atoms is preferable, and an alkyl group having 1 to 4 carbon atoms is more preferable. The above provisions are applicable to all $R^b$ described below.

In the general formula (1), m may be 5 to 11.

In the general formula (2), n may be 6 to 12.

As used herein, "discharge water containing two or more fluorine-containing compounds represented by the general formula (1) or (2)" means that the discharge water may contain at least two fluorine-containing compounds encompassed in the general formula (1) or (2), for example, the discharge water may contain two or more fluorine-containing compounds represented by the general formula (1) and not contain the fluorine-containing compound represented by the general formula (2); may not contain the fluorine-containing compound represented by the general formula (1) and contain two or more fluorine-containing compounds represented by the general formula (2); or may contain one or more compounds represented by the general formula (1)

and contain one or more fluorine-containing compounds represented by the general formula (2).

The discharge water includes an embodiment which contains a fluorine-containing compound having m of 6 and a fluorine-containing compound having m of 12 in the general formula (1), an embodiment which contains a fluorine-containing compound having n of 6 and a fluorine-containing compound having n of 12 in the general formula (2), or the like. Further, the discharge water may contain three or more fluorine-containing compounds or four or more fluorine-containing compounds as long as the discharge water contains two or more fluorine-containing compounds, and may contain all fluorine-containing compounds encompassed in the general formula (1) or (2).

The fluorine-containing compound may contain fluorine-containing compounds having m of 3, 5, 7, 9, 11, 13, 15, 17, and 19 and not contain fluorine-containing compounds having m of 4, 6, 8, 10, 12, 14, 16, and 18, or may contain fluorine-containing compounds having m of 4, 6, 8, 10, 12, 14, 16, 18, and 20 and not contain fluorine-containing compounds having m of 3, 5, 7, 9, 11, 13, 15, 17, and 19, or may contain all fluorine-containing compounds having m of 3 to 19, among the fluorine-containing compounds encompassed in the general formula (1).

Further, the fluorine-containing compound may contain fluorine-containing compounds having n of 5, 7, 9, 11, 13, 15, 17, and 19 and not contain fluorine-containing compounds having n of 4, 6, 8, 10, 12, 14, 16, 18, and 20, or may contain fluorine-containing compounds having n of 4, 6, 8, 10, 12, 14, 16, 18, and 20 and not contain fluorine-containing compounds having n of 5, 7, 9, 11, 13, 15, 17, and 19, or may contain all fluorine-containing compounds having n of 4 to 20, among the fluorine-containing compounds encompassed in the general formula (2).

In the removal method of the present disclosure, the concentration of the fluorine-containing compound represented by the general formula (1) or (2) in the discharge water is not limited, and discharge water can be treated at any concentration. The total amount of the compounds represented by the general formula (1) or (2) in the discharge water to be treated is preferably 0.01 ppm or more, more preferably 0.1 ppm or more, and still more preferably 0.5 ppm or more based on the total amount of discharge water. The total amount is further preferably 1 ppm or more, still further preferably 5 ppm or more, and particularly preferably 10 ppm or more, based on the total amount of discharge water. When the concentration of the fluorine-containing compound represented by the general formula (1) or (2) in the discharge water is above a certain level as described above, the removal method of the present disclosure exhibits higher removal efficiency.

Further, in the discharge water to be treated, the total amount of the fluorine-containing compounds represented by the general formula (1) or (2) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the total amount of the fluorine-containing compounds in the discharge water is within the above range, the removal efficiency can be further improved.

The discharge water generated in the process for producing a fluorine-containing polymer described later may be used as it is, or the discharge water generated in the process for producing a fluorine-containing polymer may be diluted or concentrated so that the total amount of the fluorine-containing compound represented by the general formula (1) or (2) is within the above range.

As used herein, ppm means a value obtained in terms of mass unless otherwise specified.

The amount of at least one of the fluorine-containing compounds represented by the general formula (1) having m of 3, 4, 5, 6, 7, 8, 9, 10, 11, 12, 13, 14, 15, 16, 17, 18 or 19 is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water.

When the concentration of the fluorine-containing compound represented by the general formula (1) in the discharge water is above a certain level as described above, the removal method of the present disclosure exhibits higher removal efficiency.

Further, the amount of at least one of the fluorine-containing compounds represented by the general formula (1) having m of 3, 4, 5, 6, 7, 8, 9, 10, 11, 12, 13, 14, 15, 16, 17, 18 or 19 is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having m of 3 in the general formula (1) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water.

When the concentration of the fluorine-containing compound represented by the general formula (1) in the discharge water is above a certain level as described above, the removal method of the present disclosure exhibits higher removal efficiency.

Further, the amount of the fluorine-containing compound having m of 3 in the general formula (1) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having m of 4 in the general formula (1) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water.

When the concentration of the fluorine-containing compound represented by the general formula (1) in the discharge water is above a certain level as described above, the removal method of the present disclosure exhibits higher removal efficiency.

Further, the amount of the fluorine-containing compound having m of 4 in the general formula (1) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having m of 5 in the general formula (1) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water.

When the concentration of the fluorine-containing compound represented by the general formula (1) in the discharge water is above a certain level as described above, the removal method of the present disclosure exhibits higher removal efficiency.

Further, the amount of the fluorine-containing compound having m of 5 in the general formula (1) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having m of 6 in the general formula (1) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water.

When the concentration of the fluorine-containing compound represented by the general formula (1) in the discharge water is above a certain level as described above, the removal method of the present disclosure exhibits higher removal efficiency.

Further, the amount of the fluorine-containing compound having m of 6 in the general formula (1) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having m of 7 in the general formula (1) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water.

When the concentration of the fluorine-containing compound represented by the general formula (1) in the discharge water is above a certain level as described above, the removal method of the present disclosure exhibits higher removal efficiency.

Further, the amount of the fluorine-containing compound having m of 7 in the general formula (1) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having m of 8 in the general formula (1) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water.

When the concentration of the fluorine-containing compound represented by the general formula (1) in the discharge water is above a certain level as described above, the removal method of the present disclosure exhibits higher removal efficiency.

Further, the amount of the fluorine-containing compound having m of 8 in the general formula (1) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having m of 9 in the general formula (1) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water.

When the concentration of the fluorine-containing compound represented by the general formula (1) in the discharge water is above a certain level as described above, the removal method of the present disclosure exhibits higher removal efficiency.

Further, the amount of the fluorine-containing compound having m of 9 in the general formula (1) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having m of 10 in the general formula (1) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water.

When the concentration of the fluorine-containing compound represented by the general formula (1) in the discharge water is above a certain level as described above, the removal method of the present disclosure exhibits higher removal efficiency.

Further, the amount of the fluorine-containing compound having m of 10 in the general formula (1) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having m of 11 in the general formula (1) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water.

When the concentration of the fluorine-containing compound represented by the general formula (1) in the discharge water is above a certain level as described above, the removal method of the present disclosure exhibits higher removal efficiency.

Further, the amount of the fluorine-containing compound having m of 11 in the general formula (1) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having m of 12 in the general formula (1) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water.

When the concentration of the fluorine-containing compound represented by the general formula (1) in the discharge water is above a certain level as described above, the removal method of the present disclosure exhibits higher removal efficiency.

Further, the amount of the fluorine-containing compound having m of 12 in the general formula (1) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having m of 13 in the general formula (1) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water.

When the concentration of the fluorine-containing compound represented by the general formula (1) in the discharge water is above a certain level as described above, the removal method of the present disclosure exhibits higher removal efficiency.

Further, the amount of the fluorine-containing compound having m of 13 in the general formula (1) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having m of 14 in the general formula (1) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water.

When the concentration of the fluorine-containing compound represented by the general formula (1) in the discharge water is above a certain level as described above, the removal method of the present disclosure exhibits higher removal efficiency.

Further, the amount of the fluorine-containing compound having m of 14 in the general formula (1) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having m of 15 in the general formula (1) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water.

When the concentration of the fluorine-containing compound represented by the general formula (1) in the discharge water is above a certain level as described above, the removal method of the present disclosure exhibits higher removal efficiency.

Further, the amount of the fluorine-containing compound having m of 15 in the general formula (1) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having m of 16 in the general formula (1) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water.

When the concentration of the fluorine-containing compound represented by the general formula (1) in the discharge water is above a certain level as described above, the removal method of the present disclosure exhibits higher removal efficiency.

Further, the amount of the fluorine-containing compound having m of 16 in the general formula (1) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having m of 17 in the general formula (1) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water.

When the concentration of the fluorine-containing compound represented by the general formula (1) in the discharge water is above a certain level as described above, the removal method of the present disclosure exhibits higher removal efficiency.

Further, the amount of the fluorine-containing compound having m of 17 in the general formula (1) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having m of 18 in the general formula (1) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water.

When the concentration of the fluorine-containing compound represented by the general formula (1) in the discharge water is above a certain level as described above, the removal method of the present disclosure exhibits higher removal efficiency.

Further, the amount of the fluorine-containing compound having m of 18 in the general formula (1) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having m of 19 in the general formula (1) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water.

When the concentration of the fluorine-containing compound represented by the general formula (1) in the discharge water is above a certain level as described above, the removal method of the present disclosure exhibits higher removal efficiency.

Further, the amount of the fluorine-containing compound having m of 19 in the general formula (1) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of at least one of the fluorine-containing compounds represented by the general formula (2) having n of 4, 5, 6, 7, 8, 9, 10, 11, 12, 13, 14, 15, 16, 17, 18, 19 or 20 is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water. When the concentration of the fluorine-containing compound represented by the general formula (2) in the discharge water is above a certain level as described above, the removal method of the present disclosure exhibits higher removal efficiency.

Further, the amount of at least one of the fluorine-containing compounds represented by the general formula (2) having n of 4, 5, 6, 7, 8, 9, 10, 11, 12, 13, 14, 15, 16, 17, 18, 19 or 20 is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having n of 4 in the general formula (2) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water. When the concentration of the fluorine-containing compound represented by the general formula (2) in the discharge water is above a certain level as described above, the removal method of the present disclosure exhibits higher removal efficiency.

Further, the amount of the fluorine-containing compound having n of 4 in the general formula (2) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having n of 5 in the general formula (2) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water. When the concentration of the fluorine-containing compound represented by the general formula (2) in the discharge water is above a certain level as described above, the removal method of the present disclosure exhibits higher removal efficiency.

Further, the amount of the fluorine-containing compound having n of 5 in the general formula (2) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having n of 6 in the general formula (2) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water. When the concentration of the fluorine-containing compound represented by the general formula (2) in the discharge water is above a certain level as described above, the removal method of the present disclosure exhibits higher removal efficiency.

Further, the amount of the fluorine-containing compound having n of 6 in the general formula (2) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having n of 7 in the general formula (2) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water. When the concentration of the fluorine-containing compound represented by the general formula (2) in the discharge water is above a certain level as described above, the removal method of the present disclosure exhibits higher removal efficiency.

Further, the amount of the fluorine-containing compound having n of 7 in the general formula (2) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having n of 8 in the general formula (2) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water. When the concentration of the fluorine-containing compound represented by the general formula (2) in the discharge water is above a certain level as described above, the removal method of the present disclosure exhibits higher removal efficiency.

Further, the amount of the fluorine-containing compound having n of 8 in the general formula (2) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having n of 9 in the general formula (2) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water. When the concentration of the fluorine-containing compound represented by the general formula (2) in the discharge water is above a certain level as described above, the removal method of the present disclosure exhibits higher removal efficiency.

Further, the amount of the fluorine-containing compound having n of 9 in the general formula (2) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having n of 10 in the general formula (2) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water. When the concentration of the fluorine-containing compound represented by the general formula (2) in the discharge water is above a certain level as described above, the removal method of the present disclosure exhibits higher removal efficiency.

Further, the amount of the fluorine-containing compound having n of 10 in the general formula (2) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having n of 11 in the general formula (2) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water. When the concentration of the fluorine-containing compound represented by the general formula (2) in the discharge water is above a certain level as described above, the removal method of the present disclosure exhibits higher removal efficiency.

Further, the amount of the fluorine-containing compound having n of 11 in the general formula (2) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having n of 12 in the general formula (2) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water. When the concentration of the fluorine-containing compound represented by the general formula (2) in the discharge water is above a certain level as described above, the removal method of the present disclosure exhibits higher removal efficiency.

Further, the amount of the fluorine-containing compound having n of 12 in the general formula (2) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having n of 13 in the general formula (2) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water. When the concentration of the fluorine-containing compound represented by the general formula (2) in the discharge water is above a certain level as described above, the removal method of the present disclosure exhibits higher removal efficiency.

Further, the amount of the fluorine-containing compound having n of 13 in the general formula (2) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having n of 14 in the general formula (2) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water. When the concentration of the fluorine-containing compound represented by the general formula (2) in the discharge water is above a certain level as described above, the removal method of the present disclosure exhibits higher removal efficiency.

Further, the amount of the fluorine-containing compound having n of 14 in the general formula (2) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having n of 15 in the general formula (2) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water. When the concentration of the fluorine-containing compound represented by the general formula (2) in the discharge water is above a certain level as described above, the removal method of the present disclosure exhibits higher removal efficiency.

Further, the amount of the fluorine-containing compound having n of 15 in the general formula (2) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having n of 16 in the general formula (2) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water. When the concentration of the fluorine-containing compound represented by the general formula (2) in the discharge water is above a certain level as described above, the removal method of the present disclosure exhibits higher removal efficiency.

Further, the amount of the fluorine-containing compound having n of 16 in the general formula (2) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having n of 17 in the general formula (2) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water. When the concentration of the fluorine-containing compound represented by the general formula (2) in the discharge water is above a certain level as described above, the removal method of the present disclosure exhibits higher removal efficiency.

Further, the amount of the fluorine-containing compound having n of 17 in the general formula (2) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having n of 18 in the general formula (2) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water. When the concentration of the fluorine-containing compound represented by the general formula (2) in the discharge water is above a certain level as described above, the removal method of the present disclosure exhibits higher removal efficiency.

Further, the amount of the fluorine-containing compound having n of 18 in the general formula (2) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having n of 19 in the general formula (2) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water. When the concentration of the fluorine-containing compound represented by the general formula (2) in the discharge water is above a certain level as described above, the removal method of the present disclosure exhibits higher removal efficiency.

Further, the amount of the fluorine-containing compound having n of 19 in the general formula (2) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The amount of the fluorine-containing compound having n of 20 in the general formula (2) is preferably 0.01 ppm or more, more preferably 0.1 ppm or more, still more preferably 0.5 ppm or more, further preferably 1 ppm or more, still further preferably 5 ppm or more, and particularly preferably 10 ppm or more, based on the total amount of discharge water. When the concentration of the fluorine-containing compound represented by the general formula (2) in the discharge water is above a certain level as described above, the removal method of the present disclosure exhibits higher removal efficiency.

Further, the amount of the fluorine-containing compound having n of 20 in the general formula (2) is preferably 10,000 ppm or less, more preferably 5,000 ppm or less, still more preferably 2,000 ppm or less, further preferably 1,000 ppm or less, still further preferably 500 ppm or less, and particularly preferably 200 ppm or less, based on the total amount of discharge water. When the amount of the fluorine-containing compounds in the discharge water is within the above range, the removal efficiency can be further improved.

The fluorine-containing compound preferably includes at least a fluorine-containing compound having m of 7 or more in the general formula (1) or a fluorine-containing compound having n of 8 or more in the general formula (2).

The fluorine-containing compound more preferably contains a fluorine-containing compound having m of 9 or more in the general formula (1) or a fluorine-containing compound having n of 10 or more in the general formula (2), and still more preferably contains a fluorine-containing compound having m of 11 or more in the general formula (1) or a fluorine-containing compound having n of 12 or more in the general formula (2).

Since the removal method of the present disclosure can efficiently remove the fluorine-containing compound represented by the general formula (1) or (2) having a large number of carbon atoms, the method is particularly effective when treating discharge water containing the fluorine-containing compound represented by the general formula (1) having a large m and the fluorine-containing compound represented by the general formula (2) having a large n.

In this case, the two or more fluorine-containing compounds may contain at least one fluorine-containing compound having m of 7 or more, 9 or more, or 11 or more in the general formula (1), or a fluorine-containing compound having n of 8 or more, 10 or more, or 12 or more in the general formula (2), and may contain a fluorine-containing compound having m of less than 7 in the general formula (1), or a fluorine-containing compound having n of less than 8 in the general formula (2).

The fluorine-containing compound preferably contains the compound represented by the general formula (1). The removal method of the present disclosure is particularly effective when the discharge water contains a compound represented by the general formula (1). In particular, it is effective when the discharge water contains a fluorine-containing compound having m of 7 or more, more preferably a fluorine-containing compound having m of 9 or more, and still more preferably a fluorine-containing compound having m of 11 or more in the general formula (1).

The discharge water usually contains an aqueous medium such as water. As used herein, the term "aqueous medium" means to water and a mixed medium containing water and a water-soluble organic solvent (for example, alcohols such as methanol, ethanol, and propanol, esters such as methyl acetate, ketones such as acetone, ethers such as dimethyl ether, and the like).

The discharge water contains two or more fluorine-containing compounds represented by the general formula (1) or (2). Examples of the discharge water include discharge water generated by process for producing a fluorine-containing polymer. The discharge water includes an aqueous solution, a dispersion liquid, and a liquid obtained by liquefying a gas (discharge gas generated in a drying step or the like described later).

As used herein, the term "process for producing a fluorine-containing polymer" means a general process for producing a fluorine-containing polymer by polymerizing one or more monomers containing a fluorine-containing monomer, and is not limited to a specific production process. Fluorine-containing polymers are generally produced by emulsion polymerization or suspension polymerization of one or more monomers containing a fluorine-containing monomer. In emulsion polymerization and suspension polymerization, a hydrocarbon surfactant can be used as an emulsifier. The discharge water preferably includes discharge water obtained in a process for producing a fluorine-containing polymer using a hydrocarbon surfactant. Further, the discharge water preferably contains a hydrocarbon surfactant.

As used herein, the "fluorine-containing monomer" is not limited as long as the fluorine-containing monomer is a monomer having at least one fluorine or fluoroalkyl group, and may include, for example, trifluoroethylene, tetrafluoroethylene (TFE), vinylidene fluoride. (VdF), vinyl fluoride (VF), chlorotrifluoroethylene (CTFE), hexafluoropropylene (HFP), hexafluoroisobutylene, perfluoroalkylethylene, and fluorovinyl ether.

As used herein, the "fluorine-containing polymer" may be obtained by polymerizing the monomer containing one or more fluorine-containing monomers described above, and may be, for example, but not limited to, a polymer containing one or more of the following fluorine-containing polymers: Examples thereof include polytetrafluoroethylene (PTFE) obtained by photopolymerization of TFE; copolymers of TFE with another monomer (fluorine-containing monomers such as vinylidene fluoride, hexafluoropropylene, chlorotrifluoroethylene, and perfluoro(alkyl vinyl ether), hydrocarbon olefins such as ethylene, propylene, and isobutene, alkyl vinyl ethers, etc.) copolymerizable with TFE (for example, tetrafluoroethylene-hexafluoropropylene copolymers (FEP), tetrafluoroethylene-perfluoro(alkyl vinyl ether) copolymers (PFA), ethylene-tetrafluoroethylene copolymers (ETFE), etc.); fluororesins such as polyvinylidene fluoride (PVDF), polychlorotrifluoroethylene (PCTFE), and ethylene-chlorotrifluoroethylene (ECTFE); fluororubbers such as vinylidene fluoride-hexafluoropropylene copolymer (FKM), tetrafluoroethylene-propylene rubber (FEPM), and tetrafluoroethylene-perfluoromethyl vinyl ether rubber (FFKM); and fluorinated elastomers. As used herein, the "fluorine-containing polymer" also includes a low-molecular-weight polymer having a molecular weight of about 10,000 to 500,000 (for example, low-molecular-weight PTFE or the like).

In the removal method of the present disclosure, the fluorine-containing polymer is preferably polytetrafluoroethylene. The removal method of the present disclosure exhibits particularly high removal efficiency when treating discharge water generated in the production of polytetrafluoroethylene.

The polytetrafluoroethylene may be a TFE homopolymer, or may be a modified PTFE containing a TFE unit and a modifying monomer unit based on a modifying monomer copolymerizable with TFE. Further, the polytetrafluoroethylene may be high-molecular-weight PTFE or low-molecular-weight PTFE, but the removal method of the present disclosure is effective particularly when treating discharge water generated in the production of high-molecular-weight PTFE.

Ultra-high-molecular-weight PTFE usually has non-melt processability and is fibrillatable, and has, for example, a standard specific gravity (SSG) of 2.130 to 2.280. The standard specific gravity is determined by the water replacement method in conformity with ASTM D 792 using a sample molded in conformity with ASTM D 4895-89. In the present disclosure, "high-molecular-weight PTFE" means that the standard specific gravity is within the above range.

The removal method of the present disclosure may include the following process for producing a fluorine-containing polymer.

As used herein, the "process for producing a fluorine-containing polymer" is not limited as long as it is included in a process for producing a fluorine-containing polymer, and may include one or more steps constituting a known process for producing a fluorine-containing polymer. The "process for producing a fluorine-containing polymer" may include, in addition to a polymerization step of polymerizing one or more monomers including a fluorine-containing monomer, a pretreatment step (for example, a step of preparing an emulsifier of a predetermined concentration) before the polymerization step and a post-treatment step (for example, a concentration step of an aqueous dispersion, a solid-liquid separation step, a coagulation step, a washing step, a dehydration step, a drying step, a heat treatment step) after the polymerization step. Hereinafter, specific examples of the "process for producing a fluorine-containing polymer" will be described, but the method according to the present embodiment is not limited to the following specific examples.

As described above, the fluorine-containing polymers are generally produced by polymerization of one or more monomers containing a fluorine-containing monomer. Fluorine-containing polymers are generally produced by emulsion polymerization or suspension polymerization. In this polymerization step, an aqueous dispersion in which polymer particles are dispersed in an aqueous medium is obtained. The polymerization step is preferably performed in the presence of a hydrocarbon surfactant.

When used in the form of an aqueous dispersion, the resulting aqueous dispersion may be concentrated by a concentration step (for example, phase separation and concentration, electroconcentration, filtration treatment using an ultrafiltration membrane, filtration treatment using a reverse osmosis membrane (RO membrane), nanofiltration treatment). In that case, the liquid remaining after recovering the concentrated aqueous dispersion may be included in the "discharge water" as used herein.

After the polymerization step, in the coagulation step, a salt or acid is added to the aqueous dispersion to agglomerate the fluorine-containing polymer. Next, in the solid-liquid separation step, the agglomerated fluorine-containing polymer is separated and recovered. The liquid remaining after the fluorine-containing polymer is separated and recovered can be included in the "discharge water" as used herein.

The fluorine-containing polymer separated and recovered in the solid-liquid separation step may be washed with a washing solution such as an aqueous medium in the washing step. The washing solution used in the washing step may be included in the "discharge water" as used herein.

The fluorine-containing polymer separated and recovered in the solid-liquid separation step may be mechanically dehydrated in the dehydration step. The liquid removed from the fluorine-containing polymer in the dehydration step can be included in the "discharge water" as used herein.

The fluorine-containing polymer after dehydration may be washed with a washing solution such as an aqueous medium in the washing step, and the washing solution used in this washing step may also be included in the "discharge water" as used herein.

The fluorine-containing polymer obtained after the washing step and/or dehydration step may be heat-dried in the drying step to remove residual moisture and organic solvent as discharge gas. Liquefied discharge gas generated in the drying step may be included in the "discharge water" as used herein.

The discharge gas generated in the drying step may include, in addition to water vapor and an organic solvent, a fluorine-containing surfactant entrained in the fluorine-containing polymer, and a vaporized fluorine-containing compound represented by general formula (1) or (2) generated during polymerization. Therefore, it is preferable to wash the discharge gas with a washing solution such as water or an alkaline aqueous solution. The washing solution used to clean the discharge gas may also be included in the "discharge water" as used herein.

The fluorine-containing polymer obtained after the drying step may be molded into a desired shape such as pellets in the heat treatment step. Liquefied discharge gas generated in the heat treatment step may be included in the "discharge water" as used herein. The discharge gas generated in the heat treatment step may include vaporized fluorine-containing compounds represented by the general formula (1) or (2) entrained in the fluorine-containing polymer. Therefore, it is preferable to wash the discharge gas with a washing solution such as water or an alkaline aqueous solution. The washing solution used to clean the discharge gas may also be included in the "discharge water" as used herein.

In addition, both the discharge gas generated in the drying step and the discharge gas generated in the heat treatment step may be washed together to obtain a single washing liquid.

The discharge water may be discharge water generated from the production process of one kind of fluorine-containing polymer, or may include discharge water generated from the production process of a plurality of different kinds of fluorine-containing polymers. For example, the discharge water may be a mixture containing discharge water generated from a fluoroelastomer production process and discharge water generated from a PTFE (Low molecular weight PTFE, etc.) production process, and the discharge water generated from the production process of two kinds of fluorine-containing polymers can be treated simultaneously by the removal method of the present disclosure. Further, the discharge water may be discharge water generated from one of the steps included in process for producing a fluorine-containing polymer, or may include discharge water generated from a plurality of different steps.

For example, the discharge water may be a mixture of discharge water obtained in a process for producing a fluorine-containing polymer using a hydrocarbon surfactant and discharge water obtained in a process for producing a fluorine-containing polymer using a fluorine-containing surfactant.

The pH of the discharge water may be, for example, 1.5 to 13.5, or may be 2 to 13.

Also, the discharge water is preferably acidic. By being acidic, the removal efficiency of the fluorine-containing compound can be further improved. For example, the pH of the discharge water in the adsorption step may be 1 to 6, or may be 1 to 5.

Examples of the method for acidifying the discharge water include a method of adjusting the pH by adding an acid before the adsorption step. Examples of the acid include hydrochloric acid (HCl), nitric acid ($HNO_3$), sulfuric acid ($H_2SO_4$), and phosphoric acid ($H_3PO_4$), and hydrochloric acid (HCl) or nitric acid ($HNO_3$) is particularly preferred.

The removal method of the present disclosure includes an adsorption step of bringing the discharge water into contact with an adsorbent to allow the adsorbent to adsorb two or more fluorine-containing compounds.

The temperature in the adsorption step may be, for example, but not limited to, 0 to 50° C. From the viewpoint of increasing the removal ratio, the temperature is preferably 5° C. or higher. Further, the temperature is preferably 40° C. or lower, and more preferably 35° C. or lower. Further, the temperature may be 20° C. or lower.

The pressure in the adsorption step may be, for example, but not limited to, 0.1 to 10 atm, and can be performed at normal pressure (about 1 atm).

The contact time in the adsorption step may be 0.1 seconds to 100 hours, may be 1 second to 50 hours, or may be 1 second to 10 hours. Further, the contact time may be 1 second to 1 hour.

In the removal method of the present disclosure, the contact in the adsorption step may be a batch type or a flow type. The adsorption step may be performed once or may be repeated a plurality of times.

In the adsorption step, the amount of the adsorbent based on the discharge water may be, for example, but not limited to, 0.01 to 1,000 g based on 1,000 g of the discharge water, for example. The amount thereof is preferably 0.1 g or more, more preferably 1 g or more, and still more preferably 5 g or more based on 1,000 g of discharge water. Further, the amount thereof is preferably 500 g or less.

As a method for bringing the discharge water into contact with the adsorbent, a commonly used method can be adopted. For example, the method can be carried out by adding an adsorbent to the discharge water and stirring the discharge water, or by a column method in which discharge water containing the fluorine-containing compound is made to flow through a column filled with the adsorbent. The packed column used in the column method may be a mobile type, a fixed layer type, or a fluidized-bed type.

When a method of adding an adsorbent to discharge water and stirring it is used, it is preferable to include a separation step of separating the adsorbent and the discharge water after the adsorption step after the adsorption step. The method for separating the adsorbent and the discharge water after the adsorption step is not limited, and for example, filtration or the like can be used.

The removal method of the present disclosure may include a step of pretreating discharge water before the adsorption step. Examples of the pretreatment step include a step of removing the uncoagulated polymer from the discharge water, and a step of diluting or concentrating the discharge water.

The removal method of the present disclosure further preferably includes a pretreatment for removing a solid component from the discharge water before the adsorption step. Examples of the solid component include uncoagulated polymers, coagulants, and fine particle polymers.

The discharge water may contain a solid component such as a fluorine-containing polymer. The solid component is a component that can remain in the effluent after the fluorine-containing polymer produced in the process for producing a fluorine-containing polymer is separated and recovered. For example, the coagulation effluent (the liquid remaining after separation and recovery in the solid-liquid separation step after the coagulation step) may contain an uncoagulated polymer that could not be completely recovered in the solid-liquid separation step. Such solid components can adversely affect the process of removing the fluorine-containing compound, so it is desirable to remove them from the discharge water before the adsorption step.

As used herein, the uncoagulated polymer means a polymer component that is present dispersed in the discharge water remaining after the fluorine-containing polymer is separated and recovered by adding a coagulant after the polymerization step and performing a solid-liquid separation step, and deposited as a gel-like substance on the surface of a filter material such as a filter. The particle size of the uncoagulated polymer may be about 0.01 μm to 5.0 μm.

The fine particle polymer that may be contained in the discharge water may be, for example, but not limited to, a polymer having a particle size of about 0.1 μm to 0.2 μm.

The discharge water may contain a solid component, and may contain an uncoagulated polymer and/or a fine particle polymer as a solid component. In the removal method of the present disclosure, the concentration of the solid component in the discharge water is not limited, and discharge water can be treated at any solid component concentration.

The concentration of the solid component in the discharge water may vary depending on the process for producing a fluorine-containing polymer in which the discharge water is produced, and may be, for example, 0.1 ppm to 50,000 ppm.

Further, by the pretreatment step, the concentration is preferably set to 0.1 ppm to 500 ppm, more preferably 0.05 ppm to 50 ppm, and still more preferably 0.05 ppm to 10 ppm.

The method for removing the solid component is not limited, and examples thereof include filtration. Examples of the filtration method include a method of separating solid components by a UF membrane and an MF membrane, a method of using a filtration aid, and a method of using a liquid cyclone.

Examples of the MF membrane include a safety filter, a hollow fiber membrane, a flat membrane, and a spiral.

Examples of the filtration aid include diatomaceous earth, filtered sand (manganese sand, manganese zeolite, anthracite, ceramic sand, etc.), pearlite, and cellulose.

Further, the removal method of the present disclosure may further include a persulfate treatment step of treating with persulfate ions by adding persulfate ions to the discharge water before the adsorption step.

By performing the treatment with persulfate ions, the removal efficiency of the fluorine-containing compound represented by the general formula (1) or (2) can be further improved. Although reason why the removal efficiency of the fluorine-containing compound represented by the general formula (1) or (2) can be further improved by the treatment with the persulfate ion is not beyond the range of speculation, the reason may be that the treatment with persulfate ion causes some kind of decomposition reaction in the fluorine-containing compound represented by the general formula (1) or (2) that decreases the number of carbons, and this makes it easier for the fluorine-containing compound represented by the general formula (1) or (2) to come into contact with the adsorbent in the adsorption step.

When adding persulfate ions used in the persulfate ion treatment step, it is sufficient to add them in the form of compounds containing persulfate ions ($S_2O_8^{2-}$), and persulfate ($H_2S_2O_8$) and its salts can be used as compounds containing persulfate ions. Examples of the persulfate include potassium persulfate ($K_2S_2O_8$), ammonium persulfate (($NH_4$)$_2S_2O_8$), and sodium persulfate ($Na_2S_2O_8$).

The treatment temperature in the persulfate ion treatment step may be, for example, 0 to 95° C. From the viewpoint of increasing the removal ratio, the temperature is preferably 25° C. or higher, more preferably 40° C. or higher, and still more preferably 60° C. or higher. Further, the temperature is preferably 90° C. or lower, and more preferably 85° C. or lower.

The pressure in the persulfate ion treatment step may be, for example, but not limited to, 0.1 to 10 atm, and can be performed at normal pressure (about 1 atm). Alternatively, it can be performed under pressurized conditions, and the treatment temperature at this time can be 100 to 150° C.

The treatment time in the persulfate ion treatment step may be 0.1 seconds to 100 hours, may be 1 second to 50 hours, or may be 1 minute to 20 hours. Further, the treatment time may be 1 hour to 10 hours.

The amount of persulfate ion based on discharge water in the persulfate ion treatment step may be, for example, but not limited to, 0.0001 to 10 g per 1,000 g of discharge water. The amount thereof is preferably 0.001 g or more, more preferably 0.01 g or more, and still more preferably 0.05 g or more based on 1,000 g of discharge water. Further, the amount thereof is preferably 5 g or less.

In addition to the fluorine-containing compound represented by the general formula (1) or (2), the hydrocarbon surfactant, the solid component and the like, the discharge water may contain nitric acid; aluminum salts such as aluminum sulfate and polyaluminum chloride (PAC); ferrous salts such as ferrous hydroxide, ferric hydroxide, ferrous sulfate, ferric sulfate, and polyferric sulfate; calcium salts such as calcium hydroxide, calcium chloride, calcium sulfate, calcium carbonate, calcium nitrate, and calcium fluoride; silicate minerals containing silicon and a di- or higher valent metallic element such as kaolinite, montmorillonite, and zeolite; and coagulants such as sodium alginate, chitin/chitosan coagulant, cationic polymer coagulant, anionic polymer coagulant, and nonionic polymer coagulant. These coagulants may be those used as coagulants in the process for producing a fluorine-containing polymer. Further, the coagulant may be further added to the discharge water before the adsorption step. By adding the coagulant, the amount of solid components in the discharge water can be reduced, and the fluorine-containing compound can be more efficiently adsorbed on the adsorbent.

The adsorbent is not limited as long as it can adsorb the fluorine-containing compound represented by the general formula (1) or (2), but is preferably, for example, at least one selected from the group consisting of an ion exchange resin, a synthetic adsorbent, activated carbon, silica gel, clay, and zeolite, and more preferably at least one selected from the group consisting of an ion exchange resin, a synthetic adsorbent, and activated carbon. Alumina, carbon nanotubes and the like may also be used.

The ion exchange resin may be either a cation exchange resin or an anion exchange resin. The anion exchange resin used may be, for example, an ion exchange resin having an amino group and/or a quaternary ammonium group as a functional group. The ion exchange resin is preferably a strong basic anion exchange resin. The basicity of the anion exchange resin can be variously set according to the type of polymer backbone and/or functional group. Commercially available products may be used as the anion exchange resin, for example, DIAION (trademark) SA series manufactured by Mitsubishi Chemical Co., Ltd., A200, A300, PFA694E manufactured by Purolite Co., Ltd., and Amberlite (trademark) series and Amberjet (trademark) series such as IRA4002OH manufactured by Organo Corporation can be used. The cation exchange resin used may be, for example, an ion exchange resin having a carboxylic acid group and/or a sulfonic acid group as a functional group. The acidity of the cation exchange resin can be variously set according to the type of polymer backbone and/or functional group. Commercially available products may be used as the cation exchange resin, for example, DIAION (trademark) SK series manufactured by Mitsubishi Chemical Co., Ltd., C100 manufactured by Purolite Co., Ltd., and Amberlite (trademark) series manufactured by Organo Corporation can be used.

The ion exchange resin preferably has a pore diameter of 1 to 5,000 Å. From the viewpoint of removal efficiency, the pore diameter is preferably 50 Å or more, more preferably 100 Å or more, and still more preferably 150 Å or more. Alternatively, the pore diameter may be 200 Å or more, or may be 250 Å or more. Alternatively, the pore diameter may be 1,000 Å or less. The pore diameter can be calculated by measuring the specific surface area and the total pore volume by, for example, a gas adsorption method.

From the viewpoint of removal efficiency, the ion exchange resin preferably has a total exchange capacity of 0.1 eq/L-Resin or more. The total exchange capacity is more preferably 0.5 eq/L-Resin or more, and still more preferably 0.9 eq/L-Resin or more. Further, the larger the total exchange capacity is, the better, but for example, the upper limit may be 5.0 eq/L-Resin.

Further, the ion exchange resin is usually spherical and has an average particle size of about 300 to 1300 μm.

Further, the anion exchange resin may be an anion exchange resin A having an ion exchange group represented by the following general formula (A1):

—$N^+R^{c1}R^{c2}R^{c3}X^-$ group (wherein, $R^{c1}$, $R^{c2}$ and $R^{c3}$ are the same or different and each are a hydrogen atom or an organic group and at least one of $R^{c1}$, $R^{c2}$, and $R^{c3}$ is an organic group having 3 or more carbon atoms; and X represents a counterion) or an ion exchange group represented by the following general formula (A2):

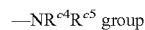
—$NR^{c4}R^{c5}$ group (wherein $R^{c4}$ and $R^{c5}$ are the same or different and each are a hydrogen atom or an organic group, and at least one of $R^{c4}$ and $R^{c5}$ is an organic group having 2 or more carbon atoms).

In the general formula (A1), $R^{c1}$, $R^{c2}$, and $R^{c3}$ are the same or different and each are a hydrogen atom or an organic group. All of $R^{c1}$, $R^{c2}$, and $R^{c3}$ may be organic groups, or one may be a hydrogen atom and two may be organic groups. Alternatively, two may be hydrogen atoms and one may be an organic group. The organic group has 1 or more carbon atoms. The organic group preferably has 2 or more carbon atoms. In a preferred embodiment, $R^{c1}$, $R^{c2}$ and $R^{c3}$ are organic groups having 2 or more carbon atoms.

In the general formula (A1), at least one of $R^{c1}$, $R^{c2}$ and $R^{c3}$ is an organic group having 3 or more carbon atoms. Of $R^{c1}$, $R^{c2}$ and $R^{c3}$, one may be an organic group having 3 or more carbon atoms and two may be a hydrogen atom or an organic group having 1 or 2 carbon atoms. Alternatively, two may be an organic group having 3 or more carbon atoms, and one may be a hydrogen atom or an organic group having 1 or 2 carbon atoms. All of $R^{c1}$, $R^{c2}$ and $R^{c3}$ may be an organic group having 3 or more carbon atoms.

In $R^{c1}$, $R^{c2}$, and $R^{c3}$, the organic group preferably has 10 or less, more preferably 8 or less, and still more preferably 6 or less carbon atoms. The organic group may have 5 or less carbon atoms.

In the general formula (A1), at least one of $R^{c1}$, $R^{c2}$, and $R^{c3}$ is preferably an organic group having 4 or more carbon atoms. By adopting such a configuration, a specific fluorine-containing compound can be removed more efficiently.

The organic group in $R^{c1}$, $R^{c2}$, and $R^{c3}$ is preferably an alkyl group, an alkanol group or an alkenyl group, more preferably an alkyl group or an alkanol group, and still more preferably an alkyl group. The alkanol group may be any remaining group obtained by removing one hydrogen atom from the alkanol, including a linear or branched alkanol group having 1 or more carbon atoms or a cyclic alkanol group having 3 or more carbon atoms.

$R^{c1}$, $R^{c2}$, and $R^{c3}$ are the same or different and each are an alkyl group having 2 or more carbon atoms or an alkanol group having 1 or more carbon atoms, and at least one of $R^{c1}$, $R^{c2}$ and $R^{c3}$ is preferably an alkyl group having 3 or more carbon atoms.

In a more preferred embodiment, $R^{c1}$, $R^{c2}$, and $R^{c3}$ are the same or different and each are an alkyl group having 2 or more carbon atoms or an alkanol group having 2 or more carbon atoms and at least one of $R^{c1}$, $R^{c2}$ and $R^{c3}$ is an alkyl group having 3 or more carbon atoms.

In another preferred embodiment, $R^{c1}$, $R^{c2}$, and $R^{c3}$ are the same or different and each are an alkyl group having 2 or more carbon atoms or an alkanol group having 1 or more carbon atoms and at least one of $R^{c1}$, $R^{c2}$ and $R^{c3}$ is more preferably an alkyl group having 4 or more carbon atoms.

In still another preferred embodiment, $R^{c1}$, $R^{c2}$, and $R^{c3}$ are the same or different and each are an alkyl group having 2 or more carbon atoms or an alkanol group having 2 or more carbon atoms and at least one of $R^{c1}$, $R^{c2}$ and $R^{c3}$ is more preferably an alkyl group having 4 or more carbon atoms.

The alkyl group preferably has 10 or less, more preferably 8 or less, and still more preferably 6 or less carbon atoms. The alkyl group may have 5 or less carbon atoms.

The alkanol group preferably has 10 or less, more preferably 8 or less, and still more preferably 6 or less carbon atoms. The alkanol group may have 5 or less carbon atoms.

In the general formula (A1), X is a counterion. Examples of X include Cl, OH, Br, I, $NO_3$, and $SO_4$, and Cl, OH, or OH is preferred. In the case of a divalent anion such as $SO_4$, one counterion coordinates with two groups represented by the general formula (A1).

In the general formula (A2), $R^{c4}$ and $R^{c5}$ are the same or different and each are a hydrogen atom or an organic group and at least one of $R^{c4}$ and $R^{e}s$ is an organic group having 2 or more carbon atoms.

All of $R^{c4}$ and $R^{e}s$ may be organic groups. Alternatively, one may be a hydrogen atom and one may be an organic group.

In the general formula (A2), at least one of $R^{c4}$ and $R^{c5}$ is an organic group having 2 or more carbon atoms.

Of $R^{c4}$ and $R^{e}S$, one may be an organic group having 2 or more carbon atoms and one may be a hydrogen atom or an organic group having 1 carbon atom. Alternatively, both $R^{c4}$ and $R^{c5}$ may be organic groups having 2 or more carbon atoms.

At least one of $R^{c4}$ and $R^{c5}$ may be an organic group having 3 or more carbon atoms, or may be an organic group having 4 or more carbon atoms.

Further, $R^{c4}$ and $R^{c5}$ are also preferably an organic group having 2 or more carbon atoms.

In $R^{c4}$ and $R^{c5}$, the organic group preferably has 10 or less, more preferably 8 or less, and still more preferably 6 or less carbon atoms. The organic group may have 5 or less carbon atoms.

The organic group in $R^{c4}$ and $R^{c5}$ is preferably an alkyl group, an alkanol group or an alkenyl group, more preferably an alkyl group or an alkanol group, and still more preferably an alkyl group.

In a more preferred embodiment, $R^{c4}$ and $R^{c5}$ are the same or different and each are an alkyl group or an alkanol group, and at least one of $R^{c4}$ and $R^{c5}$ is an alkyl group having 2 or more carbon atoms or an alkanol group having 2 or more carbon atoms.

The alkyl group preferably has 10 or less, more preferably 8 or less, and still more preferably 6 or less carbon atoms. The alkyl group may have 5 or less carbon atoms.

The alkanol group preferably has 10 or less, more preferably 8 or less, and still more preferably 6 or less carbon atoms. The alkanol group may have 5 or less carbon atoms.

The anion exchange resin A preferably has a group represented by the general formula (A1) or a group represented by the general formula (A2) bonded to the resin base. Examples of the anion exchange resin include a resin base comprising a styrene or acrylic polymer, to which a group represented by the general formula (A1) or a group represented by the general formula (A2) is bonded. The styrene or acrylic polymer as the resin base is not limited, and for example, a resin base used in a known anion exchange resin can be used.

The basicity of the anion exchange resin A can be variously set according to the type of polymer backbone and/or ion exchange group.

The pore diameter and total exchange capacity of the anion exchange resin A may be within the above ranges.

From the viewpoint of removal efficiency, the moisture content of the anion exchange resin A is preferably 20% by mass or more, more preferably 30 to 70% by mass, and still more preferably 35 to 65% by mass.

The moisture content can be measured by the following method.

First, 10 mL of the standard sample is accurately weighed with a measuring cylinder, the resin is wrapped in a cloth and centrifuged to remove adhering moisture, and then the mass of the resin is quickly measured. Next, after drying in a constant temperature dryer at 105° C. for 4 hours, the mixture is allowed to cool in a desiccator for 30 minutes, the mass of the dried resin is weighed, and the moisture content is calculated by the following formula.

Moisture content (%)=(mass of resin before drying (g)−mass of resin after drying (g))/mass of resin before drying (g)×100

The anion exchange resin A is usually spherical. The anion exchange resin A preferably has an average particle size of 0.1 to 5 mm, more preferably 0.2 to 2 mm, and particularly preferably 0.3 to 1.5 mm. When the average particle size of the anion exchange resin A is within the above range, the column filled with the anion exchange resin is less likely to be blocked. The average particle size is a value obtained by the sieving method. Specifically, first, the anion exchange resin A is placed in a sieve shaker, and the particle size distribution is measured by sieving. Then, the diameter of the sieve mesh corresponding to the residual classification total of 50% is determined and taken as the average particle size.

Commercially available products may be used as the anion exchange resin A, and examples thereof include PFA694E and A592E manufactured by Purolite Co., Ltd.

Furthermore, the anion exchange resin may be an anion exchange resin B having a group represented by the following general formula (B1):

—N$^+$(CH$_3$)$_3$X$^-$ group (wherein X represents a counterion) or an anion exchange group represented by the following general formula (B2):

—N$^+$(CH$_3$)$_2$(C$_2$H$_4$OH)X$^-$ group (wherein X represents a counterion).

Examples of X in the general formulas (B1) and (B2) include Cl, OH, Br, I, NO$_3$, and SO$_4$, and Cl, OH, or OH is preferred. In the case of a divalent anion such as SO$_4$, one counterion coordinates with two groups represented by the general formula (B1) or the general formula (B2).

The anion exchange resin B is preferably a resin in which the ion exchange group is bonded to the resin base, and examples of the resin base include styrene or acrylic polymers. The styrene or acrylic polymer as the resin base is not limited, and for example, a resin base used in a known anion exchange resin can be used. From the viewpoint of removal efficiency, the anion exchange resin B preferably has a styrene resin base.

The anion exchange resin B may be weakly basic or strongly basic. A strong basic anion exchange resin is preferred.

The basicity of the anion exchange resin B can be variously set according to the type of polymer backbone and/or ion exchange group.

The anion exchange resin B preferably has a pore diameter of 1 to 5,000 Å. From the viewpoint of removal efficiency, the pore diameter is preferably 50 Å or more, more preferably 100 Å or more, and still more preferably 150 Å or more. Alternatively, the pore diameter may be 200 Å or more, or may be 250 Å or more. Alternatively, the pore diameter may be 1,000 Å or less. The pore diameter can be calculated by measuring the specific surface area and the total pore volume by, for example, a gas adsorption method.

From the viewpoint of removal efficiency, the anion exchange resin B preferably has a total exchange capacity of 0.1 eq/L-Resin or more. The total exchange capacity is more preferably 0.3 eq/L-Resin or more, still more preferably 0.5 eq/L-Resin or more, and particularly preferably 0.7 eq/L-Resin or more. The larger the total exchange capacity, the better, but for example, the upper limit is preferably 5.0 eq/L-Resin, more preferably 2.0 eq/L-Resin or less, and particularly preferably 1.5 eq/L-Resin.

The moisture content of the anion exchange resin B is preferably 20% by mass or more, more preferably 30 to 70% by mass, and still more preferably 35 to 65% by mass. When the moisture content of the anion exchange resin B is 30% by mass or more, the removal can be efficiently performed.

The moisture content can be measured by the same method as the anion exchange resin A described above.

The anion exchange resin B is usually spherical. The anion exchange resin B preferably has an average particle size of 0.1 to 5 mm, more preferably 0.2 to 2 mm, and particularly preferably 0.3 to 1.5 mm. When the average particle size of the anion exchange resin B is within the above range, the column filled with the anion exchange resin is less likely to be blocked. The average particle size is a value obtained by the sieving method. Specifically, first, the anion exchange resin B is placed in a sieve shaker, and the particle size distribution is measured by sieving. Then, the diameter of the sieve mesh corresponding to the residual classification total of 50% is determined and taken as the average particle size.

Commercially available products may be used as the anion exchange resin B, for example, DIAION (trademark) SA series manufactured by Mitsubishi Chemical Co., Ltd., A400 and A300 manufactured by Purolite Co., Ltd., and Amberlite (trademark) series and Amberjet (trademark) series such as IRA4002OH manufactured by Organo Corporation can be used.

The synthetic adsorbent is a porous resin having no ion exchange group, and a known synthetic adsorbent known as a synthetic adsorbent can be adopted. Examples of the ion exchange group include an amino group, a quaternary ammonium group, a carboxylic acid group, and a sulfonic acid group. Specific examples of the synthetic adsorbent include styrene resins such as styrene-divinylbenzene copolymers, acrylic resins such as (meth)acrylate ester-ethylene glycol dimethacrylate copolymers, methacrylic resins, polyvinyl resins, and dextran resins. Specific examples of commercially available synthetic adsorbents include styrene resins such as DIAION HP10, DIAION HP20, DIAION HP21, DIAION HP40, DIAION HP50, Sepabeads SP207, Sepabeads SP70, Sepabeads SP825, Sepabeads SP850, Sepabeads SP207 (all, manufactured by Mitsubishi Chemical Co., Ltd.), and Amberlite XAD1180N, Amberlite XAD2000, Amberlite XAD4, Amberlite FPX66 (all, manufactured by Organo Corporation); and acrylic resins such as DIAION HP2MG (manufactured by Mitsubishi Chemical Co., Ltd.), Amberlite HXAD-7HP (manufactured by Organo Corporation).

The synthetic adsorbent preferably has a pore diameter of 1 to 5,000 Å. From the viewpoint of removal efficiency, the pore diameter is preferably 50 Å or more, more preferably 100 Å or more, and still more preferably 150 Å or more. Alternatively, the pore diameter may be 200 Å or more, or may be 250 Å or more. Alternatively, the pore diameter may be 1,000 Å or less. The pore diameter can be calculated by measuring the specific surface area and the total pore volume by, for example, a gas adsorption method.

The synthetic adsorbent preferably has a specific surface area of 300 m$^2$/g or more. The specific surface area is more preferably 400 m$^2$/g or more, still more preferably 500 m$^2$/g or more, and still further preferably 600 m$^2$/g or more. The upper limit of the specific surface area may be, for example, but not limit to, 2,000 m$^2$/g or less, 1,500 m$^2$/g or less, or 1,000 m$^2$/g or less. Further, the synthetic adsorbent is usually spherical, and the synthetic adsorbent preferably has an average particle size of 0.1 to 2.0 mm, more preferably 0.2 to 1.5 mm, and more preferably 0.2 to 1.3 mm, and particularly preferably 0.3 to 1.0 mm, from the viewpoint of removal efficiency. The average particle size of the synthetic adsorbent means the 50% mass value obtained by plotting the integrated mass after classification by sieving on a graph.

The synthetic adsorbent preferably contains moisture from the viewpoint of increasing the removal efficiency. The moisture content is preferably 20 to 80% by mass, more preferably 40 to 75% by mass, and particularly preferably 50 to 70% by mass.

The activated carbon can be produced from a carbonaceous material. The carbonaceous material may be any material which generates activated carbon by carbonization, activation or the like, and examples thereof include as wood, sawdust, charcoal, fruit husks such as coconut husks and walnut husks, vegetable materials such as fruit seeds, coal such as peat, lignite, brown coal, bituminous coal, and anthracite, pitch such as petroleum pitch and coal pitch, tars such as cokes, coal tar, and petroleum tar, mineral materials such as petroleum distillation residues, natural materials such as cellulosic fibers such as cotton and rayon, and synthetic materials such as phenolic resin, polyvinyl alcohol and polyacrylonitrile. The carbonaceous material can be in powder, granular, or fibrous form, or can be molded.

The activated carbon preferably has a specific surface area of 500 m$^2$/g or more. The specific surface area is more preferably 1,000 m$^2$/g or more, still more preferably 1,500 m$^2$/g or more, still further preferably 1,800 m$^2$/g or more, and particularly preferably 2,000 m$^2$/g or more. The upper limit of the specific surface area may be, for example, but not limited to, 2,500 m$^2$/g. The shape of the activated carbon may be, for example, but not limited to, the shape of pellets, granules, powder, or spherical particles. The activated carbon may be a commercially available product. Commercially available products of activated carbon include, for example, Shirasagi (trademark) manufactured by Osaka Gas Chemical Co., Ltd., Filtrasorb (trademark) CAL, Diahope (trademark), Diasorb (trademark) manufactured by Calgon Carbon Japan Co., Ltd, and Evadia (trademark) series manufactured by Swing Corporation.

The activated carbon preferably has improved adsorption performance by performing a steam activation treatment. In the steam activation treatment, the activated carbon may be exposed to steam at a temperature of 120° C. or higher, for example 130 to 350° C., particularly 150 to 1,000° C., and a pressure of 0.2 MPa or higher, for example 0.5 to 15 MPa, particularly preferably 1 MPa to 15 MPa. The steam activation treatment time is generally 10 seconds to 50 hours, for example, 10 minutes to 10 hours. In the activation, heating may be performed in the furnace.

A cation may be impregnated on the surface of the activated carbon. Examples of cations include metal ions, metal oxide ions, and ammonium ions. Examples of metals include metal atoms of groups 1 to 13 of the periodic table (for example, alkali metals (for example, Li, Na, K), alkaline earth metals (for example, Mg, Ca), Ti, Zr, V, Cr, Fe, Ni, Cu, Zn).

The removal method of the present disclosure may include a step of concentrating the discharge water that has undergone the adsorption step after the adsorption step.

Examples of the concentration method include phase separation concentration, ion exchanger method, and membrane concentration. The phase separation concentration, ion exchanger method and membrane concentration can be carried out under conventionally known treatment conditions, and can be carried out, but are not limited, by the method disclosed in International Publication No. 2004/050719 Pamphlet, National Publication of International Patent Application No. 2002-532583, and Japanese Patent Laid-Open No. 55-120630.

The adsorbent having adsorbed the fluorine-containing compound represented by the general formula (1) or (2) may be treated with an alkali solution containing water and an organic solvent to elute and reuse the adsorbed fluorine-containing compound.

The alkali used may be hydroxides of alkali metals such as NaOH and KOH, and NH$_4$OH.

Further, the eluted fluorine-containing compound may be recovered.

In the adsorption step, the removal ratio of the fluorine-containing compound represented by the general formula (1) or (2) is preferably 40% or more, more preferably 50% or more, still more preferably 60% or more, further preferably 70% or more, still further preferably 80% or more, particularly preferably 90% or more, more preferably 95% or more, further preferably 99% or more, and most preferably 99.9% or more. The removal ratio is obtained by measuring the concentration of the fluorine-containing compound represented by general formula (1) or (2) before and after the adsorption step, and then by the following formula:

Removal ratio (%)=(1−peak area of fluorine-containing compound represented by general formula (1) or (2) after adsorption step)/(peak area of fluorine-containing compound represented by general formula (1) or (2) before adsorption step)×100

The concentration of the fluorine-containing compound can be measured by the method described in Examples described later.

The adsorption step may be repeated a plurality of times, and the removal ratio in the case of repeating a plurality of times is calculated from the concentration of the fluorine-containing compound before the first adsorption step and the concentration of the fluorine-containing compound after the last adsorption step.

If repeated a plurality of times, it can be 2, 3, 4, 5, 6, 7, 8, 9, or 10 times. It can be 2 to 10 times, 2 to 7 times, and 3 to 5 times.

If the adsorption steps are repeated a plurality of times, the same adsorbent may be used or different adsorbents may be used in each adsorption step. For example, when the adsorption step is performed twice, the same adsorbent may be used for the first time and for the second time or different adsorbents may be used. Further, for example, when the above adsorption step is performed three or more times, various embodiments, such as an embodiment in which the same adsorbent is used for the first and second times and another adsorbent is used for the third time, and an embodiment in which different adsorbents are used for the first, second, and third times, can be employed.

For example, when the anion exchange resin A and the anion exchange resin B are used as the adsorbent, the adsorption step using the anion exchange resin A can be performed one or more times, and then the adsorption step using the anion exchange resin B can be performed one or more times. Alternatively, after performing the adsorption step using the anion exchange resin B one or more times, the adsorption step using the anion exchange resin A can be performed one or more times.

Further, for example, when the synthetic adsorbent and the anion exchange resin B are used as the adsorbent, the adsorption step using the synthetic adsorbent can be performed one or more times, and then the adsorption step using the anion exchange resin B can be performed one or more times. Alternatively, after performing the adsorption step using the anion exchange resin B one or more times, the adsorption step using the synthetic adsorbent can be performed one or more times.

The discharge water treated by the removal method of the present disclosure preferably has a total amount of the fluorine-containing compounds represented by the general formula (1) or (2) of 100 ppm or less. The total amount is more preferably 10 ppm or less, still more preferably 1 ppm or less, further preferably 0.1 ppm or less, and particularly preferably 0.01 ppm or less.

The discharge water is preferably discharge water obtained by polymerization using a hydrocarbon surfactant. When a fluorine-containing polymer is produced by polymerization using a hydrocarbon surfactant, the discharge water may contain two or more compounds represented by the general formula (1) or (2) together with the hydrocarbon surfactant. That is, the discharge water may further contain a hydrocarbon surfactant. Further, the removal method of the present disclosure may include a step of polymerizing a fluorine monomer in an aqueous medium in the presence of a hydrocarbon surfactant.

The removal method of the present disclosure can also remove the hydrocarbon surfactant used in the polymerization.

In the removal method of the present disclosure, the concentration of the hydrocarbon surfactant in the discharge water is not limited, and discharge water can be treated at any concentration of the hydrocarbon surfactant. The concentration of the hydrocarbon surfactant in the discharge water may vary depending on the process for producing a fluorine-containing polymer in which the discharge water is produced, and may be about 0.1 ppm to about 50,000 ppm or may be, for example, 1 ppm to 10,000 ppm or 1 to 5,000 ppm. The discharge water generated from the process for producing a fluorine-containing polymer can be treated as it is by the method according to the present disclosure without pretreatment, but pretreatment such as dilution may also be appropriately performed.

The hydrocarbon surfactant may be, but not limited to, for example, those disclosed in National Publication of International Patent Application No. 2013-542308, National Publication of International Patent Application No. 2013-542309, and National Publication of International Patent Application No. 2013-542310.

The hydrocarbon surfactant may be a surfactant having a hydrophilic moiety and a hydrophobic moiety on the same molecule. These may be cationic, nonionic or anionic.

Cationic hydrocarbon surfactants usually have a positively charged hydrophilic part such as alkylated ammonium halide such as alkylated ammonium bromide and a hydrophobic part such as long chain fatty acids.

Hydrocarbon anionic surfactants usually have a hydrophilic part such as a carboxylate, a sulfonate or a sulfate and a hydrophobic part that is a long chain hydrocarbon moiety such as alkyl.

Nonionic hydrocarbon surfactants are usually free from charged groups and have hydrophobic moieties that are long chain hydrocarbons. The hydrophilic moiety of the nonionic surfactant contains water-soluble functional groups such as chains of ethylene ether derived from polymerization with ethylene oxide.

Examples of nonionic hydrocarbon surfactants Polyoxyethylene alkyl ether, polyoxyethylene alkyl phenyl ether, polyoxyethylene alkyl ester, sorbitan alkyl ester, polyoxyethylene sorbitan alkyl ester, glycerol ester, and derivatives thereof.

Specific examples of polyoxyethylene alkyl ethers: polyoxyethylene lauryl ether, polyoxyethylene cetyl ether, polyoxyethylene stearyl ether, polyoxyethylene oleyl ether, polyoxyethylene biphenyl ether, and the like.

Specific examples of polyoxyethylene alkyl phenyl ether: polyoxyethylene nonylphenyl ether, polyoxyethylene octylphenyl ether, and the like.

Specific examples of polyoxyethylene alkyl esters: polyethylene glycol monolaurylate, polyethylene glycol monooleate, polyethylene glycol monostearate, and the like.

Specific examples of sorbitan alkyl ester: polyoxyethylene sorbitan monolaurate, polyoxyethylene sorbitan monopalmitate, polyoxyethylene sorbitan monostearate, polyoxyethylene sorbitan monooleate, and the like.

Specific examples of polyoxyethylene sorbitan alkyl ester: polyoxyethylene sorbitan monolaurate, polyoxyethylene sorbitan monopalmitate, polyoxyethylene sorbitan monostearate, and the like.

Specific examples of glycerol ester: glycerol monomyristate, glycerol monostearate, glycerol monooleate, and the like.

Specific examples of the above derivatives: polyoxyethylene alkylamine, polyoxyethylene alkylphenyl-formaldehyde condensate, polyoxyethylene alkyl ether phosphate, and the like.

The ethers and esters may have an HLB value of 10 to 18.

Examples of nonionic hydrocarbon surfactants include Triton X series (X15, X45, X100, etc.), Tergitol® 15-S series, and Tergitol® manufactured by Dow Chemical Company, TMN series (TMN-6, TMN-10, TMN-100, etc.), Tergitol® L series, Pluronic® R series (31R1, 17R2, 10R5, 25R4 (m to 22, n to 23), and Iconol® TDA series (TDA-6, TDA-9, TDA-10) manufactured by BASF.

Examples of the hydrocarbon anionic surfactant include Versatic® 10 manufactured by Resolution Performance Products, and Avanel S series (S-70, S-74, etc.) manufactured by BASF.

Examples of the hydrocarbon surfactant include a hydrocarbon anionic surfactant represented by R-L-M, wherein R is a linear or branched alkyl group having 1 or more carbon atoms and optionally having a substituent, or a cyclic alkyl group having 3 or more carbon atoms and optionally having a substituent, and optionally contains a monovalent or divalent heterocycle or optionally forms a ring when having 3 or more carbon atoms; L is —ArSO$_3^-$, —SO$_3^-$, —SO$_4$—, —PO$_3^-$ or —COO$^-$, and, M is, H, a metal atom, NR$^b_4$, imidazolium optionally having a substituent, pyridinium optionally having a substituent, or phosphonium optionally having a substituent, where each R$^b$ is H or an organic group, and —ArSO$_3^-$ is an aryl sulfonate.

Specific examples thereof include a compound represented by CH$_3$—(CH$_2$)$_n$-L-M, wherein n is an integer of 6 to 17. L and M are the same as described above.

Mixtures of those in which R is an alkyl group having 12 to 16 carbon atoms and L is sulfate or sodium dodecyl sulfate (SDS) can also be used.

Examples of other compounds having a surfactant function include a hydrocarbon anionic surfactant represented by R$^6$-(L-M)$_2$, wherein R$^6$ is H, a linear or branched alkylene group having 1 or more carbon atoms and optionally having a substituent, or a cyclic alkylene group having 3 or more carbon atoms and optionally having a substituent, and optionally contains a monovalent or divalent heterocycle or optionally forms a ring when having 3 or more carbon atoms; L is —ArSO$_3^-$, —SO$_3^-$, —SO$_4$—, —PO$_3^-$ or —COO$^-$, and, M is, H, a metal atom, NR$^b_4$, imidazolium optionally having a substituent, pyridinium optionally having a substituent, or phosphonium optionally having a substituent, where each R$^b$ is H or an organic group, and —ArSO$_3^-$ is an aryl sulfonate.

Examples of the hydrocarbon surfactant include an anionic surfactant represented by R$^7$(-L-M)$_3$, wherein R$^7$ is a linear or branched alkylidine group having 1 or more carbon atoms and optionally having a substituent, or a cyclic alkylidine group having 3 or more carbon atoms and optionally having a substituent, and optionally contains a monovalent or divalent heterocycle or optionally forms a ring when having 3 or more carbon atoms; L is —ArSO$_3^-$, —SO$_3^-$, —SO$_4$—, —PO$_3^-$ or —COO$^-$, and, M is, H, a metal atom, NR$^b_4$, imidazolium optionally having a substituent, pyridinium optionally having a substituent, or phosphonium optionally having a substituent, each $R^b$ are H or an organic group; and —$ArSO_3^-$ is an aryl sulfonate.

Examples of the hydrocarbon surfactant include a siloxane hydrocarbon surfactant. Examples of the siloxane hydrocarbon surfactant include those described in Silicone Surfactants, R. S. M. Hill, Marcel Dekker, Inc., ISBN: 0-8247-00104. The structure of the siloxane hydrocarbon surfactant includes defined hydrophobic and hydrophilic moieties. The hydrophobic moiety contains one or more dihydrocarbyl siloxane units, where the substituents on the silicone atoms are completely hydrocarbon.

In the sense that the carbon atoms of the hydrocarbyl groups are fully substituted with hydrogen atoms where they can be substituted by halogen such as fluorine, these siloxane hydrocarbon surfactants can also be regarded as hydrocarbon surfactants, i.e. the monovalent substituents on the carbon atoms of the hydrocarbyl groups are hydrogen.

The hydrophilic moiety of the siloxane hydrocarbon surfactant may contain one or more polar moieties including ionic groups such as sulfate, sulfonate, phosphonate, phosphate ester, carboxylate, carbonate, sulfosuccinate, taurate (as the free acid, a salt or an ester), phosphine oxides, betaine, betaine copolyol, or quaternary ammonium salts. Ionic hydrophobic moieties may also contain ionically functionalized siloxane grafts.

Examples of such siloxane hydrocarbon surfactants include polydimethylsiloxane-graft-(meth)acrylic acid salts, polydimethylsiloxane-graft-polyacrylate salts, and polydimethylsiloxane-grafted quaternary amines.

The polar moieties of the hydrophilic moiety of the siloxane hydrocarbon surfactant may contain nonionic groups formed by polyethers, such as polyethylene oxide (PEO), and mixed polyethylene oxide/polypropylene oxide polyethers (PEO/PPO); mono- and disaccharides; and water-soluble heterocycles such as pyrrolidinone. The ratio of ethylene oxide to propylene oxide (EO/PO) may be varied in mixed polyethylene oxide/polypropylene oxide polyethers.

The hydrophilic moiety of the siloxane hydrocarbon surfactant may also contain a combination of ionic and nonionic moieties. Such moieties include, for example, ionically end-functionalized or randomly functionalized polyether or polyol. Preferred for carrying out the present disclosure is a siloxane having a nonionic moiety, i.e., a nonionic siloxane surfactant.

The arrangement of the hydrophobic and hydrophilic moieties of the structure of a siloxane hydrocarbon surfactant may take the form of a diblock polymer (AB), triblock polymer (ABA), wherein the "B" represents the siloxane portion of the molecule, or a multi-block polymer. Alternatively, the siloxane hydrocarbon surfactant may contain a graft polymer.

The siloxane hydrocarbon surfactants also include those disclosed in U.S. Pat. No. 6,841,616.

Examples of the siloxane-based hydrocarbon anionic surfactant include Noveon® by Lubrizol Advanced Materials, Inc. and SilSense™ PE-100 silicone and SilSense™ CA-1 silicone available from Consumer Specialties.

Examples of the hydrocarbon anionic surfactant also include a sulfosuccinate surfactant Lankropol® K8300 by Akzo Nobel Surface Chemistry LLC.

Examples of the sulfosuccinate surfactant include sodium diisodecyl sulfosuccinate (Emulsogen® SB10 by Clariant) and sodium diisotridecyl sulfosuccinate (Polirol® TR/LNA by Cesapinia Chemicals).

Examples of the hydrocarbon surfactants also include PolyFox® surfactants by Omnova Solutions, Inc. (PolyFox™ PF-156A, PolyFox™ PF-136A, etc.).

The hydrocarbon surfactant is preferably a hydrocarbon anionic surfactant. The hydrocarbon anionic surfactant used may be those described above, including the following preferred hydrocarbon surfactants.

Examples of the hydrocarbon anionic surfactant include a compound (α) represented by the following formula (α):

$$R^{100}\text{—COOM} \qquad (\alpha)$$

wherein $R^{100}$ is a monovalent organic group containing 1 or more carbon atoms; and M is H, a metal atom, $NR^{101}_4$, imidazolium optionally having a substituent, pyridinium optionally having a substituent, or phosphonium optionally having a substituent, wherein $R^{101}$ is H or an organic group and may be the same or different. $R^{101}$ is preferably H or an organic group having 1 to 10 carbon atoms, and more preferably H or an organic group having 1 to 4 carbon atoms.

From the viewpoint of surfactant function, the number of carbon atoms in $R^{100}$ is preferably 2 or more, and more preferably 3 or more. From the viewpoint of water-solubility, the number of carbon atoms in $R^{100}$ is preferably 29 or less, and more preferably 23 or less.

Examples of the metal atom as M include alkali metals (Group 1) and alkaline earth metals (Group 2), and preferred is Na, K, or Li. M is preferably H, a metal atom, or $NR^{101}_4$, more preferably H, an alkali metal (Group 1), an alkaline earth metal (Group 2), or $NR^{101}_4$, still more preferably H, Na, K, Li, or $NH_4$, further preferably Na, K, or $NH_4$, particularly preferably Na or $NH_4$, and most preferably $NH_4$.

Examples of the compound (α) include a hydrocarbon anionic surfactant represented by $R^{102}$—COOM, wherein $R^{102}$ is a linear or branched, alkyl group, alkenyl group, alkylene group, or alkenylene group having 1 or more carbon atoms and optionally having a substituent, or a cyclic alkyl group, alkenyl group, alkylene group, or alkenylene group having 3 or more carbon atoms and optionally having a substituent, each of which optionally contains an ether bond; when having 3 or more carbon atoms, $R^{102}$ optionally contains a monovalent or divalent heterocycle, or optionally forms a ring; and M is the same as above.

Specific examples thereof include a compound represented by $CH_3$—$(CH_2)_n$—COOM, wherein n is an integer of 2 to 28, and M is as described above.

From the viewpoint of emulsion stability, the compound (α) is preferably free from a carbonyl group which is not in a carboxyl group.

Preferred examples of the hydrocarbon surfactant free from a carbonyl group include a compound of the following formula (A):

$$R\text{—COO-M} \qquad (A)$$

wherein R is an alkyl group, an alkenyl group, an alkylene group, or an alkenylene group containing 6 to 17 carbon atoms, each of which optionally contains an ether bond; M is H, a metal atom, $NR^{101}_4$, imidazolium optionally having a substituent, pyridinium optionally having a substituent, or phosphonium optionally having a substituent; and $R^{101}$ is the same or different and is H or an organic group having 1 to 10 carbon atoms. In the formula (A), R is preferably an alkyl group or an alkenyl group, each of which optionally contains an ether group. The alkyl group or alkenyl group for R may be linear or branched. The number of carbon atoms in R may be, but is not limited to, 4 to 29.

When the alkyl group is linear, the number of carbon atoms in R is preferably 3 to 29, and more preferably 5 to 23. When the alkyl group is branched, the number of carbon atoms in R is preferably 5 to 35, and more preferably 11 to 23.

When the alkenyl group is linear, the number of carbon atoms in R is preferably 2 to 29, and more preferably 9 to 23. When the alkenyl group is branched, the number of carbon atoms in R is preferably 2 to 29, and more preferably 9 to 23.

Examples of the alkyl group and alkenyl group include a methyl group, an ethyl group, an isobutyl group, a t-butyl group, and a vinyl group.

Examples of compound (α) (carboxylic acid-type hydrocarbon surfactant) include butylic acid, valeric acid, caproic acid, enanthic acid, caprylic acid, pelargonic acid, capric acid, lauric acid, myristic acid, pentadecylic acid, palmitic acid, palmitoleic acid, margaric acid, stearic acid, oleic acid, vaccenic acid, linoleic acid, (9,12,15)-linolenic acid, (6,9,12)linolenic acid, eleostearic acid, arachidic acid, 8,11-eicosadienoic acid, mead acid, arachidonic acid, behenic acid, lignoceric acid, nervonic acid, cerotic acid, montanic acid, melissic acid, crotonic acid, myristoleic acid, palmitoleic acid, sapienoic acid, oleic acid, elaidic acid, vaccenic acid, gadoleic acid, eicosenoic acid, erucic acid, nervonic acid, linoleic acid, eicosadienoic acid, docosadienoic acid, linolenic acid, pinolenic acid, α-eleostearic acid, β-eleostearic acid, mead acid, dihomo-γ-linolenic acid, eicosatrienoic acid, stearidonic acid, arachidonic acid, eicosatetraenoic acid, adrenic acid, boseopentaenoic acid, eicosapentaenoic acid, osbond acid, sardine acid, tetracosapentaenoic acid, docosahexaenoic acid, nisinic acid, and salts thereof.

Particularly, preferred is at least one selected from the group consisting of lauric acid, capric acid, myristic acid, pentadecylic acid, palmitic acid, and salts thereof.

Examples of the salts include, but are not limited to, those in which hydrogen of the carboxyl group is a metal atom, $NR^{101}_4$, imidazolium optionally having a substituent, pyridinium optionally having a substituent, or phosphonium optionally having a substituent as M in the formula described above.

The compound (α) (carboxylic acid-type hydrocarbon surfactant) is preferably at least one selected from the group consisting of lauric acid, capric acid, myristic acid, pentadecylic acid, palmitic acid, and salts thereof, still more preferably lauric acid and salts thereof, particularly preferably lauric acid salts, and most preferably sodium laurate and ammonium laurate, because particles having a small average primary particle size can be obtained by polymerization, a large number of particles can be generated during polymerization to efficiently produce the fluorine-containing polymer.

Preferred examples of the hydrocarbon surfactant include a surfactant represented by the following general formula (1):

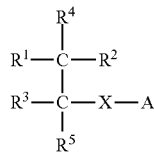

wherein $R^1$ to $R^5$ each represent H or a monovalent substituent, with the proviso that at least one of $R^1$ and $R^3$ represents a group represented by the general formula: —Y—$R^6$ and at least one of $R^2$ and $R^5$ represents a group represented by the general formula: —X-A or a group represented by the general formula: —Y—$R^6$;

X is the same or different at each occurrence and represents a divalent linking group or a bond;

A is the same or different at each occurrence and represents —COOM, —$SO_3M$, or —$OSO_3M$, wherein M is H, a metal atom, $NR^7_4$, imidazolium optionally having a substituent, pyridinium optionally having a substituent, or phosphonium optionally having a substituent, wherein $R^7$ is H or an organic group;

Y is the same or different at each occurrence and represents a divalent linking group selected from the group consisting of —$S(=O)_2$—, —O—, —COO—, —OCO—, —$CONR^8$—, and —$NR^8CO$—, or a bond, wherein $R^8$ is H or an organic group;

$R^6$ is the same or different at each occurrence and represents an alkyl group having 2 or more carbon atoms and optionally containing, between carbon atoms, at least one selected from the group consisting of a carbonyl group, an ester group, an amide group, and a sulfonyl group; and any two of $R^1$ to $R^5$ optionally bind to each other to form a ring (hereinafter also referred to as a surfactant (1)).

The surfactant (1) will be described.

In the formula, $R^1$ to $R^5$ each represent H or a monovalent substituent, with the proviso that at least one of $R^1$ and $R^3$ represents a group represented by the general formula: —Y—$R^6$ and at least one of $R^2$ and $R^3$ represents a group represented by the general formula: —X-A or a group represented by the general formula: —Y—$R^6$. Any two of $R^1$ to $R^5$ optionally bind to each other to form a ring.

The substituent which may be contained in the alkyl group for $R^1$ is preferably a halogen atom, a linear or branched alkyl group having 1 to 10 carbon atoms, or a cyclic alkyl group having 3 to 10 carbon atoms, or a hydroxy group, and particularly preferably a methyl group or an ethyl group.

The alkyl group for $R^1$ is preferably free from a carbonyl group.

In the alkyl group, 75% or less of the hydrogen atoms bonded to the carbon atoms may be replaced by halogen atoms, 50% or less thereof may be replaced by halogen atoms, or 25% or less thereof may be replaced by halogen atoms. The alkyl group is preferably a non-halogenated alkyl group free from halogen atoms such as fluorine atoms and chlorine atoms.

The alkyl group preferably contains no substituent.

$R^1$ is preferably a linear or branched alkyl group having 1 to 10 carbon atoms and optionally having a substituent or a cyclic alkyl group having 3 to 10 carbon atoms and optionally having a substituent, more preferably a linear or branched alkyl group having 1 to 10 carbon atoms and free from a carbonyl group or a cyclic alkyl group having 3 to 10 carbon atoms and free from a carbonyl group, still more preferably a linear or branched alkyl group having 1 to 10 carbon atoms and not having a substituent, further preferably a linear or branched alkyl group having 1 to 3 carbon atoms and not having a substituent, particularly preferably a methyl group (—$CH_3$) or an ethyl group (—$C_2H_5$), and most preferably a methyl group (—$CH_3$).

The monovalent substituent is preferably a group represented by the general formula: —Y—$R^6$, a group represented by the general formula: —X-A, —H, and an alkyl group having 1 to 20 carbon atoms and optionally having a substituent, —$NH_2$, —$NHR^9$ (wherein $R^9$ is an organic group), —OH, —$COOR^9$ (wherein $R^9$ is an organic group)

or —OR$^9$ (R$^9$ is an organic group). The alkyl group preferably has 1 to 10 carbon atoms.

R$^9$ is preferably an alkyl group having 1 to 10 carbon atoms or an alkylcarbonyl group having 1 to 10 carbon atoms, and more preferably an alkyl group having 1 to 4 carbon atoms or an alkylcarbonyl group having 1 to 4 carbon atoms.

In the formula, X is the same or different at each occurrence and represents a divalent linking group or a bond.

When R$^6$ does not contain none of a carbonyl group, an ester group, an amide group, and a sulfonyl group, X is preferably a divalent linking group containing at least one selected from the group consisting of a carbonyl group, an ester group, an amide group, and a sulfonyl group.

X is preferably a divalent linking group containing at least one bond selected from the group consisting of —CO—, —S(=O)$_2$—, —O—, —COO—, —OCO—, —S(=O)$_2$—O—, —O—S(=O)$_2$—, —CONR$^8$—, and —NR$^8$CO—, a C$_{1-10}$ alkylene group, or a bond. R$^8$ represents H or an organic group.

The alkyl group is preferable as the organic group in R$^8$. R$^8$ is preferably H or an organic group having 1 to 10 carbon atoms, more preferably H or an organic group having 1 to 4 carbon atoms, still more preferably H or an alkyl group having 1 to 4 carbon atoms, and still more preferably H.

In the formula, A is the same or different at each occurrence and represents —COOM, —SO$_3$M, or —OSO$_3$M, wherein M is H, a metal atom, NR$^7_4$, imidazolium optionally having a substituent, pyridinium optionally having a substituent, or phosphonium optionally having a substituent, wherein R$^7$ is H or an organic group; and the four R$^7$ may be the same as or different from each other. In a preferred embodiment, in the general formula (1), A is —COOM.

The alkyl group is preferable as the organic group in R$^7$. R$^7$ is preferably H or an organic group having 1 to 10 carbon atoms, more preferably H or an organic group having 1 to 4 carbon atoms, and still more preferably H or an alkyl group having 1 to 4 carbon atoms.

Examples of the metal atom include alkali metals (Group 1) and alkaline earth metals (Group 2), and preferred is Na, K, or Li.

M is preferably H, a metal atom, or NR$^7_4$, more preferably H, an alkali metal (Group 1), an alkaline earth metal (Group 2), or NR$^7_4$, still more preferably H, Na, K, Li, or NH$_4$, further preferably Na, K, or NH$_4$, particularly preferably Na or NH$_4$, and most preferably NH$_4$.

In the formula, Y is the same or different at each occurrence and represents a divalent linking group selected from the group consisting of —S(=O)$_2$—, —O—, —COO—, —OCO—, —CONR$^8$—, and —NR$^8$CO—, or a bond, wherein R$^8$ represents H or an organic group.

Y is preferably a divalent linking group selected from the group consisting of a bond, —O—, —COO—, —OCO—, —CONR$^8$—, and —NR$^8$CO—, more preferably a divalent linking group selected from the group consisting of a bond, —COO—, and —OCO—.

The alkyl group is preferable as the organic group in R$^8$. R$^8$ is preferably H or an organic group having 1 to 10 carbon atoms, more preferably H or an organic group having 1 to 4 carbon atoms, still more preferably H or an alkyl group having 1 to 4 carbon atoms, and still more preferably H.

In the formula, R$^6$ is the same or different at each occurrence and represents an alkyl group having 2 or more carbon atoms and optionally containing, between carbon atoms, at least one selected from the group consisting of a carbonyl group, an ester group, an amide group, and a sulfonyl group. The organic group represented by R$^6$ preferably has 2 to 20 carbon atoms, more preferably 2 to 10 carbon atoms.

The alkyl group for R$^6$ optionally contains, between carbon atoms, one or two or more of at least one selected from the group consisting of a carbonyl group, an ester group, an amide group, and a sulfonyl group, but the alkyl group contains no such groups at ends. In the alkyl group for R$^6$, 75% or less of the hydrogen atoms bonded to the carbon atoms may be replaced by halogen atoms, 50% or less thereof may be replaced by halogen atoms, or 25% or less thereof may be replaced by halogen atoms. The alkyl group is preferably a non-halogenated alkyl group free from halogen atoms such as fluorine atoms and chlorine atoms.

R$^6$ is preferably a group represented by the general formula: —R$^{10}$—CO—R$^{11}$, a group represented by the general formula: —R$^{10}$—COO—R$^{11}$, a group represented by the general formula: —R$^{11}$, a group represented by the general formula: —R$^{10}$—NR$^8$CO—R$^{11}$, or a group represented by the general formula: —R$^{10}$—CONR$^8$—R$^{11}$, wherein R$^8$ is H or an organic group; R$^{10}$ is an alkylene group; and R$^{11}$ is an alkyl group optionally having a substituent.

R$^6$ is more preferably a group represented by the general formula: —R$^{10}$—CO—R$^{11}$.

The alkyl group is preferable as the organic group in R$^8$. R$^8$ is preferably H or an organic group having 1 to 10 carbon atoms, more preferably H or an organic group having 1 to 4 carbon atoms, still more preferably H or an alkyl group having 1 to 4 carbon atoms, and still more preferably H.

The alkylene group for R$^{10}$ preferably has 1 or more, and more preferably 3 or more carbon atoms, and preferably 20 or less, more preferably 12 or less, still more preferably 10 or less, and particularly preferably 8 or less carbon atoms. Further, the alkylene group for R$^{10}$ preferably has 1 to 20, more preferably 1 to 10, and still more preferably 3 to 10 carbon atoms.

The alkyl group for R$^{11}$ may have 1 to 20 carbon atoms, and preferably has 1 to 15, more preferably 1 to 12, still more preferably 1 to 10, further preferably 1 to 8, still further preferably 1 to 6, still much more preferably 1 to 3, particularly preferably 1 or 2, and most preferably 1 carbon atom. The alkyl group for R$^{11}$ preferably consists only of primary carbons, secondary carbons, and tertiary carbons, and particularly preferably consists only of primary carbons and secondary carbons. In other words, R$^{11}$ is preferably a methyl group, an ethyl group, an n-propyl group, or an isopropyl group, and most preferably a methyl group.

In a preferred embodiment, in the general formula (1), at least one of R$^2$ and R$^5$ is a group represented by the general formula: —X-A, and A is —COOM.

The surfactant (1) is preferably a compound represented by the following general formula (1-1), a compound represented by the following general formula (1-2), or a compound represented by the following general formula (1-3), more preferably a compound represented by the general formula (1-1) or a compound represented by the general formula (1-2):

General Formula (1-1):

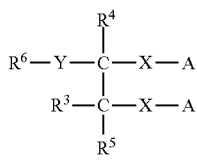

(wherein $R^3$ to $R^6$, X, A, and Y are defined as described above).

General Formula (1-2):

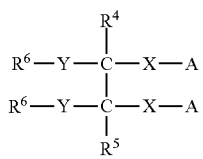

(wherein $R^4$ to $R^6$, X, A, and Y are defined as described above).

General Formula (1-3):

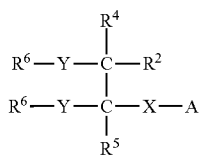

(wherein $R^4$ to $R^6$, X, A, and Y are defined as described above).

The group represented by the general formula: —X-A is preferably
- —COOM,
- —$R^{12}$COOM,
- —$SO_3$M,
- —$OSO_3$M,
- —$R^{12}SO_3$M,
- —$R^{12}OSO_3$M,
- —OCO—$R^{12}$—COOM,
- —OCO—$R^{12}$—$SO_3$M,
- —OCO—$R^{12}$—$OSO_3$M
- —COO—$R^{12}$—COOM,
- —COO—$R^{12}$—$SO_3$M,
- —COO—$R^{12}$—$OSO_3$M,
- —$CONR^8$—$R^{12}$—COOM,
- —$CONR^8$—$R^{12}$—$SO_3$M,
- —$CONR^8$—$R^{12}$—$OSO_3$M,
- —$NR^8CO$—$R^{12}$—COOM,
- —$NR^8CO$—$R^{12}$—$SO_3$M,
- —$NR^8CO$—$R^{12}$—$OSO_3$M,
- —OS(=O)$_2$—$R^{12}$—COOM,
- —OS(=O)$_2$—$R^{12}$—$SO_3$M, or
- —OS(=O)$_2$—$R^{12}$—$OSO_3$M (wherein $R^8$ and M are defined as described above; and $R^{12}$ is an alkylene group having 1 to 10 carbon atoms).

In the alkylene group for $R^{12}$, 75% or less of the hydrogen atoms bonded to the carbon atoms may be replaced by halogen atoms, 50% or less thereof may be replaced by halogen atoms, or 25% or less thereof may be replaced by halogen atoms. The alkylene group is preferably a non-halogenated alkylene group free of halogen atoms such as fluorine atoms and chlorine atoms.

The group represented by the general formula: —Y—$R^6$ is preferably
- a group represented by the general formula: —$R^{10}$—CO—$R^{11}$,
- a group represented by the general formula: —OCO—$R^{10}$—CO—$R^{11}$,
- a group represented by the general formula: —COO—$R^{10}$—CO—$R^{11}$,
- a group represented by the general formula: —OCO—$R^{10}$—COO—$R^{11}$,
- a group represented by the general formula: —COO—$R^{11}$,
- a group represented by the general formula: —$NR^8CO$—$R^{10}$—CO—$R^{11}$, or
- a group represented by the general formula: —$CONR^8$—$R^{10}$—$NR^8CO$—$R^{11}$ (wherein $R^8$, $R^{10}$, and $R^{11}$ are as described above).

In the formula, $R^4$ and $R^5$ are each independently preferably H or an alkyl group having 1 to 4 carbon atoms. In the alkyl group for $R^4$ and $R^5$, 75% or less of the hydrogen atoms bonded to the carbon atoms may be replaced by halogen atoms, 50% or less thereof may be replaced by halogen atoms, or 25% or less thereof may be replaced by halogen atoms. The alkyl group is preferably a non-halogenated alkyl group free from halogen atoms such as fluorine atoms and chlorine atoms.

$R^3$ in the general formula (1-1) is preferably H or an alkyl group having 1 to 20 carbon atoms and optionally having a substituent, more preferably H or an alkyl group having 1 to 20 carbon atoms and having no substituent, and still more preferably H.

In the alkyl group for $R^3$, 75% or less of the hydrogen atoms bonded to the carbon atoms may be replaced by halogen atoms, 50% or less thereof may be replaced by halogen atoms, or 25% or less thereof may be replaced by halogen atoms. The alkyl group is preferably a non-halogenated alkyl group free from halogen atoms such as fluorine atoms and chlorine atoms.

$R^2$ in the general formula (1-3) is preferably H, OH, or an alkyl group having 1 to 20 carbon atoms and optionally having a substituent, more preferably H, OH, or an alkyl group having 1 to 20 carbon atoms and having no substituent, and still more preferably H or OH.

In the alkyl group for $R^2$, 75% or less of the hydrogen atoms bonded to the carbon atoms may be replaced by halogen atoms, 50% or less thereof may be replaced by halogen atoms, or 25% or less thereof may be replaced by halogen atoms. The alkyl group is preferably a non-halogenated alkyl group free from halogen atoms such as fluorine atoms and chlorine atoms.

Examples of the hydrocarbon surfactant include a surfactant represented by the following formula (1-0A):

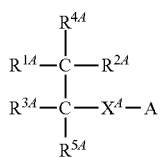

wherein $R^{1A}$ to $R^{5A}$ are H, a monovalent hydrocarbon group optionally containing, between carbon atoms, an ester group, or a group represented by general formula:

—$X^4$-A, with the proviso that at least one of $R^{2A}$ or $R^{5A}$ represents a group represented by the general formula: —$X^4$-A;

$X^4$ is the same or different at each occurrence and represents a divalent hydrocarbon group or a bond;

A is the same or different at each occurrence and represents —COOM, wherein M is H, a metal atom, $NR^7_4$, imidazolium optionally having a substituent, pyridinium optionally having a substituent, or phosphonium optionally having a substituent, wherein $R^7$ is H or an organic group; and any two of $R^{1A}$ to $R^{5A}$ may be bonded to each other to form a ring.

In the general formula (1-0A), in $R^{1A}$ to $R^{5A}$, the monovalent hydrocarbon group optionally containing, between carbon atoms, an ester group preferably has 1 to 50 carbon atoms, and more preferably 5 to 20 carbon atoms. Any two of $R^{1A}$ to $R^{5A}$ optionally bind to each other to form a ring. The monovalent hydrocarbon group optionally containing, between carbon atoms, an ester group is preferably an alkyl group.

In the formula, in $X^4$, the number of carbon atoms in the divalent hydrocarbon group is 1 to 50, and more preferably 5 to 20. Examples of the divalent hydrocarbon group include an alkylene group and an alkanediyl group, and preferred is an alkylene group.

In the general formula (1-0A), any one of $R^{2A}$ and $R^{5A}$ is preferably a group represented by the formula: —$X^4$-A, and more preferably, $R^{2A}$ is a group represented by the formula: —$X^4$-A.

In a preferred embodiment, in the general formula (1-0A), $R^{2A}$ is a group represented by the general formula: —$X^4$-A, and $R^{1A}$, $R^{3A}$, $R^{4A}$ and $R^{5A}$ are H. In this case, $X^4$ is preferably a bond or an alkylene group having 1 to 5 carbon atoms.

Another preferred embodiment is an embodiment in which in general formula (1-0A), $R^{2A}$ is a group represented by general formula: —$X^4$-A, $R^{1A}$ and $R^{3A}$ are groups represented by —$Y^4$—$R^6$, $Y^4$ is the same or different at each occurrence, and is —COO—, —OCO—, or a bond, and $R^6$ is the same or different at each occurrence, and is an alkyl group having 2 or more carbon atoms. In this case, it is preferable that $R^{4A}$ and $R^{5A}$ are H.

Examples of the hydrocarbon surfactant represented by the general formula (1-0A) include glutaric acid or a salt thereof, adipic acid or a salt thereof, pimelic acid or a salt thereof, suberic acid or a salt thereof, azelaic acid or a salt thereof, and sebacic acid or a salt thereof.

The aliphatic carboxylic acid-type hydrocarbon surfactant represented by the general formula (1-0A) may be a 2-chain 2-hydrophilic type synthetic surfactant, and examples of the gemini type surfactant include geminiserf (CHUKYO YUSHI CO., LTD.), Gemsurf α142 (carbon number: 12, lauryl group), Gemsurf α102 (carbon number: 10), and Gemsurf α182 (carbon number: 14).

The surfactant (1) may suitably be produced by a production method including:

a step (11) of reacting a carboxylic acid represented by the formula: $R^6$—COOH (wherein $R^6$ is defined as described above) and a halogenating agent to provide a carboxylic acid halide represented by the formula: $R^6$—COZ (wherein $R^6$ is as described above; and Z is a halogen atom); and a step (12) of reacting the carboxylic acid halide and a compound represented by the formula:

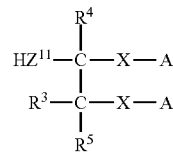

(wherein $R^3$ to $R^5$, X and A are defined as described above; and $Z^{11}$ is —$CH_2O$—, —O—, or —NH—) to provide a compound (12) represented by the formula:

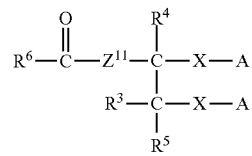

(wherein $R^3$ to $R^6$, X, A, and $Z^{11}$ n are defined as described above).

$R^3$ in the formula of the acid compound is preferably a group represented by the general formula: —$Z^{11}$H (wherein $Z^{11}$ is defined as described above) or —H. When $R^3$ is a group represented by the general formula: —$Z^{11}$H, the group reacts with the carboxylic acid halide in the step (12) to form a group represented by the general formula: —$Z^{11}$—CO—$R^6$ (wherein $R^6$ and $Z^{11}$ are defined as described above).

Examples of the halogenating agent used in the step (11) include oxalyl chloride, thionyl chloride, diethylaminosulfur trifluoride (DAST), Deoxo-Fluor (deoxofluor), and 1,1,2,2-terafluoro-N,N-dimethyllylamine (TFEDM).

Z is preferably F or Cl, and more preferably Cl.

Regarding the reaction ratio between the carboxylic acid and the halogenating agent in the step (11), the halogenating agent is preferably used in an amount of 0.6 to 5.0 mol, and more preferably 0.8 to 2.0 mol, based on 1 mol of the carboxylic acid in consideration of the improvement of the yield and the reduction of the waste. Further, it is preferably 0.5 to 10 mol, more preferably 0.6 to 5.0 mol.

The reaction in the step (11) may be performed in a solvent. Examples of the solvent include esters, ketones, aromatic hydrocarbons, ethers, nitrogen-containing polar organic compounds, halogenated hydrocarbons, nitriles, pyridines, or mixtures thereof.

Examples of the esters include ethyl acetate, butyl acetate, ethylene glycol monomethyl ether acetate, and propylene glycol monomethyl ether acetate (PGMEA, also known as 1-methoxy-2-acetoxypropane), of which ethyl acetate is preferred.

Examples of the ketones include acetone, methyl ethyl ketone, methyl isobutyl ketone, cyclohexanone, and diacetone alcohol, of which acetone is preferred.

Examples of the aromatic hydrocarbon include benzene, toluene, and xylene, of which benzene and toluene are preferred.

Examples of the ether include diethyl ether, tetrahydrofuran, dioxane, and diethylene glycol diethyl ether, of which diethyl ether and tetrahydrofuran are preferred.

Examples of the nitrogen-containing polar organic compound include N,N-dimethylformamide, N,N-dimethylacetamide, N-methyl-2-pyrrolidone, 2-pyrrolidone, and 1,3-dimethyl-2-imidazolidinone, of which N,N-dimethylformamide, N,N-dimethylacetamide, and N-methyl-2-pyrrolidone are preferred.

Examples of the halogenated hydrocarbon include dichloromethane, dichloroethane, chloroform, chlorobenzene, and o-dichlorobenzene, of which dichloromethane and chloroform are preferred.

Examples of the nitrile include acetonitrile, propionitrile, butyronitrile, isobutyronitrile, and benzonitrile, of which acetonitrile is preferred.

The reaction temperature in the step (11) is preferably 0 to 150° C., and more preferably 20 to 100° C. The reaction temperature is also preferably −78 to 150° C., and more preferably 0 to 100° C.

The reaction pressure in the step (11) is preferably 0 to 5 MPa, and more preferably 0.1 to 1.0 MPa.

The reaction duration in the step (11) is preferably 0.1 to 72 hours, and more preferably 0.1 to 48 hours.

Regarding the reaction ratio between the carboxylic acid halide and the acid compound in the step (12), the amount of the acid compound is preferably 0.5 to 10 mol, more preferably 0.6 to 5.0 mol, still more preferably 0.8 to 2.0 mol, based on 1 mol of the carboxylic acid halide in consideration of the improvement of the yield and the reduction of the waste.

The reaction in the step (12) is preferably performed in the presence of an acid. Examples of the acid include sulfuric acid, methanesulfonic acid, and p-toluene sulfone, of which sulfuric acid is preferred.

The amount of the acid used in the step (12) is preferably 0.00001 to 1.0 mol, more preferably 0.0001 to 1.0 mol, still more preferably 0.00005 to 0.1 mol, and particularly preferably 0.001 to 0.1 mol, based on 1 mol of the carboxylic acid halide in consideration of the improvement of the yield and the reduction of the waste.

The reaction temperature in the step (12) is preferably 0 to 150° C., and more preferably 20 to 100° C.

The reaction pressure in the step (12) is preferably 0 to 5 MPa, and more preferably 0.1 to 1.0 MPa.

The reaction duration in the step (12) is preferably 0.1 to 72 hours, and more preferably 0.1 to 48 hours.

The surfactant (1) may also suitably be produced by a production method including:
 a step (21) of reacting a compound (20) represented by the formula:

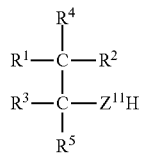

(wherein $R^1$ to $R^5$ are defined as described above; and $Z^{11}$ is —$CH_2O$—, —O—, or —NH—) and an acid anhydride represented by the formula:

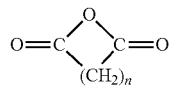

(wherein n is an integer of 1 to 5) to provide a compound (21) represented by the formula:

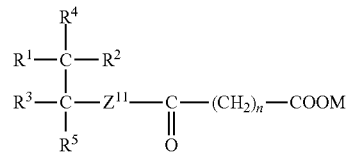

(wherein $R^1$ to $R^5$, $Z^{11}$, M, and n are defined as described above).

$R^2$ in the formula of compound (20) is preferably a group represented by the general formula: —$Z^{11}$H (wherein $Z^{11}$ is defined as described above) or —H. When $R^2$ is a group represented by the general formula: —$Z^{11}$H, the group reacts with the acid anhydride in the step (21) to form a group represented by the general formula: —$Z^{11}$—CO—$(CH_2)_n$—COOM (wherein $Z^{11}$, M, and n are defined as described above). The compound (20) may be a hydrochloride salt, a sulfate salt or the like as long as it contains the structure represented by the above formula.

Regarding the reaction ratio between the compound (20) and the acid anhydride in the step (21), the amount of the acid anhydride is preferably 0.5 to 10 mol, more preferably 0.6 to 5.0 mol, still more preferably 1.2 to 10 mol, and particularly preferably 1.6 to 4.0 mol, based on 1 mol of the compound (20) in consideration of the improvement of the yield and the reduction of the waste.

The reaction in the step (21) may be performed in the presence of a base.

Examples of the base include amines, potassium hydroxide, sodium hydroxide, and potassium carbonate.

Examples of the amines include tertiary amines such as trimethylamine, triethylamine, tributylamine, N,N-dimethylaniline, dimethylbenzylamine, and N,N,N',N'-tetramethyl-1,8-naphthalenediamine, heteroaromatic amines such as pyridine, pyrrole, uracil, collidine, and lutidine, and cyclic amines such as 1,8-diaza-bicyclo[5.4.0]-7-undecene and 1,5-diaza-bicyclo[4.3.0]-5-nonene, and pyridine or triethylamine is preferred.

The reaction temperature in the step (21) is preferably 0 to 150° C., and more preferably 20 to 80° C. The reaction temperature is also preferably −78 to 150° C., and more preferably 0 to 100° C.

The reaction pressure in the step (21) is preferably 0 to 5 MPa, and more preferably 0.1 to 1 MPa.

The reaction duration in the step (21) is preferably 0.1 to 72 hours, and more preferably 0.1 to 48 hours.

The surfactant (1) may also suitably be produced by a production method including:
 a step (31) of reacting a tartaric acid ester represented by the formula:

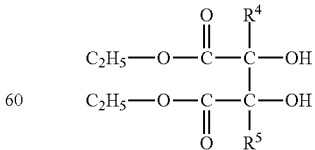

(wherein $R^4$ and $R^5$ are defined as described above) and an amine represented by the formula: $R^6R^8$—NH (wherein $R^6$ and $R^8$ are defined as described above) to provide a compound (31) represented by the formula:

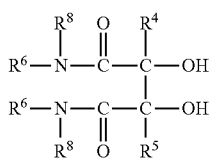

(wherein $R^4$ to $R^6$ and $R^8$ are defined as described above); and a step (32) of reacting the compound (31) and a chlorosulfonic acid represented by the formula:

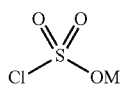

(wherein M is defined as described above) to provide a compound (32) represented by the formula:

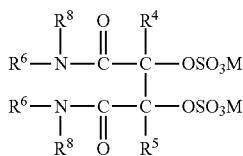

(wherein $R^4$ to $R^6$, $R^8$, and M are defined as described above).

Regarding the reaction ratio between the tartaric acid ester and the amine in the step (31), the amount of the amine is preferably 0.5 to 10 mol, more preferably 0.6 to 5.0 mol, still more preferably 1.2 to 5 mol, and particularly preferably 1.6 to 5.0 mol, based on 1 mol of the tartaric acid ester in consideration of the improvement of the yield and the reduction of the waste.

The reaction in the step (31) may be performed in a solvent. The solvent is preferably an organic solvent, and still more preferably an alcohol, an ether, a halogenated hydrocarbon, a nitrogen-containing polar organic compound or a nitrile.

Examples of the alcohol include methanol, ethanol, 1-propanol, and isopropanol.

Examples of the ether include tetrahydrofuran, dioxane, and diethylene glycol diethyl ether.

Examples of the halogenated hydrocarbon include dichloromethane, dichloroethane, chloroform, chlorobenzene, and o-dichlorobenzene.

Examples of the nitrogen-containing polar organic compound include N,N-dimethylformamide, N,N-dimethylacetamide, N-methyl-2-pyrrolidone, 2-pyrrolidone, and 1,3-dimethyl-2-imidazolidinone, of which N,N-dimethylformamide, N,N-dimethylacetamide, and N-methyl-2-pyrrolidone are preferred.

Examples of the nitrile include acetonitrile, propionitrile, butyronitrile, isobutyronitrile, and benzonitrile.

The reaction temperature in the step (31) is preferably 0 to 150° C., and more preferably 20 to 100° C.

The reaction pressure in the step (31) is preferably 0 to 5 MPa, and more preferably 0.1 to 1 MPa.

The reaction duration in the step (31) is preferably 0.1 to 72 hours, and more preferably 0.1 to 48 hours.

Regarding the reaction ratio between the compound (31) and the chlorosulfonic acid in the step (32), the amount of the chlorosulfonic acid is preferably 1.0 to 50 mol, and more preferably 1.6 to 20 mol, based on 1 mol of the compound (31) in consideration of the improvement of the yield and the reduction of the waste.

The reaction in the step (32) is preferably performed in the presence of a base. Examples of the base include alkali metal hydroxides, alkaline earth metal hydroxides, and amines, of which amines are preferred.

Examples of the amines in the step (32) include tertiary amines such as trimethylamine, triethylamine, tributylamine, N,N-dimethylaniline, dimethylbenzylamine, and N,N,N',N'-tetramethyl-1,8-naphthalenediamine, heteroaromatic amines such as pyridine, pyrrole, uracil, collidine, and lutidine, and cyclic amines such as 1,8-diaza-bicyclo[5.4.0]-7-undecene and 1,5-diaza-bicyclo[4.3.0]-5-nonene. Of these, triethylamine is preferred.

The amount of the base used in the step (32) is preferably 0.1 to 50 mol, and more preferably 1.0 to 20 mol, based on 1 mol of the compound (31) in consideration of the improvement of the yield and the reduction of the waste.

The reaction in the step (32) may be performed in a solvent. The solvent is preferably an organic solvent, more preferably an aprotic polar solvent, and still more preferably a nitrile, a halogenated hydrocarbon, dimethyl sulfoxide, sulfolane, a nitrogen-containing polar organic compound or an ether.

Examples of the nitrile include acetonitrile, propionitrile, butyronitrile, isobutyronitrile, and benzonitrile, of which acetonitrile is preferred.

Examples of the halogenated hydrocarbon include dichloromethane, dichloroethane, chloroform, chlorobenzene, and o-dichlorobenzene, of which dichloromethane and chloroform are preferred.

Examples of the nitrogen-containing polar organic compound include N,N-dimethylformamide, N,N-dimethylacetamide, N-methyl-2-pyrrolidone, 2-pyrrolidone, and 1,3-dimethyl-2-imidazolidinone, of which N,N-dimethylformamide, N,N-dimethylacetamide, and N-methyl-2-pyrrolidone are preferred.

Examples of the ether include diethyl ether, tetrahydrofuran, dioxane, and diethylene glycol diethyl ether, of which diethyl ether is preferred.

The reaction temperature in the step (32) is preferably −78 to 150° C., more preferably −78 to 100° C., still more preferably −20 to 100° C., and particularly preferably 10 to 50° C.

The reaction pressure in the step (32) is preferably 0 to 5 MPa, and more preferably 0.1 to 1.0 MPa.

The reaction duration in the step (32) is preferably 0.1 to 72 hours, and more preferably 0.1 to 48 hours.

The surfactant (1) may also suitably be produced by a production method including:

a step (41) of reacting an alcohol represented by the formula:

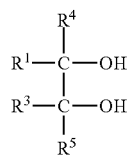

(wherein $R^1$ and $R^3$ to $R^5$ are defined as described above) and an acid anhydride represented by the formula:

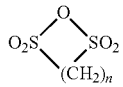

(wherein n is an integer of 1 to 5) to provide a compound (41) represented by the formula:

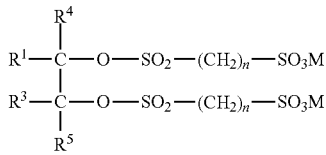

(wherein $R^1$, $R^3$ to $R^5$, $R^8$, M, and n are defined as described above).

Regarding the reaction ratio between the alcohol and the acid anhydride in the step (41), the amount of the acid anhydride is preferably 0.5 to 10 mol, more preferably 0.6 to 4.0 mol, still more preferably 1.2 to 4.0 mol, and particularly preferably 1.6 to 4.0 mol, based on 1 mol of the alcohol in consideration of the improvement of the yield and the reduction of the waste.

The reaction in the step (41) may be performed in the presence of a base.

Examples of the base include amines, potassium hydroxide, sodium hydroxide, and potassium carbonate.

Examples of the amines include tertiary amines such as trimethylamine, triethylamine, tributylamine, N,N-dimethylaniline, dimethylbenzylamine, and N,N,N',N'-tetramethyl-1,8-naphthalenediamine, heteroaromatic amines such as pyridine, pyrrole, uracil, collidine, and lutidine, and cyclic amines such as 1,8-diaza-bicyclo[5.4.0]-7-undecene and 1,5-diaza-bicyclo[4.3.0]-5-nonene, and pyridine or triethylamine is preferred.

The reaction temperature in the step (41) is preferably −78 to 150° C., more preferably 0 to 150° C., still more preferably 0 to 100° C., and particularly preferably 20 to 80° C.

The reaction pressure in the step (41) is preferably 0 to 5 MPa, and more preferably 0.1 to 1 MPa.

The reaction duration in the step (41) is preferably 0.1 to 72 hours, and more preferably 0.1 to 48 hours.

The surfactant (1) may also suitably be produced by a production method including:

a step (31) of reacting a tartaric acid ester represented by the formula:

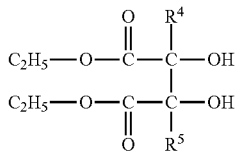

(wherein $R^4$ and $R^5$ are defined as described above) and an amine represented by the formula: $R^6R^8$—NH (wherein $R^6$ and $R^8$ are defined as described above) to provide a compound (31) represented by the formula:

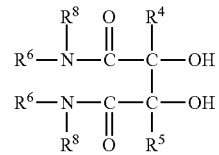

(wherein $R^4$ to $R^6$ and $R^8$ are defined as described above); and a step (51) of reacting the compound (31) and an acid anhydride represented by the formula:

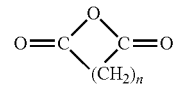

(wherein n is an integer of 1 to 5) to provide a compound (51) represented by the formula:

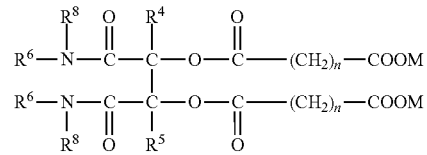

(wherein $R^4$ to $R^6$, $R^8$, M, and n are defined as described above).

Regarding the reaction ratio between the compound (31) and the acid anhydride in the step (51), the amount of the acid anhydride is preferably 0.5 to 10 mol, more preferably 0.6 to 4.0 mol, still more preferably 1.2 to 4.0 mol, and particularly preferably 1.6 to 4.0 mol, based on 1 mol of the compound (31) in consideration of the improvement of the yield and the reduction of the waste.

The reaction in the step (51) may be performed in the presence of a base.

Examples of the base include amines, potassium hydroxide, sodium hydroxide, and potassium carbonate.

Examples of the amines include tertiary amines such as trimethylamine, triethylamine, tributylamine, N,N-dimethylaniline, dimethylbenzylamine, and N,N,N',N'-tetramethyl-1,8-naphthalenediamine, heteroaromatic amines such as pyridine, pyrrole, uracil, collidine, and lutidine, and cyclic amines such as 1,8-diaza-bicyclo[5.4.0]-7-undecene and 1,5-diaza-bicyclo[4.3.0]-5-nonene, and pyridine or triethylamine is preferred.

The reaction temperature in the step (51) is preferably −78 to 150° C., more preferably 0 to 150° C., still more preferably 0 to 100° C., and particularly preferably 20 to 80° C.

The reaction pressure in the step (51) is preferably 0 to 5 MPa, and more preferably 0.1 to 1 MPa.

The reaction duration in the step (51) is preferably 0.1 to 72 hours, and more preferably 0.1 to 48 hours.

The surfactant (1) may also suitably be produced by a production method including:

a step (61) of reacting an alcohol represented by the formula: $R^6$—OH (wherein $R^6$ is defined as described above) and a fumaric acid halide to provide a compound (61) represented by the formula:

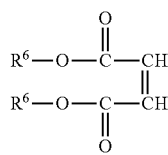

(wherein $R^6$ is defined as described above); and
a step (62) of reacting the compound (61) and a sulfooxidant such as sodium hydrogen sulfite to provide a compound (62) represented by the formula:

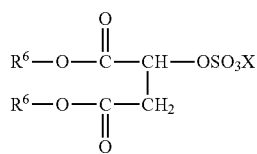

(wherein $R^6$ and X are defined as described above).

Examples of the fumaric acid halide used in the step (61) include fumalyl chloride, fumalyl fluoride, and fumalyl bromide.

Regarding the reaction ratio between the alcohol and the fumaric acid halide in the step (61), the amount of the fumaric acid halide is preferably 0.1 to 10 mol, more preferably 0.1 to 2.0 mol, still more preferably 0.1 to 2.0 mol, and particularly preferably 0.2 to 0.7 mol, based on 1 mol of the alcohol in consideration of the improvement of the yield and the reduction of the waste.

The reaction in the step (61) may be performed in a solvent. Examples of the solvent include esters, ketones, aromatic hydrocarbons, ethers, nitrogen-containing polar organic compounds, halogenated hydrocarbons, nitriles, pyridines, or mixtures thereof.

Examples of the esters include ethyl acetate, butyl acetate, ethylene glycol monomethyl ether acetate, and propylene glycol monomethyl ether acetate (PGMEA, also known as 1-methoxy-2-acetoxypropane), of which ethyl acetate is preferred.

Examples of the ketones include acetone, methyl ethyl ketone, methyl isobutyl ketone, cyclohexanone, and diacetone alcohol, of which acetone is preferred.

Examples of the aromatic hydrocarbon include benzene, toluene, and xylene, of which benzene and toluene are preferred.

Examples of the ether include diethyl ether, tetrahydrofuran, dioxane, and diethylene glycol diethyl ether, of which diethyl ether and tetrahydrofuran are preferred.

Examples of the nitrogen-containing polar organic compound include N,N-dimethylformamide, N,N-dimethylacetamide, N-methyl-2-pyrrolidone, 2-pyrrolidone, and 1,3-dimethyl-2-imidazolidinone, of which N,N-dimethylformamide, N,N-dimethylacetamide, and N-methyl-2-pyrrolidone are preferred.

Examples of the halogenated hydrocarbon include dichloromethane, dichloroethane, chloroform, chlorobenzene, and o-dichlorobenzene, of which dichloromethane and chloroform are preferred.

Examples of the nitrile include acetonitrile, propionitrile, butyronitrile, isobutyronitrile, and benzonitrile, of which acetonitrile is preferred.

The reaction temperature in the step (61) is preferably −78 to 200° C., and more preferably −20 to 150° C.

The reaction pressure in the step (61) is preferably 0 to 5.0 MPa, and more preferably 0.1 to 1.0 MPa.

The reaction duration in the step (61) is preferably 0.1 to 72 hours, and more preferably 0.1 to 48 hours.

In the step (62), the compound (62) is produced by an addition reaction between the compound (61) having a double bond and a sulfonate agent such as sodium hydrogen sulfite.

Regarding the reaction ratio between the compound (61) and the sulfonate agent in the step (62), the amount of the sulfonate agent is preferably 0.5 to 20.0 mol, more preferably 0.6 to 10.0 mol, still more preferably 0.8 to 10.0 mol, and particularly preferably 1.2 to 10.0 mol, based on 1 mol of the compound (61) in consideration of the improvement of the yield and the reduction of the waste.

The reaction in the step (62) may be performed in a solvent. The solvent is preferably a water-soluble solvent, and examples thereof include water, alcohols, ethers, and nitriles.

Examples of the alcohol include methanol, ethanol, 1-propanol, and isopropanol.

Examples of the ether include tetrahydrofuran, dioxane, and diethylene glycol diethyl ether.

Examples of the nitrile include acetonitrile, propionitrile, butyronitrile, isobutyronitrile, and benzonitrile, of which acetonitrile is preferred.

The reaction temperature in the step (62) is preferably −78 to 200° C., and more preferably −20 to 150° C.

The reaction pressure in the step (62) is preferably 0 to 5.0 MPa, and more preferably 0.1 to 1.0 MPa.

The reaction duration in the step (62) is preferably 0.1 to 72 hours, and more preferably 0.1 to 48 hours.

The surfactant (1) may also suitably be produced by a production method including:
a step (71) of sulfuric-esterifying a compound (70) represented by the

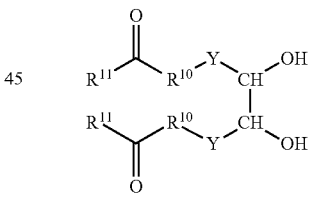

(wherein $R^{10}$, $R^{11}$, and Y are defined as described above) to provide a compound (71) represented by the formula:

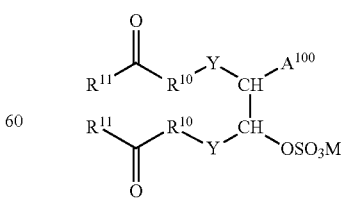

(wherein $R^{10}$, $R^{11}$, and Y are defined as described above; $A^{100}$ is —OH or —$OSO_3M$; and M is defined as described above).

The sulfuric-esterification in the step (71) may be performed by reacting the compound (70) and a sulfating reagent. Examples of the sulfating reagent include sulfur trioxide amine complexes such as a sulfur trioxide pyridine complex, a sulfur trioxide trimethylamine complex, and a sulfur trioxide triethylamine complex, sulfur trioxide amide complexes such as a sulfur trioxide dimethylformamide complex, sulfuric acid-dicyclohexylcarbodiimide, chlorosulfuric acid, concentrated sulfuric acid, and sulfamic acid. The amount of the sulfating reagent used is preferably 0.5 to 10 mol, more preferably 0.5 to 5 mol, and still more preferably 0.7 to 4 mol, based on 1 mol of the compound (70). By adjusting the amount of the sulfating reagent used, one or both of the two —OH groups of the compound (20) can be sulfuric-esterified.

The sulfuric-esterification in the step (71) may be performed in a solvent. The solvent is preferably an organic solvent, and examples thereof include ethers, halogenated hydrocarbons, aromatic hydrocarbons, pyridines, dimethyl sulfoxide, sulfolane, and nitriles.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

Examples of the nitrile include acetonitrile, propionitrile, butyronitrile, isobutyronitrile, and benzonitrile, of which acetonitrile is preferred.

The sulfuric-esterification temperature in the step (71) is preferably −78 to 200° C., and more preferably −20 to 150° C.

The sulfuric-esterification pressure in the step (71) is preferably 0 to 10 MPa, and more preferably 0.1 to 5 MPa.

The sulfuric-esterification duration in the step (71) is preferably 0.1 to 72 hours, and more preferably 0.1 to 48 hours.

The compound (70) may also be produced by a production method including:

a step (101) of hydroxylating a compound (100) represented by the formula:

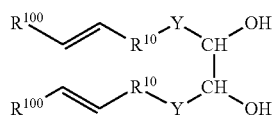

(wherein $R^{10}$ and Y are defined as described above; and $R^{100}$ is an alkyl group) to provide a compound (101) represented by the formula:

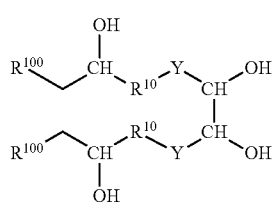

(wherein $R^{10}$, $R^{100}$, and $Y^1$ are defined as described above); and a step (102) of oxidizing the compound (101) to provide the compound (70).

The alkyl group as $R^{100}$ is $R^{100}$—$CH_2$— to constitute $R^{11}$ described above.

The hydroxylation in the step (101) may be performed by a method (1) in which iron(II) phthalocyanine (Fe(Pc)) and sodium borohydride are caused to act on the compound (100) in an oxygen atmosphere or a method (2) in which isopinocampheylborane (IpcBH$_2$) is caused to act on the compound (100) and then the resulting intermediate (dialkyl borane) is oxidized.

In the method (1), iron(II) phthalocyanine may be used in a catalytic amount, and may be used in an amount of 0.001 to 1.2 mol based on 1 mol of the compound (100).

In the method (1), sodium borohydride may be used in an amount of 0.5 to 20 mol based on 1 mol of the compound (100).

The reaction in the method (1) may be performed in a solvent. The solvent is preferably an organic solvent, and examples thereof include ethers, halogenated hydrocarbons, aromatic hydrocarbons, nitriles, and nitrogen-containing polar organic compounds.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

Examples of the nitrile include acetonitrile, propionitrile, butyronitrile, isobutyronitrile, and benzonitrile, of which acetonitrile is preferred.

Examples of the nitrogen-containing polar organic compound include N,N-dimethylformamide, N,N-dimethylacetamide, N-methyl-2-pyrrolidone, 2-pyrrolidone, and 1,3-dimethyl-2-imidazolidinone, of which N,N-dimethylformamide, N,N-dimethylacetamide, and N-methyl-2-pyrrolidone are preferred.

The reaction temperature in the method (1) is preferably −78 to 200° C., and more preferably 0 to 150° C.

The reaction pressure in the method (1) is preferably 0 to 5.0 MPa, and more preferably 0.1 to 1.0 MPa.

The reaction duration in the method (1) is preferably 0.1 to 72 hours, and more preferably 0.1 to 48 hours.

In the method (2), isopinocampheylborane may be used in an amount of 0.1 to 10.0 mol based on 1 mol of the compound (100).

The reaction of the compound (100) and isopinocampheylborane may be performed in a solvent. The solvent is preferably an organic solvent, and examples thereof include ethers, halogenated hydrocarbons, and aromatic hydrocarbons.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

The reaction temperature of the compound (100) and isopinocampheylborane is preferably −78 to 200° C., and more preferably 0 to 150° C.

The reaction pressure of the compound (100) and isopinocampheylborane is preferably 0 to 5.0 MPa, and more preferably 0.1 to 1.0 MPa.

The reaction duration of the compound (100) and isopinocampheylborane is preferably 0.1 to 72 hours, and more preferably 0.1 to 48 hours.

The oxidation in the method (2) may be performed by causing an oxidizing agent to act on the intermediate. Examples of the oxidizing agent include hydrogen peroxide. The oxidizing agent may be used in an amount of 0.7 to 10 mol based on 1 mol of the intermediate.

The oxidation in the method (2) may be performed in a solvent. Examples of the solvent include water, methanol, and ethanol, of which water is preferred.

The oxidation temperature in the method (2) is preferably −78 to 150° C., more preferably 0 to 100° C., and still more preferably 10 to 80° C.

The oxidation pressure in the method (2) is preferably 0 to 5.0 MPa, and more preferably 0.1 to 1.0 MPa.

The oxidation duration in the method (2) is preferably 0.1 to 72 hours, and more preferably 0.1 to 48 hours.

Examples of the method of oxidizing the compound (101) in the step (102) include (a) a method of using Jones reagent ($CrO_3/H_2SO_4$) (Jones oxidation), (b) a method of using Dess-Martin periodinane (DMP) (Dess-Martin oxidation), (c) a method of using pyridinium chlorochromate (PCC), (d) a method of causing a bleaching agent (about 5% to 6% aqueous solution of NaOCl) to act in the presence of a nickel compound such as $NiCl_2$, and (e) a method of causing a hydrogen acceptor such as an aldehyde or a ketone to act in the presence of an aluminum catalyst such as $Al(CH_3)_3$ or $Al[OCH(CH_3)_2]_3$ (Oppenauer oxidation).

The oxidation in the step (102) may be performed in a solvent. The solvent is preferably water or an organic solvent, and examples thereof include water, ketones, ethers, halogenated hydrocarbons, aromatic hydrocarbons, and nitriles.

Examples of the ketones include acetone, methyl ethyl ketone, methyl isobutyl ketone, cyclohexanone, and diacetone alcohol, of which acetone is preferred.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

Examples of the nitrile include acetonitrile, propionitrile, butyronitrile, isobutyronitrile, and benzonitrile, of which acetonitrile is preferred.

The oxidation temperature in the step (102) is preferably −78 to 200° C., and may appropriately be selected in accordance with the method used.

The oxidation pressure in the step (102) is preferably 0 to 5.0 MPa, and may appropriately be selected in accordance with the method used.

The oxidation duration in the step (102) is preferably 0.1 to 72 hours, and may appropriately be selected in accordance with the method used.

The compound (70) may also be produced by a production method including:

a step (201) of ozonolyzing a compound (200) represented by the formula:

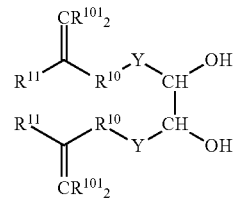

(wherein $R^{10}$, $R^{11}$, and Y are defined as described above; and $R^{101}$ is an organic group) to provide the compound (70).

$R^{101}$ is preferably an alkyl group having 1 to 20 carbon atoms. The four $R^{101}$ may be the same as or different from each other.

The ozonolysis in the step (201) may be performed by causing ozone to act on the compound (200), followed by post-treatment with a reducing agent.

The ozone may be generated by dielectric barrier discharge in oxygen gas.

Examples of the reducing agent used in the post-treatment include zinc, dimethyl sulfide, thiourea, and phosphines, of which phosphines are preferred.

The ozonolysis in the step (201) may be performed in a solvent. The solvent is preferably water or an organic solvent, and examples thereof include water, alcohols, carboxylic acids, ethers, halogenated hydrocarbons, and aromatic hydrocarbons.

Examples of the alcohol include methanol, ethanol, 1-propanol, and isopropanol. Of these, methanol and ethanol are preferred.

Examples of the carboxylic acids include acetic acid and propionic acid. Of these, acetic acid is preferred.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

The ozonolysis temperature in the step (201) is preferably −78 to 200° C., and more preferably 0 to 150° C.

The ozonolysis pressure in the step (201) is preferably 0 to 5.0 MPa, and more preferably 0.1 to 1.0 MPa.

The ozonolysis duration in the step (201) is preferably 0.1 to 72 hours, and more preferably 0.1 to 48 hours.

The compound (70) may also be produced by a production method including:

a step (301) of epoxidizing a compound (300) represented by the formula:

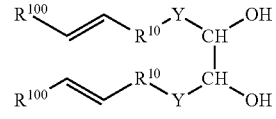

(wherein $R^{10}$ and Y are defined as described above; and $R^{100}$ is an alkyl group) to provide a compound (301) represented by the formula:

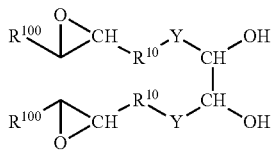

(wherein $R^{10}$, $R^{100}$, and $Y^1$ are defined as described above);

a step (302) of reacting the compound (302) with a lithium dialkylcopper represented by $R^{102}{}_2CuLi$ (wherein $R^{102}$ is an alkyl group) to provide a compound (302) represented by the formula:

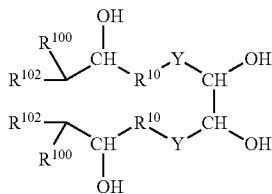

(wherein $R^{10}$, $R^{100}$, $R^{102}$, and $Y^1$ are defined as described above); and a step (303) of oxidizing the compound (302) to provide the compound (70).

The alkyl groups as $R^{100}$ and $R^{102}$ form $R^{100}R^{102}$—CH— to constitute $R^{11}$ described above.

The two $R^{100}$ may be the same as or different from each other. The two $R^{102}$ may be the same as or different from each other.

The epoxidation in the step (301) may be performed by causing an epoxidizing agent to act on the compound (300).

Examples of the epoxidizing agent include peroxy acids such as meta-chloroperbenzoic acid (m-CPBA), perbenzoic acid, hydrogen peroxide, and tert-butyl hydroperoxide, dimethyl dioxolane, and methyl trifluoromethyl dioxolane, of which peroxy acids are preferred, and meta-chloroperbenzoic acid is more preferred.

The epoxidizing agent may be used in an amount of 0.5 to 10.0 mol based on 1 mol of the compound (300).

The epoxidation in the step (301) may be performed in a solvent. The solvent is preferably an organic solvent, and examples thereof include ketones, ethers, halogenated hydrocarbons, aromatic hydrocarbons, nitriles, pyridines, nitrogen-containing polar organic compounds, and dimethyl sulfoxide, of which dichloromethane is preferred.

Examples of the ketones include acetone, methyl ethyl ketone, methyl isobutyl ketone, cyclohexanone, and diacetone alcohol, of which acetone is preferred.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

Examples of the nitrile include acetonitrile, propionitrile, butyronitrile, isobutyronitrile, and benzonitrile, of which acetonitrile is preferred.

Examples of the nitrogen-containing polar organic compound include N,N-dimethylformamide, N,N-dimethylacetamide, N-methyl-2-pyrrolidone, 2-pyrrolidone, and 1,3-dimethyl-2-imidazolidinone, of which N,N-dimethylformamide, N,N-dimethylacetamide, and N-methyl-2-pyrrolidone are preferred.

The epoxidation temperature in the step (301) is preferably −78 to 200° C., and more preferably −40 to 150° C.

The epoxidation pressure in the step (301) is preferably 0 to 5.0 MPa, and more preferably 0.1 to 1.0 MPa.

The epoxidation duration in the step (301) is preferably 0.1 to 72 hours, and more preferably 0.1 to 48 hours.

In the step (302), the lithium dialkylcopper may be used in an amount of 0.5 to 10.0 mol based on 1 mol of the compound (301).

The reaction in the step (302) may be performed in a solvent. The solvent is preferably an organic solvent, and examples thereof include ethers, halogenated hydrocarbons, and aromatic hydrocarbons.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

The reaction temperature in the step (302) is preferably −78 to 200° C., and more preferably −40 to 150° C.

The reaction pressure in the step (302) is preferably 0 to 5.0 MPa, and more preferably 0.1 to 1.0 MPa.

The reaction duration in the step (302) is preferably 0.1 to 72 hours, and more preferably 0.1 to 48 hours.

Examples of the method of oxidizing the compound (302) in the step (303) include (a) a method of using Jones reagent ($CrO_3/H_2SO_4$) (Jones oxidation), (b) a method of using Dess-Martin periodinane (DMP) (Dess-Martin oxidation), (c) a method of using pyridinium chlorochromate (PCC), (d) a method of causing a bleaching agent (about 5% to 6% aqueous solution of NaOCl) to act in the presence of a nickel compound such as $NiCl_2$, and (e) a method of causing a hydrogen acceptor such as an aldehyde or a ketone to act in the presence of an aluminum catalyst such as $Al(CH_3)_3$ or $Al[OCH(CH_3)_2]_3$ (Oppenauer oxidation).

The oxidation in the step (303) may be performed in a solvent. The solvent is preferably water or an organic solvent, and examples thereof include water, ketones, alcohols, ethers, halogenated hydrocarbons, aromatic hydrocarbons, and nitriles.

Examples of the ketones include acetone, methyl ethyl ketone, methyl isobutyl ketone, cyclohexanone, and diacetone alcohol, of which acetone is preferred.

Examples of the alcohol include methanol, ethanol, 1-propanol, and isopropanol. Of these, methanol and ethanol are preferred.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

Examples of the nitrile include acetonitrile, propionitrile, butyronitrile, isobutyronitrile, and benzonitrile, of which acetonitrile is preferred.

The oxidation temperature in the step (303) is preferably −78 to 200° C., and may appropriately be selected in accordance with the method used.

The oxidation pressure in the step (303) is preferably 0 to 5.0 MPa, and may appropriately be selected in accordance with the method used.

The oxidation duration in the step (303) is preferably 0.1 to 72 hours, and may appropriately be selected in accordance with the method used.

The compound (70) may also be produced by a production method including:
a step (401) of oxidizing a compound (400) represented by the formula:

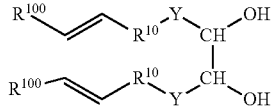

(wherein $R^{10}$ and Y are defined as described above; and $R^{101}$ is an alkyl group) to provide the compound (70).

The oxidation in the step (401) may be performed by causing an oxidizing agent to act on the compound (400) in the presence of water and a palladium compound.

Examples of the oxidizing agent include monovalent or divalent copper salts such as copper chloride, copper acetate, copper cyanide, and copper trifluoromethanethiolate, iron salts such as iron chloride, iron acetate, iron cyanide, iron trifluoromethanethiolate, and hexacyanoferrates, benzoquinones such as 1,4-benzoquinone, 2,3-dichloro-5,6-dicyano-1,4-benzoquinone, tetrachloro-1,2-benzoquinone, and tetrachloro-1,4-benzoquinone, $H_2O_2$, $MnO_2$, $KMnO_4$, $RuO_4$, m-chloroperbenzoic acid, oxygen, or combinations thereof. Of these, copper salts, iron salts, and benzoquinones are preferred, and copper chloride, iron chloride, and 1,4-benzoquinone are more preferred. The oxidizing agent may be used in an amount of 0.001 to 10 mol based on 1 mol of the compound (400).

The water may be used in an amount of 0.5 to 1,000 mol based on 1 mol of the compound (400).

An example of the palladium compound is palladium dichloride. The palladium compound may be used in a catalytic amount, and may be used in an amount of 0.0001 to 1.0 mol based on 1 mol of the compound (400).

The oxidation in the step (401) may be performed in a solvent. Examples of the solvent include water, esters, aliphatic hydrocarbons, aromatic hydrocarbons, alcohols, carboxylic acids, ethers, halogenated hydrocarbons, nitrogen-containing polar organic compounds, nitriles, dimethyl sulfoxide, and sulfolane.

Examples of the esters include ethyl acetate, butyl acetate, ethylene glycol monomethyl ether acetate, and propylene glycol monomethyl ether acetate (PGMEA, also known as 1-methoxy-2-acetoxypropane), of which ethyl acetate is preferred.

Examples of the aliphatic hydrocarbons include hexane, cyclohexane, heptane, octane, nonane, decane, undecane, dodecane, and mineral spirits, of which cyclohexane and heptane are preferred.

Examples of the aromatic hydrocarbon include benzene, toluene, and xylene, of which benzene and toluene are preferred.

Examples of the alcohol include methanol, ethanol, 1-propanol, and isopropanol.

Examples of the carboxylic acids include acetic acid and propionic acid. Of these, acetic acid is preferred.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the nitrogen-containing polar organic compound include N,N-dimethylformamide, N,N-dimethylacetamide, N-methyl-2-pyrrolidone, 2-pyrrolidone, and 1,3-dimethyl-2-imidazolidinone, of which N,N-dimethylformamide, N,N-dimethylacetamide, and N-methyl-2-pyrrolidone are preferred.

Examples of the nitrile include acetonitrile, propionitrile, butyronitrile, isobutyronitrile, and benzonitrile, of which acetonitrile is preferred.

The oxidation temperature in the step (401) is preferably −78 to 200° C., and more preferably −20 to 150° C.

The oxidation pressure in the step (401) is preferably 0 to 10 MPa, and more preferably 0.1 to 5.0 MPa.

The oxidation duration in the step (401) is preferably 0.1 to 72 hours, and more preferably 0.1 to 48 hours.

The compound (100), the compound (300), and the compound (400) may be produced by a production method including:
a step (501) of causing a reducing agent to act on an aldehyde represented by the formula:

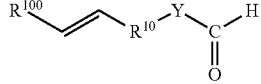

(wherein $R^{10}$ and Y are defined as described above; and $R^{101}$ is an alkyl group) to provide the compound (100).

In the step (501), reducing coupling reaction dimerizes the aldehyde to produce the compound (100), the compound (300), and the compound (400). Examples of the reducing agent used in the step (501) includes samarium diiodide, titanium dichloride, vanadium trichloride, titanium tetrachloride, bis(cyclooctadiene) nickel, copper, magnesium, zinc, sodium, cerium trichloride, chromium oxide, and triphenyltin hydride. The reducing agents may be used in combination. The amount of the reducing agent used is preferably 0.001 to 10 mol, more preferably 0.01 to 5 mol, still more preferably 0.1 to 2 mol, based on 1 mol of the aldehyde.

The reaction in the step (501) may be performed in a solvent. The solvent is preferably an organic solvent, and more preferably an ether, a halogenated hydrocarbon, pyridine, nitrile, or an aromatic hydrocarbon.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the nitrile include acetonitrile, propionitrile, butyronitrile, isobutyronitrile, and benzonitrile, of which acetonitrile is preferred.

Examples of the aromatic hydrocarbon include benzene, toluene, and xylene, of which benzene and toluene are preferred.

The reaction in step (501) is preferably performed in the presence of an alcohol. Examples of the alcohol include methanol, ethanol, and isopropanol.

The reaction temperature in the step (501) is preferably −78 to 200° C., and more preferably −20 to 100° C.

The reaction pressure in the step (501) is preferably 0 to 5.0 MPa, and more preferably 0.1 to 1.0 MPa.

The reaction duration in the step (501) is preferably 0.1 to 72 hours, and more preferably 0.1 to 48 hours.

In any of the production methods described above, after the completion of each step, the solvent may be distilled off, or distillation, purification or the like may be performed to increase the purity of the resulting compounds. For the resulting compounds in which M is H, such as those containing —COOH, —SO$_3$H, —OSO$_3$H, or the like, the compounds may be brought into contact with an alkali such as sodium carbonate or ammonia to covert these groups into the form of a salt.

Examples of the hydrocarbon surfactant also include a hydrocarbon surfactant having one or more carbonyl groups which are not in a carboxyl group.

The hydrocarbon surfactant having one or more carbonyl groups which are not in a carboxyl group is preferably a surfactant represented by the formula: R—X, wherein R is a fluorine-free organic group having one or more carbonyl groups which are not in a carboxyl group and having 1 to 2,000 carbon atoms, X is, —OSO$_3$X$^1$, —COOX$^1$, or —SO$_3$X$^1$, wherein X$^1$ is H, a metal atom, NR$^1_4$, imidazolium optionally having a substituent, pyridinium optionally having a substituent, or phosphonium optionally having a substituent, wherein R$^1$ is H or an organic group and may be the same or different. R preferably has 500 or less carbon atoms, more preferably 100 or less, still more preferably 50 or less, and further preferably 30 or less.

The hydrocarbon surfactant is more preferably at least one selected from the group consisting of a surfactant represented by the following formula (a):

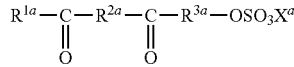

wherein R$^{1a}$ is a linear or branched alkyl group having 1 or more carbon atoms or a cyclic alkyl group having 3 or more carbon atoms, with a hydrogen atom bonded to a carbon atom therein being optionally replaced by a hydroxy group or a monovalent organic group containing an ester bond, optionally contains a carbonyl group when having 2 or more carbon atoms, and optionally contains a monovalent or divalent heterocycle or optionally forms a ring when having 3 or more carbon atoms; R$^{2a}$ and R$^{3a}$ are each independently a single bond or a divalent linking group; the total number of carbon atoms of R$^{1a}$, R$^{2a}$, and R$^{3a}$ is 6 or more; X$^a$ is H, a metal atom, NR$^{4a}_4$, imidazolium optionally having a substituent, pyridinium optionally having a substituent, or phosphonium optionally having a substituent, wherein R$^{4a}$ is H or an organic group and may be the same or different; and any two of R$^{1a}$, R$^{2a}$, and R$^{3a}$ optionally bind to each other to form a ring;

a surfactant (b) represented by the following formula (b):

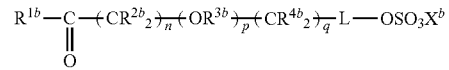

wherein R$^{1b}$ is a linear or branched alkyl group having 1 or more carbon atoms and optionally having a substituent or a cyclic alkyl group having 3 or more carbon atoms and optionally having a substituent, and optionally contains a monovalent or divalent heterocycle or optionally forms a ring when having 3 or more carbon atoms; R$^{2b}$ and R$^{4b}$ are each independently H or a substituent; R$^{3b}$ is an alkylene group having 1 to 10 carbon atoms and optionally having a substituent; n is an integer of 1 or more; p and q are each independently an integer of 0 or more; X$^b$ is H, a metal atom, NR$^{5b}_4$, imidazolium optionally having a substituent, pyridinium optionally having a substituent, or phosphonium optionally having a substituent, wherein R$^{5b}$ is H or an organic group and may be the same or different; any two of R$^{1b}$, R$^{2b}$, R$^{3b}$, and R$^{4b}$ optionally bind to each other to form a ring; L is a single bond, —CO$_2$—B—*, —OCO—B—*, —CONR$^{6b}$—B—*, —NR$^{6b}$CO—B—*, or —CO— other than the carbonyl groups in —CO$_2$—B—, —OCO—B—, —CONR$^{6b}$—B—, and —NR$^6$CO—B—, wherein B is a single bond or an alkylene group having 1 to 10 carbon atoms and optionally having a substituent, R$^{6b}$ is H or an alkyl group having 1 to 4 carbon atoms and optionally having a substituent; and * indicates the side bonded to —OSO$_3$X$^b$ in the formula;

a surfactant (c) presented by the following formula (c):

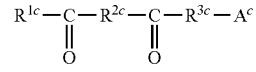

wherein R$^{1c}$ is a linear or branched alkyl group having 1 or more carbon atoms or a cyclic alkyl group having 3 or more carbon atoms, with a hydrogen atom bonded to a carbon atom therein being optionally replaced by a hydroxy group or a monovalent organic group containing an ester bond, optionally contains a carbonyl group when having 2 or more carbon atoms, and optionally contains a monovalent or divalent heterocycle or optionally forms a ring when having 3 or more carbon atoms; R$^{2c}$ and R$^{3c}$ are each independently a single bond or a divalent linking group; the total number of carbon atoms of R$^{1c}$, R$^{2c}$, and R$^{3c}$ is 5 or more; A$^c$ is —COOX$^c$ or —SO$_3$X$^c$, wherein X$^c$ is H, a metal atom, NR$^{4c}_4$, imidazolium optionally having a substituent, pyridinium optionally having a substituent, or phosphonium optionally having a substituent, wherein R$^{4c}$ is H or an organic group and may be the same or different; and any two of R$^{1c}$, R$^{2c}$, and R$^{3c}$ optionally bind to each other to form a ring; and a surfactant (d) represented by the following formula (d):

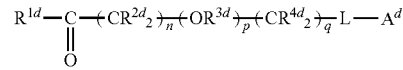

wherein $R^{1d}$ is a linear or branched alkyl group having 1 or more carbon atoms and optionally having a substituent or a cyclic alkyl group having 3 or more carbon atoms and optionally having a substituent, and optionally contains a monovalent or divalent heterocycle or optionally forms a ring when having 3 or more carbon atoms; $R^{2d}$ and $R^{4d}$ are each independently H or a substituent; $R^{3d}$ is an alkylene group having 1 to 10 carbon atoms and optionally having a substituent; n is an integer of 1 or more; p and q are each independently an integer of 0 or more; $A^d$ is —$SO_3X^d$ or —$COOX^d$, wherein $X^d$ is H, a metal atom, $NR^{5d}_4$, imidazolium optionally having a substituent, pyridinium optionally having a substituent, or phosphonium optionally having a substituent, wherein $R^{5d}$ is H or an organic group and may be the same or different; any two of $R^{1d}$, $R^{2d}$, $R^{3d}$, and $R^{4d}$ optionally bind to each other to form a ring; L is a single bond, —$CO_2$—B—*, —OCO—B—*, —$CONR^{6d}$—B—*, —$NR^{6d}CO$—B—*, or —CO— other than the carbonyl groups in —$CO_2$—B—, —OCO—B—, —$CONR^{6d}$—B—, and —$NR^{6d}CO$—B—, wherein B is a single bond or an alkylene group having 1 to 10 carbon atoms and optionally having a substituent, $R^{6d}$ is H or an alkyl group having 1 to 4 carbon atoms and optionally having a substituent; and * indicates the side bonded to $A^d$ in the formula.

The surfactant (a) is described below.

In the formula (a), $R^{1a}$ is a linear or branched alkyl group having 1 or more carbon atoms or a cyclic alkyl group having 3 or more carbon atoms.

When having 3 or more carbon atoms, the alkyl group optionally contains a carbonyl group (—C(=O)—) between two carbon atoms. When having 2 or more carbon atoms, the alkyl group optionally contains the carbonyl group at an end of the alkyl group. In other words, acyl groups such as an acetyl group represented by $CH_3$—C(=O)— are also included in the alkyl group.

When having 3 or more carbon atoms, the alkyl group optionally contains a monovalent or divalent heterocycle, or optionally forms a ring. The heterocycle is preferably an unsaturated heterocycle, more preferably an oxygen-containing unsaturated heterocycle, and examples thereof include a furan ring. In $R^{1a}$, a divalent heterocycle may be present between two carbon atoms, or a divalent heterocycle may be present at an end and bind to —C(=O)—, or a monovalent heterocycle may be present at an end of the alkyl group.

The "number of carbon atoms" in the alkyl group as used herein includes the number of carbon atoms constituting the carbonyl groups and the number of carbon atoms constituting the heterocycles. For example, the number of carbon atoms in the group represented by $CH_3$—C(=O)—$CH_2$— is 3, the number of carbon atoms in the group represented by $CH_3$—C(=O)—$C_2H_4$—C(=O)—$C_2H_4$— is 7, and the number of carbon atoms in the group represented by $CH_3$—C(=O)— is 2.

In the alkyl group, a hydrogen atom bonded to a carbon atom may be replaced by a functional group such as a hydroxy group (—OH) or a monovalent organic group containing an ester bond. Still, it is preferably not replaced by any functional group.

An example of the monovalent organic group containing an ester bond is a group represented by the formula: —O—C(=O)—$R^{101a}$, wherein $R^{101a}$ is an alkyl group.

In the alkyl group, 75% or less of the hydrogen atoms bonded to the carbon atoms may be replaced by halogen atoms, 50% or less thereof may be replaced by halogen atoms, or 25% or less thereof may be replaced by halogen atoms. The alkyl group is preferably a non-halogenated alkyl group free from halogen atoms such as fluorine atoms and chlorine atoms.

In the formula, $R^{2a}$ and $R^{3a}$ are each independently a single bond or a divalent linking group.

Preferably, $R^{2a}$ and $R^{3a}$ are each independently a single bond, or a linear or branched alkylene group having 1 or more carbon atoms, or a cyclic alkylene group having 3 or more carbon atoms.

The alkylene group constituting $R^{2a}$ and $R^{3a}$ is preferably free from a carbonyl group.

In the alkylene group, a hydrogen atom bonded to a carbon atom may be replaced by a functional group such as a hydroxy group (—OH) or a monovalent organic group containing an ester bond. Still, it is preferably not replaced by any functional group.

An example of the monovalent organic group containing an ester bond is a group represented by the formula: —O—C(=O)—$R^{102a}$, wherein $R^{102a}$ is an alkyl group.

In the alkylene group, 75% or less of the hydrogen atoms bonded to the carbon atoms may be replaced by halogen atoms, 50% or less thereof may be replaced by halogen atoms, or 25% or less thereof may be replaced by halogen atoms. The alkylene group is preferably a non-halogenated alkylene group free from halogen atoms such as fluorine atoms and chlorine atoms.

The total number of carbon atoms of $R^{1a}$, $R^{2a}$, and $R^{3a}$ is 6 or more. The total number of carbon atoms is preferably 8 or more, more preferably 9 or more, still more preferably 10 or more, and preferably 20 or less, more preferably 18 or less, still more preferably 15 or less.

Any two of $R^{1a}$, $R^{2a}$, and $R^{3a}$ optionally bind to each other to form a ring.

In the formula (a), $X^a$ is H, a metal atom, $NR^{4a}_4$, imidazolium optionally having a substituent, pyridinium optionally having a substituent, or phosphonium optionally having a substituent, wherein $R^{4a}$ is H or an organic group. The four $R^{4a}$ may be the same as or different from each other. $R^{4a}$ is preferably H or an organic group having 1 to 10 carbon atoms, and more preferably H or an organic group having 1 to 4 carbon atoms. Examples of the metal atom include monovalent and divalent metal atoms, and examples thereof include alkali metals (Group 1) and alkaline earth metals (Group 2), and preferred is Na, K or Li.

$X^a$ is preferably H, an alkali metal (Group 1), an alkaline earth metal (Group 2), or $NR^{4a}_4$, more preferably H, Na, K, Li, or $NH_4$ because they are easily dissolved in water, still more preferably Na, K, or $NH_4$ because they are more easily dissolved in water, particularly preferably Na or $NH_4$, and most preferably $NH_4$ because it can be easily removed. When $X^a$ is $NH_4$, the solubility of the surfactant in an aqueous medium is excellent, and the metal component is unlikely to remain in the PTFE or the final product.

$R^{1a}$ is preferably a linear or branched alkyl group having 1 to 8 carbon atoms and free from a carbonyl group, a cyclic alkyl group having 3 to 8 carbon atoms and free from a carbonyl group, a linear or branched alkyl group having 2 to 45 carbon atoms and containing 1 to 10 carbonyl groups, a cyclic alkyl group having 3 to 45 carbon atoms and containing a carbonyl group, or an alkyl group having 3 to 45 carbon atoms and containing a monovalent or divalent heterocycle.

$R^{1a}$ is more preferably a group represented by the following formula:

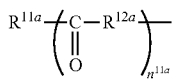

wherein $n^{11a}$ is an integer of 0 to 10; $R^{11a}$ is a linear or branched alkyl group having 1 to 5 carbon atoms or a cyclic alkyl group having 3 to 5 carbon atoms; $R^{12a}$ is an alkylene group having 0 to 3 carbon atoms; and when $n^{11a}$ is an integer of 2 to 10, each $R^{12a}$ may be the same or different.

$n^{11a}$ is preferably an integer of 0 to 5, more preferably an integer of 0 to 3, and still more preferably an integer of 1 to 3.

The alkyl group for $R^{11a}$ is preferably free from a carbonyl group.

In the alkyl group for $R^{11a}$, a hydrogen atom bonded to a carbon atom may be replaced by a functional group such as a hydroxy group (—OH) or a monovalent organic group containing an ester bond. Still, it is preferably not replaced by any functional group.

An example of the monovalent organic group containing an ester bond is a group represented by the formula: —O—C(=O)—$R^{103a}$, wherein $R^{103a}$ is an alkyl group.

In the alkyl group for $R^{11a}$, 75% or less of the hydrogen atoms bonded to the carbon atoms may be replaced by halogen atoms, 50% or less thereof may be replaced by halogen atoms, or 25% or less thereof may be replaced by halogen atoms. The alkyl group is preferably a non-halogenated alkyl group free from halogen atoms such as fluorine atoms and chlorine atoms.

$R^{12a}$ is an alkylene group having 0 to 3 carbon atoms. The alkylene group preferably has 1 to 3 carbon atoms.

The alkylene group for $R^{12a}$ may be either linear or branched.

The alkylene group for $R^{12a}$ is preferably free from a carbonyl group. $R^{12a}$ is more preferably an ethylene group (—$C_2H_4$—) or a propylene group (—$C_3H_6$—).

In the alkylene group for $R^{12a}$, a hydrogen atom bonded to a carbon atom may be replaced by a functional group such as a hydroxy group (—OH) or a monovalent organic group containing an ester bond. Still, it is preferably not replaced by any functional group.

An example of the monovalent organic group containing an ester bond is a group represented by the formula: —O—C(=O)—$R^{104a}$, wherein $R^{104a}$ is an alkyl group.

In the alkylene group for $R^{12a}$, 75% or less of the hydrogen atoms bonded to the carbon atoms may be replaced by halogen atoms, 50% or less thereof may be replaced by halogen atoms, or 25% or less thereof may be replaced by halogen atoms. The alkylene group is preferably a non-halogenated alkylene group free from halogen atoms such as fluorine atoms and chlorine atoms.

$R^{2a}$ and $R^{3a}$ are preferably each independently an alkylene group having 1 or more carbon atoms and free from a carbonyl group, more preferably an alkylene group having 1 to 3 carbon atoms and free from a carbonyl group, and still more preferably an ethylene group (—$C_2H_4$—) or a propylene group (—$C_3H_6$—).

Examples of the surfactant (a) include the following surfactants. In each formula, $X^a$ is defined as described above.

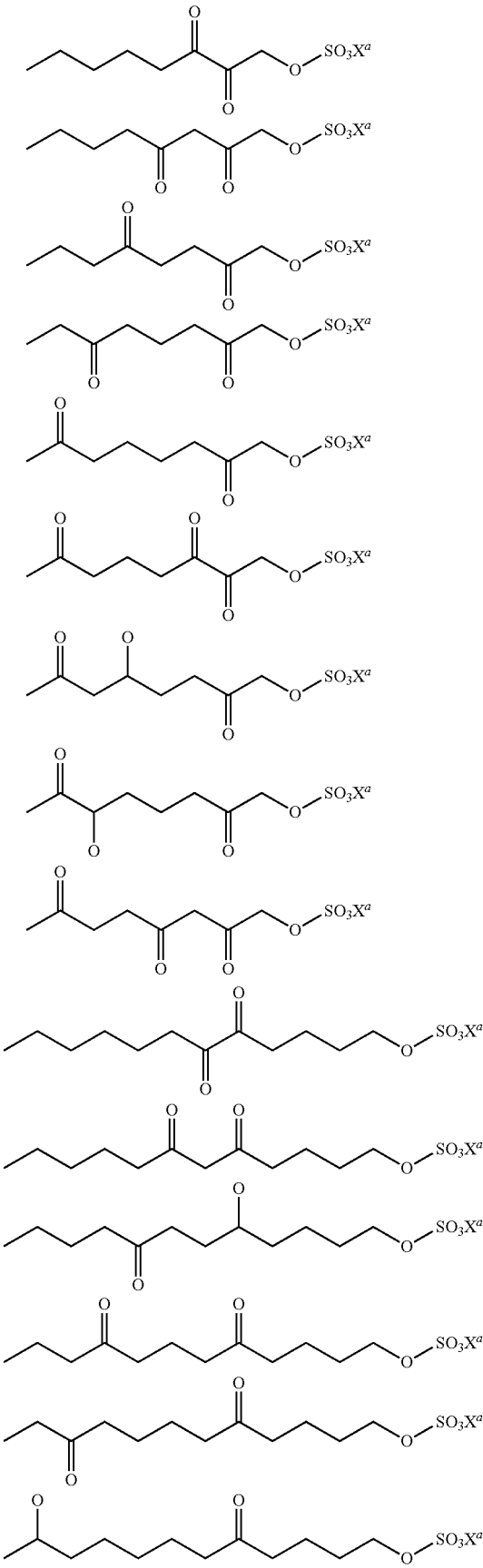

67
-continued
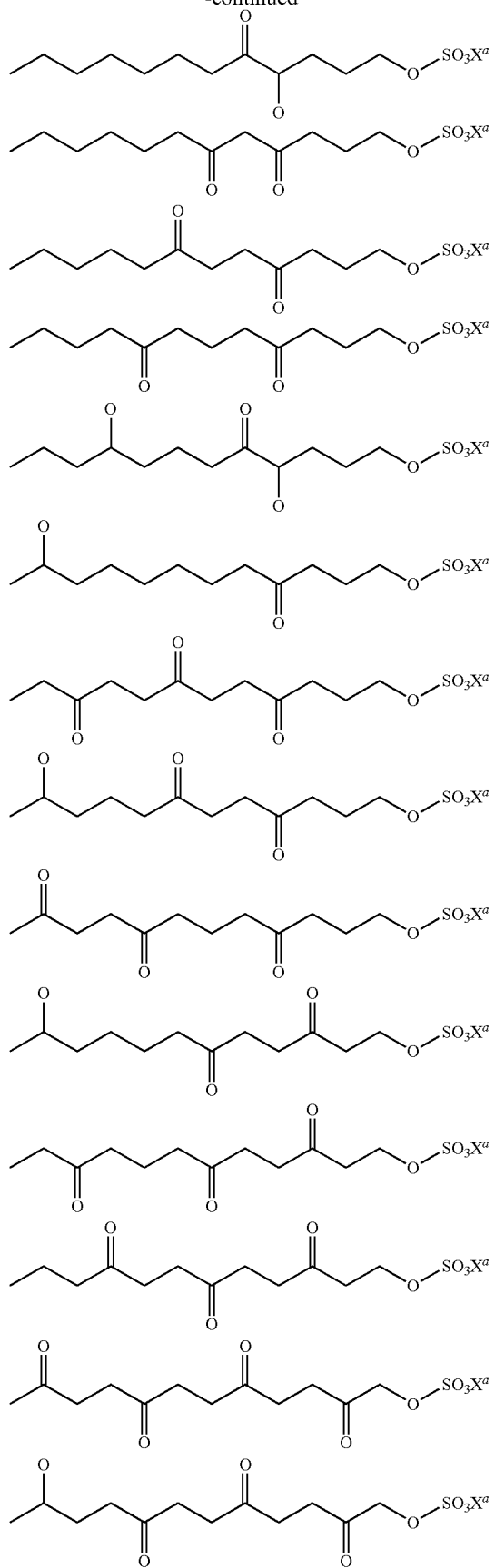
68
-continued
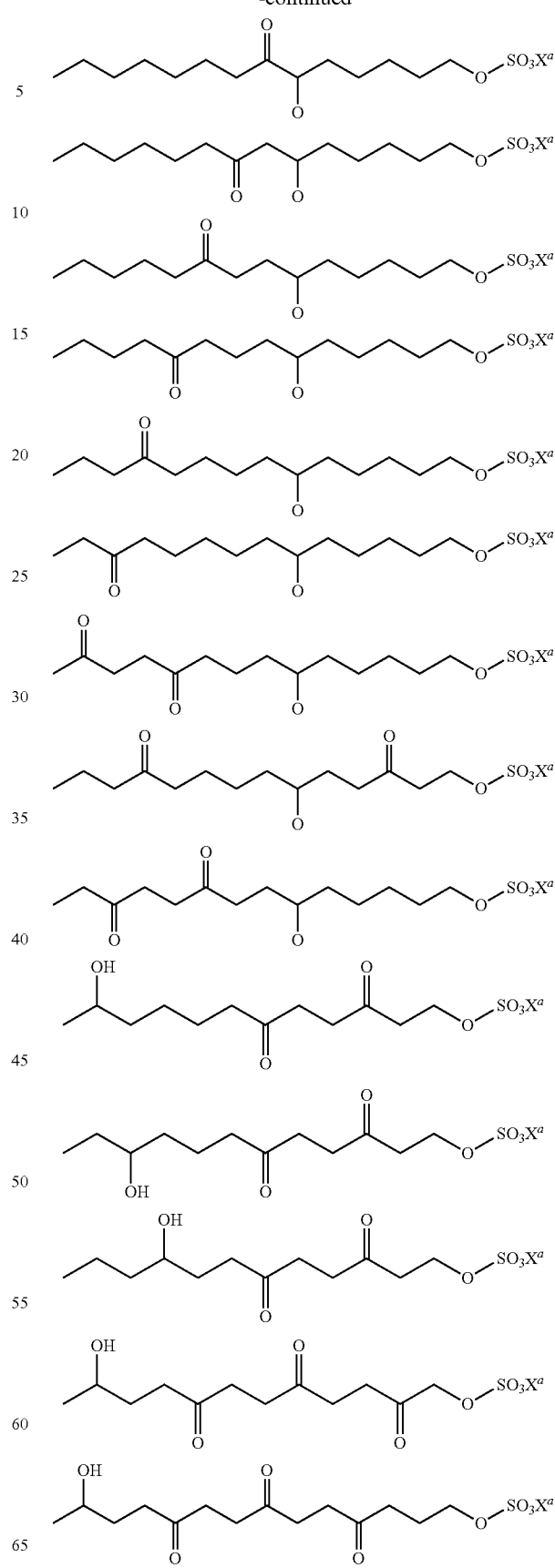

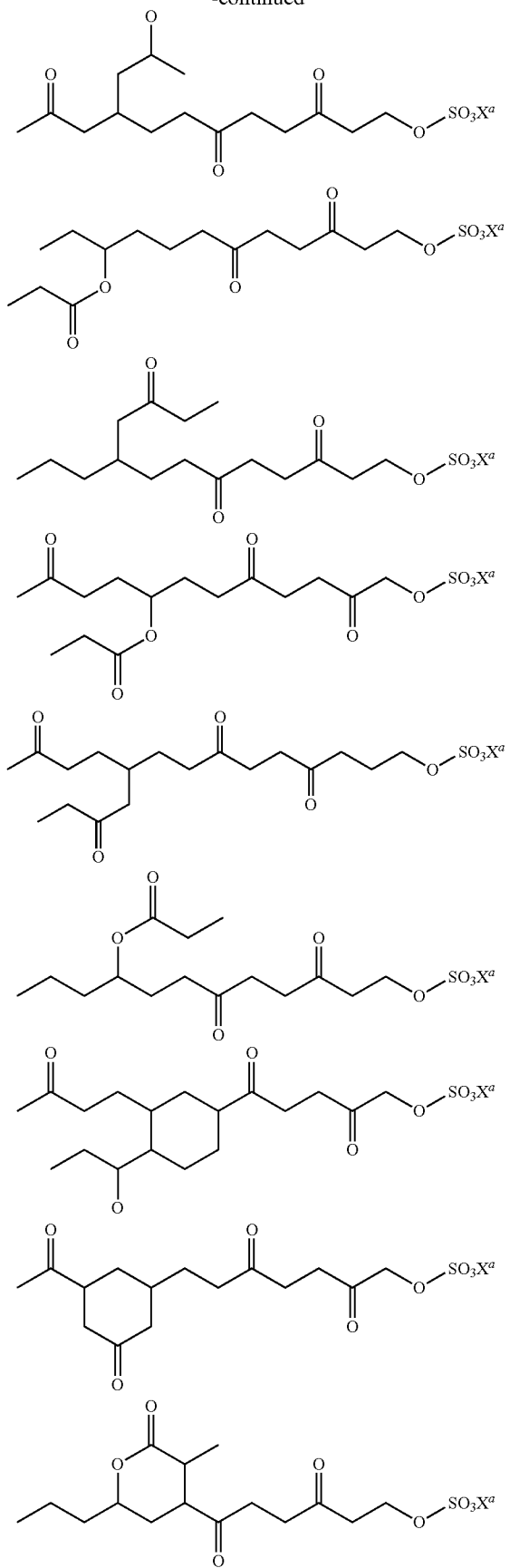
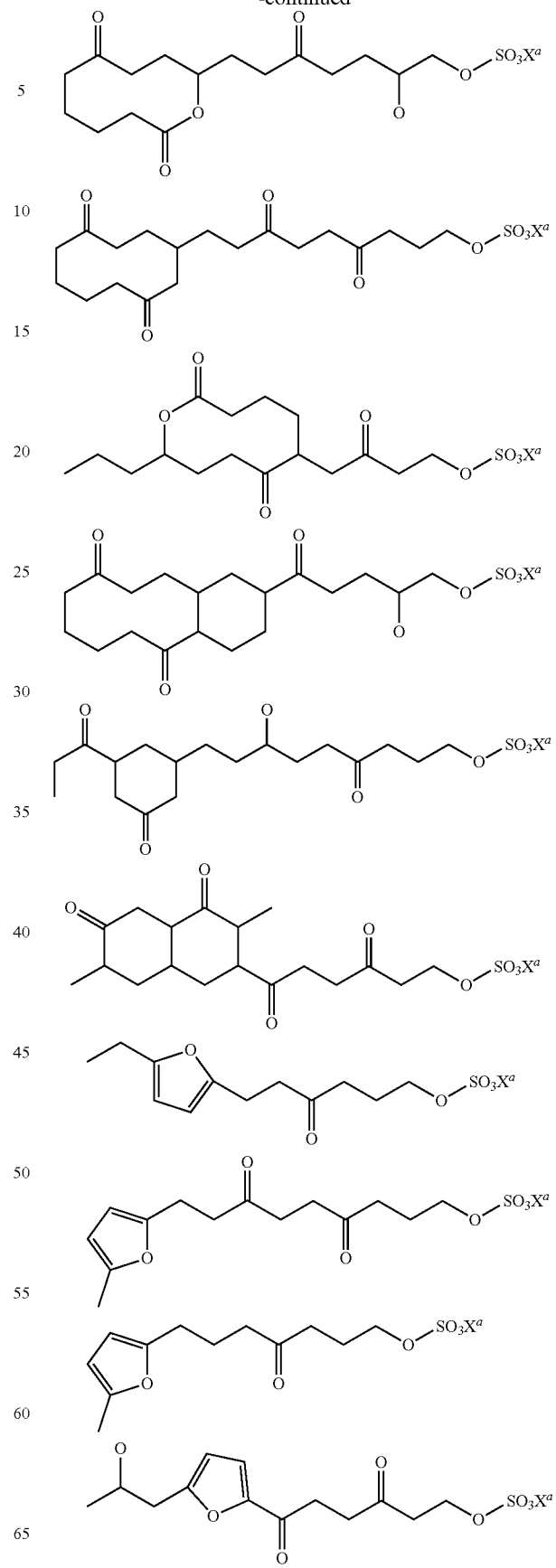

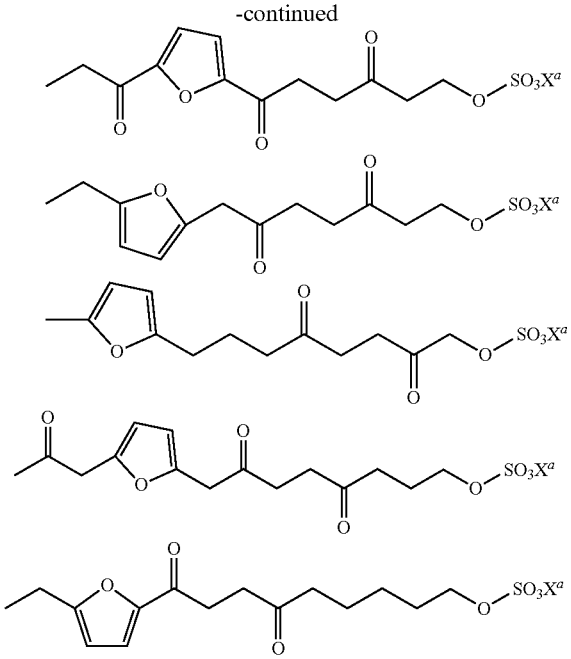

The surfactant (a) is a novel compound, and may be produced by any of the following production methods, for example.

The surfactant (a) may be produced by a production method including:
a step (11a) of reacting a compound (10a) represented by the formula:

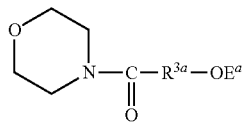

(wherein $R^{3a}$ is defined as described above; and $E^a$ is a leaving group), lithium, and a chlorosilane compound represented by the formula: $R^{201a}{}_3Si\text{—}Cl$ (wherein each $R^{201a}$ is independently an alkyl group or an aryl group) to provide a compound (11a) represented by the formula:

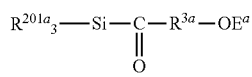

(wherein $R^{3a}$, $R^{201a}$, and $E^a$ are defined as described above);
a step (12a) of reacting the compound (11a) and an olefin represented by the formula:

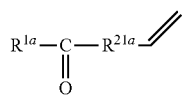

(wherein $R^{1a}$ is defined as described above; and $R^{21a}$ is a single bond or a divalent linking group) to provide a compound (12a) represented by the formula:

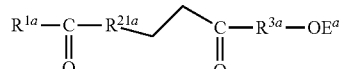

(wherein $R^{1a}$, $R^{21a}$, $R^{3a}$, and $E^a$ are defined as described above);
a step (13a) of eliminating the leaving group in the compound (12a) to provide a compound (13a) represented by the formula:

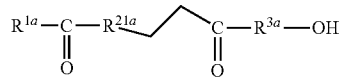

(wherein $R^{1a}$, $R^{21a}$, and $R^{3a}$ are defined as described above); and
a step (14a) of reacting the compound (13a) and a chlorosulfonic acid represented by the formula:

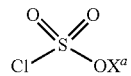

(wherein $X^a$ is defined as described above) to provide a compound (23a) represented by the formula:

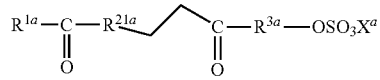

(wherein $R^{1a}$, $R^{21a}$, $R^{3a}$, and $X^a$ are defined as described above).

When $R^{1a}$ contains a furan ring, the furan ring may be cleaved by an acid and converted into a dicarbonyl derivative, for example. Examples of the acid include acetic acid, hydrochloric acid, and p-toluene sulfone, of which acetic acid is preferred.

In the step (11a), it is preferable that lithium and the chlorosilane compound are reacted in advance to obtain a syroxylithium compound, and then the syroxylithium compound and the compound (10a) are reacted to obtain the compound (11a).

$E^a$ represents a leaving group. Examples of the leaving group include a tert-butyldimethylsilyl (TBS) group, a triethylsilyl (TES) group, a triisopropylsilyl (TIPS) group, a tert-butyldiphenylsilyl (TBDPS) group, and a benzyl (Bn) group.

$R^{21a}$ is preferably a single bond or a linear or branched alkylene group having 1 or more carbon atoms.

Examples of the chlorosilane compound include:

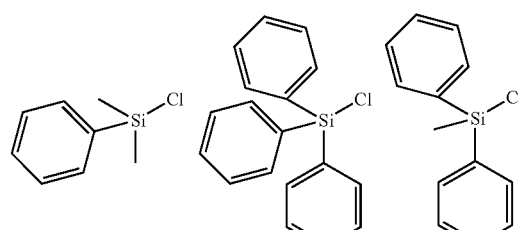

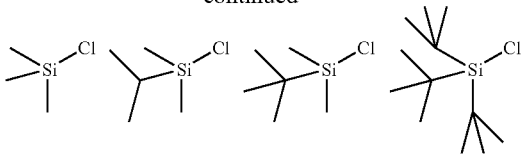

Any of the reactions in the step (11a) may be performed in a solvent. The solvent is preferably an organic solvent, more preferably an aprotic polar solvent, and still more preferably an ether. Examples of the ether include ethyl methyl ether, diethyl ether, monoglyme (ethylene glycol dimethyl ether), diglyme (diethylene glycol dimethyl ether), triglyme (triethylene glycol dimethyl ether), tetrahydrofuran, tetraglyme (tetraethylene glycol dimethyl ether), and crown ether (15-crown-5, 18-crown-6), of which tetrahydrofuran and diethyl ether is preferred.

The reaction temperature of lithium and the chlorosilane compound in the step (11a) is preferably 10 to 40° C., and more preferably 20 to 30° C.

The reaction temperature of the siloxylithium compound and the compound (10a) in the step (11a) is preferably −100 to 0° C., and more preferably −80 to −50° C.

The reaction pressure of lithium and the chlorosilane compound in the step (11a) is preferably 0.1 to 5 MPa, and more preferably 0.1 to 1 MPa.

The reaction pressure of the siloxylithium compound and the compound (10a) in the step (11a) is preferably 0.1 to 5 MPa, and more preferably 0.1 to 1 MPa.

The reaction time of lithium and the chlorosilane compound in the step (11a) is preferably 0.1 to 72 hours, and more preferably 6 to 10 hours.

The reaction time of the siloxylithium compound and the compound (10a) in the step (11a) is preferably 0.1 to 72 hours, and more preferably 1 to 2 hours.

Regarding the reaction ratio between the compound (11a) and the olefin in the step (12a), the amount of the olefin is preferably 1 to 2 mol, and more preferably 1 to 1.1 mol, based on 1 mol of the compound (11a) in consideration of the improvement of the yield and the reduction of the waste.

The reaction in the step (12a) may be performed in a solvent in the presence of a thiazolium salt and a base.

Examples of the thiazolium salt include 3-ethyl-5-(2-hydroxyethyl)-4-methylthiazolium bromide and 3-benzyl-5-(2-hydroxyethyl)-4-methylthiazolium chloride.

Examples of the base include 1,8-diazabicyclo[5.4.0]-7-undecene and triethylamine.

The solvent is preferably an organic solvent, more preferably an aprotic polar solvent, and still more preferably an alcohol or an ether.

Examples of the alcohol include methanol, ethanol, 1-propanol, and isopropanol.

Examples of the ether include ethyl methyl ether, diethyl ether, monoglyme (ethylene glycol dimethyl ether), diglyme (diethylene glycol dimethyl ether), triglyme (triethylene glycol dimethyl ether), tetrahydrofuran, tetraglyme (tetraethylene glycol dimethyl ether), and crown ether (15-crown-5, 18-crown-6), of which tetrahydrofuran and diethyl ether is preferred.

The reaction temperature in the step (12a) is preferably 40 to 60° C., and more preferably 50 to 55° C.

The reaction pressure in the step (12a) is preferably 0.1 to 5 MPa, and more preferably 0.1 to 1 MPa.

The reaction duration in the step (12a) is preferably 0.1 to 72 hours, and more preferably 6 to 10 hours.

The elimination reaction for the leaving group in the step (13a) may be performed using a fluoride ion or an acid. Examples of methods of eliminating the leaving group include a method using hydrofluoric acid; a method using an amine complex of hydrogen fluoride such as pyridine-nHF or triethylamine-nHF; a method using an inorganic salt such as cesium fluoride, potassium fluoride, lithium tetrafluoroborate ($LiBF_4$), or ammonium fluoride; and a method using an organic salt such as tetrabutylammonium fluoride (TBAF).

The elimination reaction for the leaving group in the step (13a) may be performed in a solvent. The solvent is preferably an organic solvent, more preferably an aprotic polar solvent, and still more preferably an ether.

Examples of the ether include ethyl methyl ether, diethyl ether, monoglyme (ethylene glycol dimethyl ether), diglyme (diethylene glycol dimethyl ether), triglyme (triethylene glycol dimethyl ether), tetrahydrofuran, tetraglyme (tetraethylene glycol dimethyl ether), and crown ether (15-crown-5, 18-crown-6), of which tetrahydrofuran and diethyl ether is preferred.

The reaction temperature in the step (13a) is preferably 0 to 40° C., and more preferably 0 to 20° C.

The reaction pressure in the step (13a) is preferably 0.1 to 5 MPa, and more preferably 0.1 to 1 MPa.

The reaction duration in the step (13a) is preferably 0.1 to 72 hours, and more preferably 3 to 8 hours.

Regarding the reaction ratio between the compound (13a) and the chlorosulfonic acid in the step (14a), the amount of the chlorosulfonic acid is preferably 1 to 2 mol, and more preferably 1 to 1.1 mol, based on 1 mol of the compound (13a) in consideration of the improvement of the yield and the reduction of the waste.

The reaction in the step (14a) is preferably performed in the presence of a base. Examples of the base include alkali metal hydroxides, alkaline earth metal hydroxides, and amines, of which amines are preferred.

Examples of the amines in the step (14a) include tertiary amines such as trimethylamine, triethylamine, tributylamine, N,N-dimethylaniline, dimethylbenzylamine, and N,N,N',N'-tetramethyl-1,8-naphthalenediamine, heteroaromatic amines such as pyridine, pyrrole, uracil, collidine, and lutidine, and cyclic amines such as 1,8-diaza-bicyclo[5.4.0]-7-undecene and 1,5-diaza-bicyclo[4.3.0]-5-nonene. Of these, triethylamine and pyridine are preferred.

The amount of the base used in the step (14a) is preferably 1 to 2 mol, and more preferably 1 to 1.1 mol, based on 1 mol of the compound (13a) in consideration of the improvement of the yield and the reduction of the waste.

The reaction in the step (14a) may be performed in a polar solvent. The solvent is preferably an organic solvent, more preferably an aprotic polar solvent, and still more preferably an ether.

Examples of the ether include ethyl methyl ether, diethyl ether, monoglyme (ethylene glycol dimethyl ether) diglyme (diethylene glycol dimethyl ether), triglyme (triethylene glycol dimethyl ether), tetrahydrofuran, tetraglyme (tetraethylene glycol dimethyl ether), and crown ether (15-crown-5, 18-crown-6), of which diethyl ether is preferred.

The reaction temperature in the step (14a) is preferably 0 to 40° C., and more preferably 0 to 20° C.

The reaction pressure in the step (14a) is preferably 0.1 to 5 MPa, and more preferably 0.1 to 1 MPa.

The reaction duration in the step (14a) is preferably 0.1 to 72 hours, and more preferably 3 to 12 hours.

When the reaction in step (14a) is performed in a solvent, a solution containing compound (14a) is obtained after the reaction is completed. High-purity compound (14a) may be recovered by adding water to the above solution, allowing it to stand to separate it into two phases, recovering the aqueous phase, and distilling off the solvent. When the compound (14a) has a group represented by —OSO$_3$H (that is, when X is H), it is also possible to convert the —OSO$_3$H to sulfate groups by using an alkaline aqueous solution such as aqueous sodium hydrogen carbonate or aqueous ammonia instead of water.

After the completion of each step, the solvent may be distilled off, or distillation, purification or the like may be performed to increase the purity of each resulting compound.

The surfactant (a) may also be produced by a production method including:

a step (21a) of reacting a ketone represented by the formula:

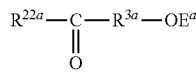

(wherein $R^{3a}$ is defined as described above; $R^{22a}$ is a monovalent organic group; and $E^a$ is a leaving group) and a carboxylate represented by the formula:

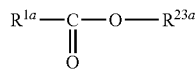

(wherein $R^{1a}$ is defined as described above; and $R^{23a}$ is a monovalent organic group) to provide a compound (21a) represented by the formula:

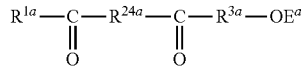

(wherein $R^{1a}$, $R^{3a}$, and $E^a$ are defined as described above; and $R^{24a}$ is a single bond or a divalent linking group);

a step (22a) of eliminating the leaving group in the compound (21a) to provide a compound (22a) represented by the formula:

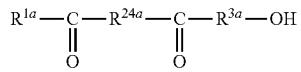

(wherein $R^{1a}$, $R^{24a}$, and $R^{3a}$ are defined as described above); and a step (23a) of reacting the compound (22a) and a chlorosulfonic acid represented by the formula:

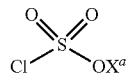

(wherein $X^a$ is defined as described above) to provide a compound (23a) represented by the formula:

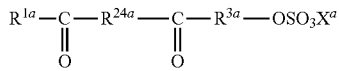

(wherein $R^{1a}$, $R^{24a}$, $R^{3a}$, and $X^a$ are defined as described above).

When $R^{1a}$ contains a furan ring, the furan ring may be cleaved by an acid and converted into a dicarbonyl derivative, for example. Examples of the acid include acetic acid, hydrochloric acid, and p-toluene sulfone, of which acetic acid is preferred.

$E^a$ represents a leaving group. Examples of the leaving group include a tert-butyldimethylsilyl (TBS) group, a triethylsilyl (TES) group, a triisopropylsilyl (TIPS) group, a tert-butyldiphenylsilyl (TBDPS) group, and a benzyl (Bn) group.

$R^{22a}$ is preferably a linear or branched alkyl group having 1 or more carbon atoms, and more preferably a methyl group.

$R^{23a}$ is preferably a linear or branched alkyl group having 1 or more carbon atoms, and more preferably a methyl group.

$R^{24a}$ is preferably a linear or branched alkylene group having 1 or more carbon atoms, and more preferably a methylene group (—CH$_2$—).

The reaction in the step (21a) may be performed in a solvent in the presence of a base.

Examples of the base include sodium amide, sodium hydride, sodium methoxide, and sodium ethoxide.

The solvent is preferably an organic solvent, more preferably an aprotic polar solvent, and still more preferably an alcohol or an ether.

Examples of the alcohol include methanol, ethanol, 1-propanol, and isopropanol.

Examples of the ether include ethyl methyl ether, diethyl ether, monoglyme (ethylene glycol dimethyl ether), diglyme (diethylene glycol dimethyl ether), triglyme (triethylene glycol dimethyl ether), tetrahydrofuran, tetraglyme (tetraethylene glycol dimethyl ether), and crown ether (15-crown-5, 18-crown-6), of which tetrahydrofuran and diethyl ether is preferred.

The reaction temperature in the step (21a) is preferably 0 to 40° C., and more preferably 0 to 20° C.

The reaction pressure in the step (21a) is preferably 0.1 to 5 MPa, and more preferably 0.1 to 1 MPa.

The reaction duration in the step (21a) is preferably 0.1 to 72 hours, and more preferably 3 to 8 hours.

The elimination reaction for the leaving group in the step (22a) may be performed using a fluoride ion or an acid. Examples of methods of eliminating the leaving group include a method using hydrofluoric acid; a method using an amine complex of hydrogen fluoride such as pyridine-nHF or triethylamine-nHF; a method using an inorganic salt such as cesium fluoride, potassium fluoride, lithium tetrafluoroborate (LiBF$_4$), or ammonium fluoride; and a method using an organic salt such as tetrabutylammonium fluoride (TBAF).

The elimination reaction for the leaving group in the step (22a) may be performed in a solvent. The solvent is preferably an organic solvent, more preferably an aprotic polar solvent, and still more preferably an ether.

Examples of the ether include ethyl methyl ether, diethyl ether, monoglyme (ethylene glycol dimethyl ether), diglyme (diethylene glycol dimethyl ether), triglyme (triethylene glycol dimethyl ether), tetrahydrofuran, tetraglyme (tetraethylene glycol dimethyl ether), and crown ether (15-crown-5, 18-crown-6), of which tetrahydrofuran and diethyl ether is preferred.

The reaction temperature in the step (22a) is preferably 0 to 40° C., and more preferably 0 to 20° C.

The reaction pressure in the step (22a) is preferably 0.1 to 5 MPa, and more preferably 0.1 to 1 MPa.

The reaction duration in the step (22a) is preferably 0.1 to 72 hours, and more preferably 3 to 8 hours.

Regarding the reaction ratio between the compound (22a) and the chlorosulfonic acid in the step (23a), the amount of the chlorosulfonic acid is preferably 1 to 2 mol, and more preferably 1 to 1.1 mol, based on 1 mol of the compound (22a) in consideration of the improvement of the yield and the reduction of the waste.

The reaction in the step (23a) is preferably performed in the presence of a base. Examples of the base include alkali metal hydroxides, alkaline earth metal hydroxides, and amines, of which amines are preferred.

Examples of the amines in the step (23a) include tertiary amines such as trimethylamine, triethylamine, tributylamine, N,N-dimethylaniline, dimethylbenzylamine, and N,N,N',N'-tetramethyl-1,8-naphthalenediamine, heteroaromatic amines such as pyridine, pyrrole, uracil, collidine, and lutidine, and cyclic amines such as 1,8-diaza-bicyclo[5.4.0]-7-undecene and 1,5-diaza-bicyclo[4.3.0]-5-nonene. Of these, triethylamine and pyridine are preferred.

The amount of the base used in the step (23a) is preferably 1 to 2 mol, and more preferably 1 to 1.1 mol, based on 1 mol of the compound (22a) in consideration of the improvement of the yield and the reduction of the waste.

The reaction in the step (23a) may be performed in a polar solvent. The solvent is preferably an organic solvent, more preferably an aprotic polar solvent, and still more preferably an ether.

Examples of the ether include ethyl methyl ether, diethyl ether, monoglyme (ethylene glycol dimethyl ether), diglyme (diethylene glycol dimethyl ether), triglyme (triethylene glycol dimethyl ether), tetrahydrofuran, tetraglyme (tetraethylene glycol dimethyl ether), and crown ether (15-crown-5, 18-crown-6), of which diethyl ether is preferred.

The reaction temperature in the step (23a) is preferably 0 to 40° C., and more preferably 0 to 20° C.

The reaction pressure in the step (23a) is preferably 0.1 to 5 MPa, and more preferably 0.1 to 1 MPa.

The reaction duration in the step (23a) is preferably 0.1 to 72 hours, and more preferably 3 to 12 hours.

When the reaction in step (23a) is performed in a solvent, a solution containing compound (23a) is obtained after the reaction is completed. High-purity compound (23a) may be recovered by adding water to the above solution, allowing it to stand to separate it into two phases, recovering the aqueous phase, and distilling off the solvent. When the compound (23a) has a group represented by —OSO$_3$H (that is, when X is H), it is also possible to convert the —OSO$_3$H to sulfate groups by using an alkaline aqueous solution such as aqueous sodium hydrogen carbonate or aqueous ammonia instead of water.

After the completion of each step, the solvent may be distilled off, or distillation, purification or the like may be performed to increase the purity of each resulting compound.

The surfactant (a) may also be produced by a production method including:
a step (31a) of reacting an alkyl halide represented by the formula:

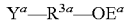

(wherein $R^{3a}$ is defined as described above; $Y^a$ is a halogen atom; and $E^a$ is a leaving group) and lithium acetylide represented by the formula:

(wherein $R^{1a}$ is defined as described above) to provide a compound (31a) represented by the formula:

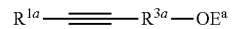

(wherein $R^{1a}$, $R^{3a}$, and $E^a$ are defined as described above);
a step (32a) of oxidizing the compound (31a) to provide a compound (32a) represented by the formula:

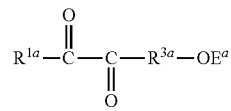

(wherein $R^{1a}$, $R^{3a}$, and $E^a$ are defined as described above);
a step (33a) of eliminating the leaving group in the compound (32a) to provide a compound (33a) represented by the formula:

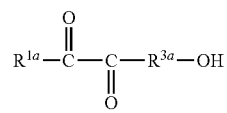

(wherein $R^{1a}$ and $R^{3a}$ are defined as described above); and
a step (34a) of reacting the compound (33a) and a chlorosulfonic acid represented by the formula:

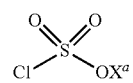

(wherein $X^a$ is defined as described above) to provide a compound (23a) represented by the formula:

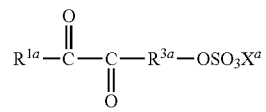

(wherein $R^{1a}$, $R^{3a}$, and $X^a$ are defined as described above).

When $R^{1a}$ contains a furan ring, the furan ring may be cleaved by an acid and converted into a dicarbonyl derivative, for example. Examples of the acid include acetic acid, hydrochloric acid, and p-toluene sulfone, of which acetic acid is preferred.

E$^a$ represents a leaving group. Examples of the leaving group include a tert-butyldimethylsilyl (TBS) group, a triethylsilyl (TES) group, a triisopropylsilyl (TIPS) group, a tert-butyldiphenylsilyl (TBDPS) group, and a benzyl (Bn) group.

Regarding the reaction ratio between the alkyl halide and the lithium acetylide in the step (31a), the lithium acetylide is preferably used in an amount of 1 to 2 mol, and more preferably 1 to 1.2 mol, based on 1 mol of the alkyl halide in consideration of the improvement of the yield and the reduction of the waste.

The reaction in the step (31a) may be performed in a solvent. Hexane is preferable as the solvent.

The reaction temperature in the step (31a) is preferably −100 to −40° C., and more preferably −80 to −50° C.

The reaction pressure in the step (31a) is preferably 0.1 to 5 MPa, and more preferably 0.1 to 1 MPa.

The reaction duration in the step (31a) is preferably 0.1 to 72 hours, and more preferably 6 to 10 hours.

The oxidation in the step (32a) may be performed in a nitrile solvent using a complex generated by treating [(Cn*)Ru$^{III}$(CF$_3$CO$_2$)$_3$]·H$_2$O (wherein Cn* is 1,4,7-trimethyl-1,4,7-triazabicyclononane) with (NH$_4$)$_2$Ce(NO$_3$)$_6$ and trifluoroacetic acid and then adding sodium perchlorate thereto.

After the completion of the oxidation, the product may be neutralized with an alkali, and then an organic solvent such as an ether may be used to extract the compound (32a).

The reaction temperature in the step (32a) is preferably 30 to 100° C., and more preferably 40 to 90° C.

The reaction pressure in the step (32a) is preferably 0.1 to 5 MPa, and more preferably 0.1 to 1 MPa.

The reaction duration in the step (32a) is preferably 0.1 to 72 hours, and more preferably 3 to 8 hours.

The elimination reaction for the leaving group in the step (33a) may be performed using a fluoride ion or an acid. Examples of methods of eliminating the leaving group include a method using hydrofluoric acid; a method using an amine complex of hydrogen fluoride such as pyridine-nHF or triethylamine-nHF; a method using an inorganic salt such as cesium fluoride, potassium fluoride, lithium tetrafluoroborate (LiBF$_4$), or ammonium fluoride; and a method using an organic salt such as tetrabutylammonium fluoride (TBAF).

The elimination reaction for the leaving group in the step (33a) may be performed in a solvent. The solvent is preferably an organic solvent, more preferably an aprotic polar solvent, and still more preferably an ether.

Examples of the ether include ethyl methyl ether, diethyl ether, monoglyme (ethylene glycol dimethyl ether), diglyme (diethylene glycol dimethyl ether), triglyme (triethylene glycol dimethyl ether), tetrahydrofuran, tetraglyme (tetraethylene glycol dimethyl ether), and crown ether (15-crown-5, 18-crown-6), of which tetrahydrofuran and diethyl ether is preferred.

The reaction temperature in the step (33a) is preferably 0 to 40° C., and more preferably 0 to 20° C.

The reaction pressure in the step (33a) is preferably 0.1 to 5 MPa, and more preferably 0.1 to 1 MPa.

The reaction duration in the step (33a) is preferably 0.1 to 72 hours, and more preferably 3 to 8 hours.

Regarding the reaction ratio between the compound (33a) and the chlorosulfonic acid in the step (34a), the amount of the chlorosulfonic acid is preferably 1 to 2 mol, and more preferably 1 to 1.1 mol, based on 1 mol of the compound (33a) in consideration of the improvement of the yield and the reduction of the waste.

The reaction in the step (34a) is preferably performed in the presence of a base. Examples of the base include alkali metal hydroxides, alkaline earth metal hydroxides, and amines, of which amines are preferred.

Examples of the amines in the step (34a) include tertiary amines such as trimethylamine, triethylamine, tributylamine, N,N-dimethylaniline, dimethylbenzylamine, and N,N,N',N'-tetramethyl-1,8-naphthalenediamine, heteroaromatic amines such as pyridine, pyrrole, uracil, collidine, and lutidine, and cyclic amines such as 1,8-diaza-bicyclo[5.4.0]-7-undecene and 1,5-diaza-bicyclo[4.3.0]-5-nonene. Of these, triethylamine and pyridine are preferred.

The amount of the base used in the step (34a) is preferably 1 to 2 mol, and more preferably 1 to 1.1 mol, based on 1 mol of the compound (33a) in consideration of the improvement of the yield and the reduction of the waste.

The reaction in the step (34a) may be performed in a polar solvent. The solvent is preferably an organic solvent, more preferably an aprotic polar solvent, and still more preferably an ether.

Examples of the ether include ethyl methyl ether, diethyl ether, monoglyme (ethylene glycol dimethyl ether) diglyme (diethylene glycol dimethyl ether), triglyme (triethylene glycol dimethyl ether), tetrahydrofuran, tetraglyme (tetraethylene glycol dimethyl ether), and crown ether (15-crown-5, 18-crown-6), of which diethyl ether is preferred.

The reaction temperature in the step (34a) is preferably 0 to 40° C., and more preferably 0 to 20° C.

The reaction pressure in the step (34a) is preferably 0.1 to 5 MPa, and more preferably 0.1 to 1 MPa.

The reaction duration in the step (34a) is preferably 0.1 to 72 hours, and more preferably 3 to 12 hours.

When the reaction in step (34a) is performed in a solvent, a solution containing compound (34a) is obtained after the reaction is completed. High-purity compound (34a) may be recovered by adding water to the above solution, allowing it to stand to separate it into two phases, recovering the aqueous phase, and distilling off the solvent. When the compound (34a) has a group represented by —OSO$_3$H (that is, when X is H), it is also possible to convert the —OSO$_3$H to sulfate groups by using an alkaline aqueous solution such as aqueous sodium hydrogen carbonate or aqueous ammonia instead of water.

After the completion of each step, the solvent may be distilled off, or distillation, purification or the like may be performed to increase the purity of each resulting compound.

The surfactant (a) may also be produced by a production method including:

a step (41a) of reacting an alkene represented by the formula:

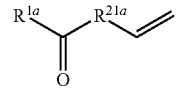

(wherein R$^{1a}$ is defined as described above; and R$^{21a}$ is a single bond or a divalent linking group) and an alkyne represented by the formula:

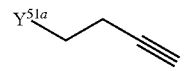

(wherein $Y^{51a}$ is an alkoxyl group) to provide a compound (41a) represented by the formula:

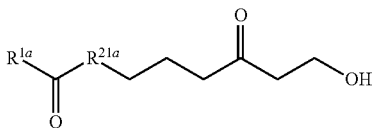

(wherein $R^{1a}$ and $R^{21a}$ are defined as mentioned above); and a step (42a) of reacting the compound (41a) and a chlorosulfonic acid represented by the formula:

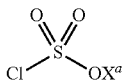

(wherein $X^a$ is defined as described above) to provide a compound (23a) represented by the formula:

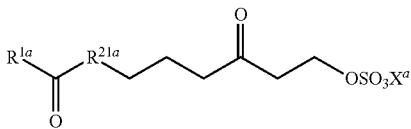

(wherein $R^{1a}$, $R^{21a}$, and $X^a$ are defined as described above).

When $R^{1a}$ contains a furan ring, the furan ring may be cleaved by an acid and converted into a dicarbonyl derivative, for example. Examples of the acid include acetic acid, hydrochloric acid, and p-toluene sulfone, of which acetic acid is preferred.

$R^{21a}$ is preferably a single bond or a linear or branched alkylene group having 1 or more carbon atoms.

Regarding the reaction ratio between the alkene and the alkyne in the step (41a), the alkene is preferably used in an amount of 0.5 to 2 mol, and more preferably 0.6 to 1.2 mol, based on 1 mol of the alkyne in consideration of the improvement of the yield and the reduction of the waste.

The reaction in the step (41a) is preferably performed in the presence of a metal catalyst. An example of the metal is ruthenium.

The amount of the metal catalyst used in the step (41a) is preferably 0.01 to 0.4 mol, and more preferably 0.05 to 0.1 mol, based on 1 mol of the alkene in consideration of the improvement of the yield and the reduction of the waste.

The reaction in the step (41a) may be performed in a polar solvent. The solvent is preferably water, acetonitrile, dimethylacetamide, or dimethylformamide.

The reaction temperature in the step (41a) is preferably 20 to 160° C., and more preferably 40 to 140° C.

The reaction pressure in the step (41a) is preferably 0.1 to 5 MPa, and more preferably 0.1 to 1 MPa.

The reaction duration in the step (41a) is preferably 0.1 to 72 hours, and more preferably 4 to 8 hours.

Regarding the reaction ratio between the compound (41a) and the chlorosulfonic acid in the step (42a), the amount of the chlorosulfonic acid is preferably 1 to 2 mol, and more preferably 1 to 1.1 mol, based on 1 mol of the compound (41a) in consideration of the improvement of the yield and the reduction of the waste.

The reaction in the step (42a) is preferably performed in the presence of a base. Examples of the base include alkali metal hydroxides, alkaline earth metal hydroxides, and amines, of which amines are preferred.

Examples of the amines in the step (42a) include tertiary amines such as trimethylamine, triethylamine, tributylamine, N,N-dimethylaniline, dimethylbenzylamine, and N,N,N',N'-tetramethyl-1,8-naphthalenediamine, heteroaromatic amines such as pyridine, pyrrole, uracil, collidine, and lutidine, and cyclic amines such as 1,8-diaza-bicyclo[5.4.0]-7-undecene and 1,5-diaza-bicyclo[4.3.0]-5-nonene. Of these, triethylamine and pyridine are preferred.

The amount of the base used in the step (42a) is preferably 1 to 2 mol, and more preferably 1 to 1.1 mol, based on 1 mol of the compound (41a) in consideration of the improvement of the yield and the reduction of the waste.

The reaction in the step (42a) may be performed in a polar solvent. The solvent is preferably an organic solvent, more preferably an aprotic polar solvent, and still more preferably an ether.

Examples of the ether include ethyl methyl ether, diethyl ether, monoglyme (ethylene glycol dimethyl ether), diglyme (diethylene glycol dimethyl ether), triglyme (triethylene glycol dimethyl ether), tetrahydrofuran, tetraglyme (tetraethylene glycol dimethyl ether), and crown ether (15-crown-5, 18-crown-6), of which diethyl ether is preferred.

The reaction temperature in the step (42a) is preferably 0 to 40° C., and more preferably 0 to 20° C.

The reaction pressure in the step (42a) is preferably 0.1 to 5 MPa, and more preferably 0.1 to 1 MPa.

The reaction duration in the step (42a) is preferably 0.1 to 72 hours, and more preferably 3 to 12 hours.

When the reaction in step (42a) is performed in a solvent, a solution containing compound (42a) is obtained after the reaction is completed. High-purity compound (42a) may be recovered by adding water to the above solution, allowing it to stand to separate it into two phases, recovering the aqueous phase, and distilling off the solvent. When the compound (42a) has a group represented by —OSO$_3$H (that is, when X is H), it is also possible to convert the —OSO$_3$H to sulfate groups by using an alkaline aqueous solution such as aqueous sodium hydrogen carbonate or aqueous ammonia instead of water.

After the completion of each step, the solvent may be distilled off, or distillation, purification or the like may be performed to increase the purity of each resulting compound.

Next, the surfactant (b) is described below.

In the formula (b), $R^{1b}$ is a linear or branched alkyl group having 1 or more carbon atoms and optionally having a substituent or a cyclic alkyl group having 3 or more carbon atoms and optionally having a substituent.

When having 3 or more carbon atoms, the alkyl group optionally contains a monovalent or divalent heterocycle, or optionally forms a ring. The heterocycle is preferably an unsaturated heterocycle, more preferably an oxygen-containing unsaturated heterocycle, and examples thereof include a furan ring. In $R^{1b}$, a divalent heterocycle may be present between two carbon atoms, or a divalent heterocycle may be present at an end and bind to —C(=O)—, or a monovalent heterocycle may be present at an end of the alkyl group.

The "number of carbon atoms" in the alkyl group as used herein includes the number of carbon atoms constituting the heterocycles.

The substituent which may be contained in the alkyl group for $R^{1b}$ is preferably a halogen atom, a linear or branched alkyl group having 1 to 10 carbon atoms, or a cyclic alkyl group having 3 to 10 carbon atoms, or a hydroxy group, and particularly preferably a methyl group or an ethyl group.

The alkyl group for $R^{1b}$ is preferably free from a carbonyl group.

In the alkyl group, 75% or less of the hydrogen atoms bonded to the carbon atoms may be replaced by halogen atoms, 50% or less thereof may be replaced by halogen atoms, or 25% or less thereof may be replaced by halogen atoms. The alkyl group is preferably a non-halogenated alkyl group free from halogen atoms such as fluorine atoms and chlorine atoms.

The alkyl group preferably contains no substituent.

$R^{1b}$ is preferably a linear or branched alkyl group having 1 to 10 carbon atoms and optionally having a substituent or a cyclic alkyl group having 3 to 10 carbon atoms and optionally having a substituent, more preferably a linear or branched alkyl group having 1 to 10 carbon atoms and free from a carbonyl group or a cyclic alkyl group having 3 to 10 carbon atoms and free from a carbonyl group, still more preferably a linear or branched alkyl group having 1 to 10 carbon atoms and not having a substituent, further preferably a linear or branched alkyl group having 1 to 3 carbon atoms and not having a substituent, particularly preferably a methyl group (—$CH_3$) or an ethyl group (—$C_2H_5$), and most preferably a methyl group (—$CH_3$).

In the formula (b), $R^{2b}$ and $R^{4b}$ are each independently H or a substituent. A plurality of $R^{2b}$ and $R^{4b}$ may be the same or different.

The substituent for each of $R^{2b}$ and $R^{4b}$ is preferably a halogen atom, a linear or branched alkyl group having 1 to 10 carbon atoms, a cyclic alkyl group having 3 to 10 carbon atoms, or a hydroxy group, and particularly preferably a methyl group or an ethyl group.

The alkyl group for each of $R^{2b}$ and $R^{4b}$ is preferably free from a carbonyl group. In the alkyl group, 75% or less of the hydrogen atoms bonded to the carbon atoms may be replaced by halogen atoms, 50% or less thereof may be replaced by halogen atoms, or 25% or less thereof may be replaced by halogen atoms. The alkyl group is preferably a non-halogenated alkyl group free from halogen atoms such as fluorine atoms and chlorine atoms.

The alkyl group preferably contains no substituent.

The alkyl group for each of $R^{2b}$ and $R^{4b}$ is preferably a linear or branched alkyl group having 1 to 10 carbon atoms and free from a carbonyl group or a cyclic alkyl group having 3 to 10 carbon atoms and free from a carbonyl group, more preferably a linear or branched alkyl group having 1 to 10 carbon atoms and free from a carbonyl group, still more preferably a linear or branched alkyl group having 1 to 3 carbon atoms and not having a substituent, and particularly preferably a methyl group (—$CH_3$) or an ethyl group (—$C_2H_5$).

$R^{2b}$ and $R^{4b}$ are preferably each independently H or a linear or branched alkyl group having 1 to 10 carbon atoms and free from a carbonyl group, more preferably H or a linear or branched alkyl group having 1 to 3 carbon atoms and not having a substituent, still more preferably H, a methyl group (—$CH_3$), or an ethyl group (—$C_2H_5$), and particularly preferably H.

In the formula (b), $R^{3b}$ is an alkylene group having 1 to 10 carbon atoms and optionally having a substituent. When a plurality of $R^{3b}$ are present, they may be the same or different.

The alkylene group is preferably free from a carbonyl group.

In the alkylene group, 75% or less of the hydrogen atoms bonded to the carbon atoms may be replaced by halogen atoms, 50% or less thereof may be replaced by halogen atoms, or 25% or less thereof may be replaced by halogen atoms. The alkylene group is preferably a non-halogenated alkyl group free from halogen atoms such as fluorine atoms and chlorine atoms.

The alkylene group preferably does not have any substituent.

The alkylene group is preferably a linear or branched alkylene group having 1 to 10 carbon atoms and optionally having a substituent or a cyclic alkylene group having 3 to 10 carbon atoms and optionally having a substituent, preferably a linear or branched alkylene group having 1 to 10 carbon atoms and free from a carbonyl group or a cyclic alkylene group having 3 to 10 carbon atoms and free from a carbonyl group, more preferably a linear or branched alkylene group having 1 to 10 carbon atoms and not having a substituent, and still more preferably a methylene group (—$CH_2$—), an ethylene group (—$C_2H_4$—), an isopropylene group (—CH($CH_3$) $CH_2$—), or a propylene group (—$C_3H_6$—).

Any two of $R^{1b}$, $R^{2b}$, $R^{3b}$, and $R^{4b}$ optionally bind to each other to form a ring, but preferably not to form a ring.

In the formula (b), n is an integer of 1 or more. In the formula, n is preferably an integer of 1 to 40, more preferably an integer of 1 to 30, still more preferably an integer of 5 to 25, and particularly preferably an integer of 5 to 9 and 11 to 25.

In the formula (b), p and q are each independently an integer of 0 or more. p is preferably an integer of 0 to 10, more preferably 0 or 1. q is preferably an integer of 0 to 10, more preferably an integer of 0 to 5.

The sum of n, p, and q is preferably an integer of 5 or more. The sum of n, p, and q is more preferably an integer of 8 or more. The sum of n, p, and q is also preferably an integer of 60 or less, more preferably an integer of 50 or less, and still more preferably an integer of 40 or less.

In the formula (b), $X^b$ is H, a metal atom, $NR^{5b}_4$, imidazolium optionally having a substituent, pyridinium optionally having a substituent, or phosphonium optionally having a substituent, wherein $R^{5b}$ is H or an organic group. The four $R^{5b}$ may be the same as or different from each other. $R^{5b}$ is preferably H or an organic group having 1 to 10 carbon atoms, and more preferably H or an organic group having 1 to 4 carbon atoms. Examples of the metal atom include monovalent and divalent metal atoms, and examples thereof include alkali metals (Group 1) and alkaline earth metals (Group 2), and preferred is Na, K or Li. $X^b$ may be a metal atom or $NR^{5b}_4$, wherein $R^{5b}$ is defined as described above.

$X^b$ is preferably H, an alkali metal (Group 1), an alkaline earth metal (Group 2), or $NR^{5b}_4$, more preferably H, Na, K, Li, or $NH_4$ because they are easily dissolved in water, still more preferably Na, K, or $NH_4$ because they are more easily dissolved in water, particularly preferably Na or $NH_4$, and most preferably $NH_4$ because it can be easily removed. When $X^b$ is $NH_4$, the solubility of the surfactant in an aqueous medium is excellent, and the metal component is unlikely to remain in the PTFE or the final product.

In the formula (b), L is a single bond, —$CO_2$—B—*, —OCO—B—*, —$CONR^{6b}$—B—*, —$NR^{6b}CO$—B—*, or —CO— other than the carbonyl groups in —$CO_2$—B—, —OCO—B—, —$CONR^6$—B—, and —$NR^{6b}CO$—B—, wherein B is a single bond or an alkylene group having 1 to 10 carbon atoms and optionally having a substituent, $R^{6b}$ is H or an alkyl group having 1 to 4 carbon atoms and optionally having a substituent. The alkylene group more preferably has 1 to 5 carbon atoms. $R^{6b}$ is more preferably H or a methyl group; and * indicates the side bonded to $-OSO_3X^b$ in the formula.

L is preferably a single bond.

The surfactant (b) is preferably a compound represented by the following formula:

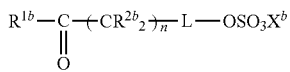

(wherein $R^{1b}$, $R^{2b}$, L, n, and $X^b$ are defined as described above).

The surfactant (b) preferably has a $^1$H-NMR spectrum in which all peak intensities observed in a chemical shift range of 2.0 to 5.0 ppm give an integral value of 10% or higher.

The surfactant (b) preferably has a $^1$H-NMR spectrum in which all peak intensities observed in a chemical shift range of 2.0 to 5.0 ppm give an integral value within the above range. In this case, the surfactant preferably has a ketone structure in the molecule.

The integral value of the surfactant (b) is more preferably 15 or more, and preferably 95 or less, more preferably 80 or less, and still more preferably 70 or less.

The integral value is determined using a heavy water solvent at room temperature. The heavy water content is adjusted to 4.79 ppm.

Examples of the surfactant (b) include:
$CH_3C(O)CH_2CH_2CH_2CH_2CH_2CH_2CH_2CH_2OSO_3Na$,
$CH_3C(O)CH_2CH_2CH_2CH_2CH_2CH_2CH_2CH_2OSO_3Na$,
$CH_3C(O)CH_2CH_2CH_2CH_2CH_2CH_2CH_2OSO_3Na$,
$CH_3C(O)CH_2CH_2CH_2CH_2CH_2CH_2OSO_3Na$,
$CH_3C(O)CH_2CH_2CH_2CH_2CH_2OSO_3Na$,
$CH_3C(O)CH_2CH_2CH_2CH_2OSO_3Na$,
$(CH_3)_3CC(O)CH_2CH_2CH_2CH_2CH_2CH_2CH_2CH_2CH_2OSO_3Na$,
$(CH_3)_2CHC(O)CH_2CH_2CH_2CH_2CH_2CH_2CH_2CH_2CH_2OSO_3Na$,
$(CH_2)_5CHC(O)CH_2CH_2CH_2CH_2CH_2CH_2CH_2CH_2CH_2OSO_3Na$,
$CH_3CH_2C(O)CH_2CH_2CH_2CH_2CH_2CH_2CH_2CH_2OSO_3Na$,
$CH_3CH_2CH_2C(O)CH_2CH_2CH_2CH_2CH_2CH_2CH_2OSO_3Na$,
$CH_3CH_2CH_2CH_2C(O)CH_2CH_2CH_2CH_2CH_2CH_2OSO_3Na$,
$CH_3CH_2CH_2CH_2CH_2C(O)CH_2CH_2CH_2CH_2CH_2OSO_3Na$,
$CH_3CH_2CH_2CH_2CH_2CH_2C(O)CH_2CH_2CH_2CH_2OSO_3Na$,
$CH_3CH_2CH_2CH_2CH_2CH_2CH_2C(O)CH_2CH_2CH_2OSO_3Na$,
$CH_3CH_2CH_2CH_2CH_2CH_2CH_2CH_2C(O)CH_2CH_2OSO_3Na$,
$CH_3CH_2CH_2CH_2CH_2CH_2CH_2CH_2CH_2C(O)CH_2OSO_3Na$,
$CH_3C(O)CH_2CH_2CH_2CH_2CH_2CH_2CH_2CH_2OCH_2OSO_3Na$,
$CH_3C(O)CH_2CH_2CH_2CH_2CH_2CH_2CH_2CH_2C(O)NHCH_2OSO_3Na$,
$CH_3C(O)CH_2CH_2CH_2CH_2CH_2CH_2CH_2CH_2NHC(O)CH_2OSO_3Na$,
$CH_3C(O)CH_2CH_2CH_2CH_2CH_2CH_2CH_2CH_2CH_2C(O)OSO_3Na$,
$CH_3C(O)CH_2CH_2CH_2CH_2CH_2CH_2CH_2CH_2CH_2C(O)OCH_2OSO_3Na$,
$CH_3C(O)CH_2CH_2CH_2CH_2CH_2CH_2CH_2CH_2CH_2OC(O)CH_2OSO_3Na$,
$CH_3C(O)CH_2CH_2CH_2CH_2CH_2CH_2CH_2CH_2CH_2OSO_3H$,
$CH_3C(O)CH_2CH_2CH_2CH_2CH_2CH_2CH_2CH_2CH_2OSO_3Li$,
$CH_3C(O)CH_2CH_2CH_2CH_2CH_2CH_2CH_2CH_2CH_2OSO_3K$,
$CH_3C(O)CH_2CH_2CH_2CH_2CH_2CH_2CH_2CH_2CH_2OSO_3NH_4$,
$CH_3C(O)CH_2CH_2CH_2CH_2CH_2CH_2CH_2CH_2CH(CH_3)_{22}OSO_3Na$,
$CH_3C(O)CH_2CH_2CH_2CH_2CH_2CH_2CH_2CH_2CH_2CH_2CH_2CH_2CH_2CH_2CH_2OSO_3Na$,
$CH_3C(O)CH_2CH_2CH_2CH_2CH_2CH_2CH_2CH_2CH_2CH_2CH_2CH_2CH_2CH_2OSO_3Na$,
$CH_3C(O)CH_2CH_2CH_2CH_2CH_2CH_2CH_2CH_2CH_2CH_2CH_2CH_2CH_2OSO_3Na$,
$CH_3C(O)CH_2CH_2CH_2CH_2CH_2CH_2CH_2CH_2CH_2CH_2CH_2CH_2OSO_3Na$,
$CH_3C(O)CH_2CH_2CH_2CH_2CH_2CH_2CH_2CH_2CH_2CH_2CH_2OSO_3Na$,
$CH_3C(O)CH_2CH_2CH_2CH_2CH_2CH_2CH_2CH_2CH_2CH_2OSO_3Na$,
$CH_3C(O)CH_2CH_2CH_2CH_2CH_2CH_2CH_2CH_2CH_2OSO_3Na$,
$CH_3C(O)CH_2CH_2CH_2CH_2CH_2CH_2CH_2CH_2CH_2CH_2OSO_3Na$,
$(CH_3)_3CC(O)CH_2CH_2CH_2CH_2CH_2CH_2CH_2CH_2CH_2CH_2CH_2CH_2OSO_3Na$,
$(CH_3)_2CHC(O)CH_2CH_2CH_2CH_2CH_2CH_2CH_2CH_2CH_2CH_2CH_2OSO_3Na$,
$(CH_2)_5CHC(O)CH_2CH_2CH_2CH_2CH_2CH_2CH_2CH_2CH_2CH_2CH_2CH_2OSO_3Na$,
$CH_3CH_2C(O)CH_2CH_2CH_2CH_2CH_2CH_2CH_2CH_2CH_2CH_2CH_2CH_2CH_2CH_2OSO_3Na$,
$CH_3CH_2CH_2CH_2CH_2C(O)CH_2CH_2CH_2CH_2CH_2CH_2CH_2CH_2CH_2CH_2CH_2OSO_3Na$,
$CH_3CH_2CH_2CH_2CH_2CH_2CH_2C(O)CH_2CH_2CH_2CH_2CH_2CH_2CH_2CH_2CH_2OSO_3Na$,
$CH_3CH_2CH_2CH_2CH_2CH_2CH_2CH_2CH_2CH_2C(O)CH_2CH_2CH_2CH_2CH_2CH_2CH_2OSO_3Na$,
$CH_3CH_2CH_2CH_2CH_2CH_2CH_2CH_2CH_2CH_2CH_2CH_2C(O)CH_2CH_2CH_2CH_2OSO_3Na$,
$CH_3CH_2C(O)CH_2CH_2CH_2CH_2CH_2CH_2CH_2CH_2CH_2CH_2CH_2CH_2CH_2CH_2OCH_2CH_2OSO_3Na$,
$CH_3CH_2C(O)CH_2CH_2CH_2CH_2CH_2CH_2CH_2CH_2CH_2CH_2CH_2CH_2CH_2CH_2C(O)NHCH_2CH_2OSO_3Na$, CH₃CH₂C(O)
CH₂CH₂CH₂CH₂CH₂CH₂CH₂CH₂CH₂CH₂
CH₂CH₂CH₂CH₂CH₂NHC(O)CH₂CH₂OSO₃Na,
CH₃CH₂C(O)
CH₂CH₂CH₂CH₂CH₂CH₂CH₂CH₂CH₂CH₂
CH₂CH₂CH₂CH₂CH₂C(O)OCH₂CH₂OSO₃Na,
CH₃CH₂C(O)
CH₂CH₂CH₂CH₂CH₂CH₂CH₂CH₂CH₂CH₂
CH₂CH₂CH₂CH₂CH₂OC(O)CH₂CH₂OSO₃Na,
CH₃CH₂C(O)
CH₂CH₂CH₂CH₂CH₂CH₂CH₂CH₂CH₂CH₂
CH₂CH₂CH₂CH₂CH₂CH₂C(O)OSO₃Na,
CH₃CH₂C(O)
CH₂CH₂CH₂CH₂CH₂CH₂CH₂CH₂CH₂CH₂
CH₂CH₂CH₂CH₂CH₂CH₂OSO₃H,
CH₃CH₂C(O)
CH₂CH₂CH₂CH₂CH₂CH₂CH₂CH₂CH₂CH₂
CH₂CH₂CH₂CH₂CH₂CH₂OSO₃Li,
CH₃CH₂C(O)
CH₂CH₂CH₂CH₂CH₂CH₂CH₂CH₂CH₂CH₂
CH₂CH₂CH₂CH₂CH₂CH₂OSO₃K,
CH₃CH₂C(O)CH₂CH₂CH₂CH₂CH₂CH₂CH₂CH₂CH₂CH₂
CH₂CH₂CH₂CH₂CH₂CH₂OSO₃NH₄, and
CH₃C(O)CH₂CH₂CH₂CH₂CH₂CH₂CH₂CH₂CH₂CH₂
CH₂CH₂CH₂CH₂CH₂CH₂CH₂CH₂CH₂CH₂OSO₃Na.

The surfactant (b) is a novel compound, and may be produced by any of the following production methods, for example.

The surfactant (b) may be produced by a production method including:
a step (11b) of hydroxylating a compound (10b) represented by the following formula:

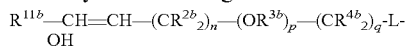

(wherein $R^{2b}$ to $R^{4b}$, n, p, and q are defined as described above; $R^{11b}$ is H, a linear or branched alkyl group having 1 or more carbon atoms and optionally having a substituent, or a cyclic alkyl group having 3 or more carbon atoms and optionally having a substituent, and optionally contains a monovalent or divalent heterocycle or optionally forms a ring when having 3 or more carbon atoms; L is a single bond, —CO₂—B—*, —OCO—B—*, —CONR⁶ᵇ—B—*, —NR⁶ᵇCO—B—*, or —CO— other than the carbonyl groups in —CO₂—B—, —OCO—B—, —CONR⁶ᵇ—B—, and —NR⁶ᵇCO—B—, wherein B is a single bond or an alkylene group having 1 to 10 carbon atoms and optionally having a substituent, $R^{6b}$ is H or an alkyl group having 1 to 4 carbon atoms and optionally having a substituent; * indicates the side bonded to —OH in the formula) to provide a compound (11b) represented by the following formula:

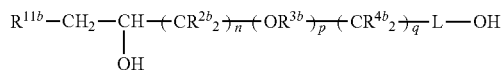

(wherein L, $R^{2b}$ to $R^{4b}$, $R^{11b}$, n, p, and q are defined as described above);
a step (12b) of oxidizing the compound (11b) to provide a compound (12b) represented by the following formula:

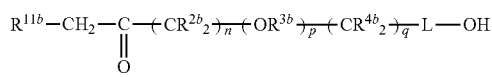

(wherein L, $R^{2b}$ to $R^{4b}$, $R^{11b}$, n, p, and q are defined as described above); and
a step (13b) of sulfuric-esterifying the compound (12b) to provide a compound (13b) represented by the following formula:

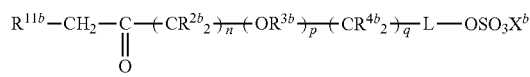

wherein L, $R^{2b}$ to $R^{4b}$, $R^{11b}$, n, p, q, and X b are defined as described above.

The alkyl group for $R^{11b}$ is preferably free from a carbonyl group.

In the alkyl group for $R^{11b}$, 75% or less of the hydrogen atoms bonded to the carbon atoms may be replaced by halogen atoms, 50% or less thereof may be replaced by halogen atoms, or 25% or less thereof may be replaced by halogen atoms. The alkyl group is preferably a non-halogenated alkyl group free from halogen atoms such as fluorine atoms and chlorine atoms.

The alkyl group preferably contains no substituent.

$R^{11b}$ is preferably H, a linear or branched alkyl group having 1 to 9 carbon atoms and optionally having a substituent, or a cyclic alkyl group having 3 to 9 carbon atoms and optionally having a substituent, more preferably H, a linear or branched alkyl group having 1 to 9 carbon atoms and free from a carbonyl group, or a cyclic alkyl group having 3 to 9 carbon atoms and free from a carbonyl group, still more preferably H or a linear or branched alkyl group having 1 to 9 carbon atoms and not having a substituent, further preferably H, a methyl group (—CH₃), or an ethyl group (—C₂H₅), particularly preferably H or a methyl group (—CH₃), and most preferably H.

The hydroxylation in the step (11b) may be performed by a method (1) in which iron(II) phthalocyanine (Fe(Pc)) and sodium borohydride are caused to act on the compound (10b) in an oxygen atmosphere or a method (2) in which isopinocampheylborane (IpcBH₂) is caused to act on the compound (10b) and then the resulting intermediate (dialkyl borane) is oxidized.

In the method (1), iron(II) phthalocyanine may be used in a catalytic amount, and may be used in an amount of 0.001 to 1.2 mol based on 1 mol of the compound (10b).

In the method (1), sodium borohydride may be used in an amount of 0.5 to 20 mol based on 1 mol of the compound (10b).

The reaction in the method (1) may be performed in a solvent. The solvent is preferably an organic solvent, and examples thereof include ethers, halogenated hydrocarbons, aromatic hydrocarbons, nitriles, and nitrogen-containing polar organic compounds.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

Examples of the nitrile include acetonitrile, propionitrile, butyronitrile, isobutyronitrile, and benzonitrile, of which acetonitrile is preferred.

Examples of the nitrogen-containing polar organic compound include N,N-dimethylformamide, N,N-dimethylacetamide, N-methyl-2-pyrrolidone, 2-pyrrolidone, and 1,3-dimethyl-2-imidazolidinone, of which N,N-dimethylformamide, N,N-dimethylacetamide, and N-methyl-2-pyrrolidone are preferred.

The reaction temperature in the method (1) is preferably −78 to 200° C., and more preferably 0 to 150° C.

The reaction pressure in the method (1) is preferably 0 to 5.0 MPa, and more preferably 0.1 to 1.0 MPa.

The reaction duration in the method (1) is preferably 0.1 to 72 hours, and more preferably 0.1 to 48 hours.

In the method (2), isopinocampheylborane may be used in an amount of 1.0 to 10.0 mol based on 1 mol of the compound (10b).

The reaction of the compound (10b) and isopinocampheylborane may be performed in a solvent. The solvent is preferably an organic solvent, and examples thereof include ethers, halogenated hydrocarbons, and aromatic hydrocarbons.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

The reaction temperature of the compound (10b) and isopinocampheylborane is preferably −78 to 200° C., and more preferably 0 to 150° C.

The reaction pressure of the compound (10b) and isopinocampheylborane is preferably 0 to 5.0 MPa, and more preferably 0.1 to 1.0 MPa.

The duration of the reaction of the compound (10b) and isopinocampheylborane is preferably 0.1 to 72 hours, and more preferably 0.1 to 48 hours.

The oxidation in the method (2) may be performed by causing an oxidizing agent to act on the intermediate. An example of the oxidizing agent is hydrogen peroxide. The oxidizing agent may be used in an amount of 0.7 to 10 mol based on 1 mol of the intermediate.

The oxidation in the method (2) may be performed in a solvent. Examples of the solvent include water, methanol, and ethanol, of which water is preferred.

The oxidation temperature in the method (2) is preferably 0 to 100° C., and more preferably 0 to 80° C.

The oxidation pressure in the method (2) is preferably 0 to 5.0 MPa, and more preferably 0.1 to 1.0 MPa.

The oxidation duration in the method (2) is preferably 0.1 to 72 hours, and more preferably 0.1 to 48 hours.

Examples of the method of oxidizing the compound (11b) in the step (12b) include (a) a method of using Jones reagent ($CrO_3/H_2SO_4$) (Jones oxidation), (b) a method of using Dess-Martin periodinane (DMP) (Dess-Martin oxidation), (c) a method of using pyridinium chlorochromate (PCC), (d) a method of causing a bleaching agent (about 5% to 6% aqueous solution of NaOCl) to act in the presence of a nickel compound such as $NiCl_2$, and (e) a method of causing a hydrogen acceptor such as an aldehyde or a ketone to act in the presence of an aluminum catalyst such as $Al(CH_3)_3$ or $Al[OCH(CH_3)_2]_3$ (Oppenauer oxidation).

The oxidation in the step (12b) may be performed in a solvent. The solvent is preferably water or an organic solvent, and examples thereof include water, ketones, ethers, halogenated hydrocarbons, aromatic hydrocarbons, and nitriles.

Examples of the ketones include acetone, methyl ethyl ketone, methyl isobutyl ketone, cyclohexanone, and diacetone alcohol, of which acetone is preferred.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

Examples of the nitrile include acetonitrile, propionitrile, butyronitrile, isobutyronitrile, and benzonitrile, of which acetonitrile is preferred.

The oxidation temperature in the step (12b) is preferably −78 to 200° C., and may appropriately be selected in accordance with the method used.

The oxidation pressure in the step (12b) is preferably 0 to 5.0 MPa, and may appropriately be selected in accordance with the method used.

The oxidation duration in the step (12b) is preferably 0.1 to 72 hours, and may appropriately be selected in accordance with the method used.

The sulfuric-esterification in the step (13b) may be performed by reacting the compound (12b) and a sulfating reagent. Examples of the sulfating reagent include sulfur trioxide amine complexes such as a sulfur trioxide pyridine complex, a sulfur trioxide trimethylamine complex, and a sulfur trioxide triethylamine complex, sulfur trioxide amide complexes such as a sulfur trioxide dimethylformamide complex, sulfuric acid-dicyclohexylcarbodiimide, chlorosulfuric acid, concentrated sulfuric acid, and sulfamic acid. The amount of the sulfating reagent used is preferably 0.5 to 10 mol, more preferably 0.5 to 5 mol, and still more preferably 0.7 to 4 mol, based on 1 mol of the compound (12b).

The sulfuric-esterification in the step (13b) may be performed in a solvent. The solvent is preferably an organic solvent, and examples thereof include ethers, halogenated hydrocarbons, aromatic hydrocarbons, pyridines, dimethyl sulfoxide, sulfolane, and nitriles.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

Examples of the nitrile include acetonitrile, propionitrile, butyronitrile, isobutyronitrile, and benzonitrile, of which acetonitrile is preferred.

The sulfuric-esterification temperature in the step (13b) is preferably −78 to 200° C., and more preferably −20 to 150° C.

The sulfuric-esterification pressure in the step (13b) is preferably 0 to 10 MPa, and more preferably 0.1 to 5 MPa.

The sulfuric-esterification duration in the step (13b) is preferably 0.1 to 72 hours, and more preferably 0.1 to 48 hours.

The surfactant (b) may also be produced by a production method including a step (21b) of ozonolyzing a compound (20b) represented by the following formula:

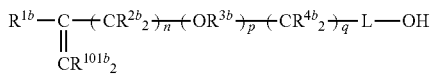

(wherein L, $R^{1b}$ to $R^{4b}$, n, p, and q are defined as described above; and $R^{101b}$ is an organic group) to provide a compound (21b) represented by the following formula:

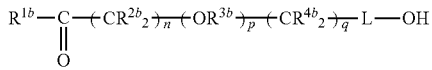

(wherein L, $R^{1b}$ to $R^{4b}$, n, p, and q are defined as described above); and a step (22b) of sulfuric-esterifying the compound (21b) to provide a compound (22b) represented by the following formula:

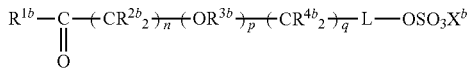

(wherein L, $R^{1b}$ to $R^{4b}$, n, p, q, and $X^b$ are defined as described above).

$R^{101b}$ is preferably an alkyl group having 1 to 20 carbon atoms. The two $R^{101b}$ may be the same as or different from each other.

The ozonolysis in the step (21b) may be performed by causing ozone to act on the compound (20b), followed by post-treatment with a reducing agent.

The ozone may be generated by dielectric barrier discharge in oxygen gas.

Examples of the reducing agent used in the post-treatment include zinc, dimethyl sulfide, thiourea, and phosphines, of which phosphines are preferred.

The ozonolysis in the step (21b) may be performed in a solvent. The solvent is preferably water or an organic solvent, and examples thereof include water, alcohols, carboxylic acids, ethers, halogenated hydrocarbons, and aromatic hydrocarbons.

Examples of the alcohol include methanol, ethanol, 1-propanol, and isopropanol. Of these, methanol and ethanol are preferred.

Examples of the carboxylic acids include acetic acid and propionic acid. Of these, acetic acid is preferred.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

The ozonolysis temperature in the step (21b) is preferably −78 to 200° C., and more preferably 0 to 150° C.

The ozonolysis pressure in the step (21b) is preferably 0 to 5.0 MPa, and more preferably 0.1 to 1.0 MPa.

The ozonolysis duration in the step (21b) is preferably 0.1 to 72 hours, and more preferably 0.1 to 48 hours.

The sulfate esterification in the step (22b) may be performed by reacting the compound (21b) and the sulfating reagent under the same conditions as in the sulfuric-esterification in the step (13b).

The surfactant (b) may also be produced by a production method including:

a step (31b) of epoxidizing a compound (30b) represented by the formula:

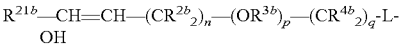

(wherein L, $R^{2b}$ to $R^{4b}$, n, p, and q are defined as described above; $R^{21b}$ is H, a linear or branched alkyl group having 1 or more carbon atoms and optionally having a substituent, or a cyclic alkyl group having 3 or more carbon atoms and optionally having a substituent, and optionally contains a monovalent or divalent heterocycle or optionally forms a ring when having 3 or more carbon atoms) to provide a compound (31b) represented by the following formula:

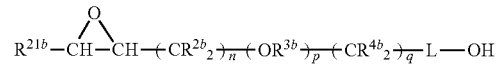

(wherein L, $R^{2b}$ to $R^{4b}$, $R^{21b}$, n, p, and q are defined as described above);

a step (32b) of reacting the compound (31b) with a lithium dialkylcopper represented by $R^{22b}{}_2CuLi$ (wherein $R^{22b}$ is a linear or branched alkyl group having 1 or more carbon atoms and optionally having a substituent or a cyclic alkyl group having 3 or more carbon atoms and optionally having a substituent, and optionally contains a monovalent or divalent heterocycle or optionally forms a ring when having 3 or more carbon atoms) to provide a compound (32b) represented by the following formula:

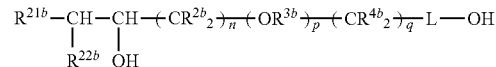

(wherein L, $R^{2b}$ to $R^{4b}$, $R^{21b}$, $R^{22b}$, n, p, and q are defined as described above);

a step (33b) of oxidizing the compound (32b) to provide a compound (33b) represented by the following formula:

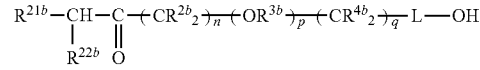

(wherein L, $R^{2b}$ to $R^{4b}$, $R^{21b}$, $R^{22b}$, n, p, and q are defined as described above); and a step (33b) of sulfuric-esterifying a compound (33b) to provide a compound (34b) represented by the following formula:

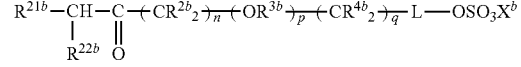

(wherein L, $R^{2b}$ to $R^{4b}$, L, $R^{21b}$, $R^{22b}$, n, p, q, and X b are defined as described above).

The alkyl group for $R^{21b}$ is preferably free from a carbonyl group.

In the alkyl group for $R^{21b}$, 75% or less of the hydrogen atoms bonded to the carbon atoms may be replaced by halogen atoms, 50% or less thereof may be replaced by halogen atoms, or 25% or less thereof may be replaced by halogen atoms. The alkyl group is preferably a non-halogenated alkyl group free from halogen atoms such as fluorine atoms and chlorine atoms.

The alkyl group preferably contains no substituent.

$R^{21b}$ is preferably H, a linear or branched alkyl group having 1 to 8 carbon atoms and optionally having a substituent, or a cyclic alkyl group having 3 to 8 carbon atoms and optionally having a substituent, more preferably H, a linear or branched alkyl group having 1 to 8 carbon atoms and free from a carbonyl group, or a cyclic alkyl group having 3 to 8 carbon atoms and free from a carbonyl group, still more preferably H or a linear or branched alkyl group having 1 to 8 carbon atoms and not having a substituent, particularly preferably H or a methyl group (—$CH_3$), and most preferably H.

The alkyl group for $R^{22b}$ is preferably free from a carbonyl group.

In the alkyl group for $R^{22b}$, 75% or less of the hydrogen atoms bonded to the carbon atoms may be replaced by halogen atoms, 50% or less thereof may be replaced by halogen atoms, or 25% or less thereof may be replaced by halogen atoms. The alkyl group is preferably a non-halogenated alkyl group free from halogen atoms such as fluorine atoms and chlorine atoms.

The alkyl group preferably contains no substituent.

$R^{22b}$ is preferably a linear or branched alkyl group having 1 to 9 carbon atoms and optionally having a substituent or a cyclic alkyl group having 3 to 9 carbon atoms and optionally having a substituent, more preferably a linear or branched alkyl group having 1 to 9 carbon atoms and free from a carbonyl group or a cyclic alkyl group having 3 to 9 carbon atoms and free from a carbonyl group, still more preferably a linear or branched alkyl group having 1 to 9 carbon atoms and not having a substituent, particularly preferably a methyl group (—$CH_3$) or an ethyl group (—$C_2H_5$), and most preferably a methyl group (—$CH_3$).

The two $R^{22b}$ may be the same as or different from each other.

The total number of carbon atoms of $R^{21b}$ and $R^{22b}$ is preferably 1 to 7, more preferably 1 to 2, and most preferably 1.

The epoxidation in the step (31b) may be performed by causing an epoxidizing agent to act on the compound (30b).

Examples of the epoxidizing agent include peroxy acids such as meta-chloroperbenzoic acid (m-CPBA), perbenzoic acid, hydrogen peroxide, and tert-butyl hydroperoxide, dimethyl dioxolane, and methyl trifluoromethyl dioxolane, of which peroxy acids are preferred, and meta-chloroperbenzoic acid is more preferred.

The epoxidizing agent may be used in an amount of 0.5 to 10.0 mol based on 1 mol of the compound (30b).

The epoxidation in the step (31b) may be performed in a solvent. The solvent is preferably an organic solvent, and examples thereof include ketones, ethers, halogenated hydrocarbons, aromatic hydrocarbons, nitriles, pyridines, nitrogen-containing polar organic compounds, and dimethyl sulfoxide, of which dichloromethane is preferred.

Examples of the ketones include acetone, methyl ethyl ketone, methyl isobutyl ketone, cyclohexanone, and diacetone alcohol, of which acetone is preferred.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

Examples of the nitrile include acetonitrile, propionitrile, butyronitrile, isobutyronitrile, and benzonitrile, of which acetonitrile is preferred.

Examples of the nitrogen-containing polar organic compound include N,N-dimethylformamide, N,N-dimethylacetamide, N-methyl-2-pyrrolidone, 2-pyrrolidone, and 1,3-dimethyl-2-imidazolidinone, of which N,N-dimethylformamide, N,N-dimethylacetamide, and N-methyl-2-pyrrolidone are preferred.

The epoxidation temperature in the step (31b) is preferably −78 to 200° C., and more preferably −40 to 150° C.

The epoxidation pressure in the step (31b) is preferably 0 to 5.0 MPa, and more preferably 0.1 to 1.0 MPa.

The epoxidation duration in the step (31b) is preferably 0.1 to 72 hours, and more preferably 0.1 to 48 hours.

In the step (32b), the lithium dialkylcopper may be used in an amount of 0.5 to 10.0 mol based on 1 mol of the compound (31b).

The reaction in the step (32b) may be performed in a solvent. The solvent is preferably an organic solvent, and examples thereof include ethers, halogenated hydrocarbons, and aromatic hydrocarbons.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

The reaction temperature in the step (32b) is preferably −78 to 200° C., and more preferably −40 to 150° C.

The reaction pressure in the step (32b) is preferably 0 to 5.0 MPa, and more preferably 0.1 to 1.0 MPa.

The reaction duration in the step (32b) is preferably 0.1 to 72 hours, and more preferably 0.1 to 48 hours.

Examples of the method of oxidizing the compound (32b) in the step (33b) include (a) a method of using Jones reagent ($CrO_3/H_2SO_4$) (Jones oxidation), (b) a method of using Dess-Martin periodinane (DMP) (Dess-Martin oxidation), (c) a method of using pyridinium chlorochromate (PCC), (d) a method of causing a bleaching agent (about 5% to 6% aqueous solution of NaOCl) to act in the presence of a nickel compound such as $NiCl_2$, and (e) a method of causing a hydrogen acceptor such as an aldehyde or a ketone to act in the presence of an aluminum catalyst such as $Al(CH_3)_3$ or $Al[OCH(CH_3)_2]_3$ (Oppenauer oxidation).

The oxidation in the step (33b) may be performed in a solvent. The solvent is preferably water or an organic solvent, and examples thereof include water, ketones, alcohols, ethers, halogenated hydrocarbons, aromatic hydrocarbons, and nitriles.

Examples of the ketones include acetone, methyl ethyl ketone, methyl isobutyl ketone, cyclohexanone, and diacetone alcohol, of which acetone is preferred.

Examples of the alcohol include methanol, ethanol, 1-propanol, and isopropanol. Of these, methanol and ethanol are preferred.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

Examples of the nitrile include acetonitrile, propionitrile, butyronitrile, isobutyronitrile, and benzonitrile, of which acetonitrile is preferred.

The oxidation temperature in the step (33b) is preferably −78 to 200° C., and may appropriately be selected in accordance with the method used.

The oxidation pressure in the step (33b) is preferably 0 to 5.0 MPa, and may appropriately be selected in accordance with the method used.

The oxidation duration in the step (33b) is preferably 0.1 to 72 hours, and may appropriately be selected in accordance with the method used.

The sulfate esterification in the step (34b) may be performed by reacting the compound (33b) and the sulfating reagent under the same conditions as in the sulfuric-esterification in the step (13b).

The surfactant (b) may also be produced by a production method including:

a step (41b) of oxidizing the compound (10b) represented by the following formula:

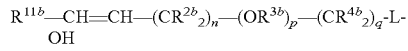

(wherein L, $R^{2b}$ to $R^{4b}$, $R^{11b}$, n, p, and q are defined as described above) to provide a compound (41b) represented by the following formula:

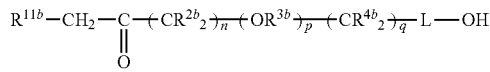

(wherein L, $R^{2b}$ to $R^{4b}$, L, $R^{11b}$, n, p, and q are defined as described above); and a step (42b) of sulfuric-esterifying the compound (41b) to provide a compound (42b) represented by the following formula:

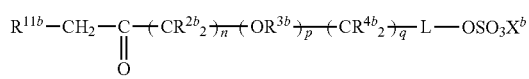

(wherein L, $R^{2b}$ to $R^{4b}$, $R^{11b}$, n, p, q, and $X^b$ are defined as described above).

The oxidation in the step (41b) may be performed by causing an oxidizing agent to act on the compound (10b) in the presence of water and a palladium compound.

Examples of the oxidizing agent include monovalent or divalent copper salts such as copper chloride, copper acetate, copper cyanide, and copper trifluoromethanethiolate, iron salts such as iron chloride, iron acetate, iron cyanide, iron trifluoromethanethiolate, and hexacyanoferrates, benzoquinones such as 1,4-benzoquinone, 2,3-dichloro-5,6-dicyano-1,4-benzoquinone, tetrachloro-1,2-benzoquinone, and tetrachloro-1,4-benzoquinone, $H_2O_2$, $MnO_2$, $KMnO_4$, $RuO_4$, m-chloroperbenzoic acid, and oxygen. Of these, copper salts, iron salts, and benzoquinones are preferred, and copper chloride, iron chloride, and 1,4-benzoquinone are more preferred.

The oxidizing agent may be used in an amount of 0.001 to 10 mol based on 1 mol of the compound (10b).

The water may be used in an amount of 0.5 to 1,000 mol based on 1 mol of the compound (10b).

An example of the palladium compound is palladium dichloride. The palladium compound may be used in a catalytic amount, and may be used in an amount of 0.0001 to 1.0 mol based on 1 mol of the compound (10b).

The oxidation in the step (41b) may be performed in a solvent. Examples of the solvent include water, esters, aliphatic hydrocarbons, aromatic hydrocarbons, alcohols, carboxylic acids, ethers, halogenated hydrocarbons, nitrogen-containing polar organic compounds, nitriles, dimethyl sulfoxide, and sulfolane.

Examples of the esters include ethyl acetate, butyl acetate, ethylene glycol monomethyl ether acetate, and propylene glycol monomethyl ether acetate (PGMEA, also known as 1-methoxy-2-acetoxypropane), of which ethyl acetate is preferred.

Examples of the aliphatic hydrocarbons include hexane, cyclohexane, heptane, octane, nonane, decane, undecane, dodecane, and mineral spirits, of which cyclohexane and heptane are preferred.

Examples of the aromatic hydrocarbon include benzene, toluene, and xylene, of which benzene and toluene are preferred.

Examples of the alcohol include methanol, ethanol, 1-propanol, and isopropanol.

Examples of the carboxylic acids include acetic acid and propionic acid. Of these, acetic acid is preferred.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the nitrogen-containing polar organic compound include N,N-dimethylformamide, N,N-dimethylacetamide, N-methyl-2-pyrrolidone, 2-pyrrolidone, and 1,3-dimethyl-2-imidazolidinone, of which N,N-dimethylformamide, N,N-dimethylacetamide, and N-methyl-2-pyrrolidone are preferred.

Examples of the nitrile include acetonitrile, propionitrile, butyronitrile, isobutyronitrile, and benzonitrile, of which acetonitrile is preferred.

The oxidation temperature in the step (41b) is preferably −78 to 200° C., and more preferably −20 to 150° C.

The oxidation pressure in the step (41b) is preferably 0 to 10 MPa, and more preferably 0.1 to 5.0 MPa.

The oxidation duration in the step (41b) is preferably 0.1 to 72 hours, and more preferably 0.1 to 48 hours.

The sulfate esterification in the step (42b) may be performed by reacting the compound (41b) and the sulfating reagent under the same conditions as in the sulfuric-esterification in the step (13b).

The surfactant (b) may also be produced by a production method including:

a step (51) of reacting a compound (50) represented by the following formula:

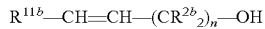

(wherein $R^{2b}$, $R^{11b}$, and n are defined as described above) and a halogenating agent to provide a compound (51) represented by the following formula:

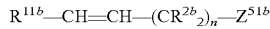

(wherein $R^{2b}$, $R^{11b}$, and n are defined as described above; and $Z^{51b}$ is a halogen atom);

a step (52) of reacting the compound (51) and an alkylene glycol represented by HO—$R^{3b}$-L-OH (wherein L and $R^{3b}$ are defined as described above) to provide a compound (52) represented by the following formula:

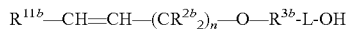

(wherein L, $R^{2b}$, $R^{3b}$, $R^{11b}$, and n are defined as described above);

a step (53) of oxidizing the compound (52) to provide a compound (53) represented by the following formula:

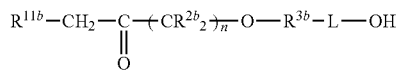

(wherein L, $R^{2b}$, $R^{3b}$, $R^{11b}$, and n are defined as described above); and a step (54) of sulfuric-esterifying the compound (53) to provide a compound (54) represented by the following formula:

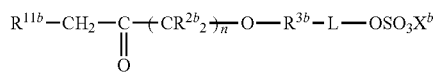

(wherein L, $R^{2b}$, $R^{3b}$, $R^{11b}$, n, and $X^b$ are defined as described above).

$Z^{51b}$ is preferably F, Cl, Br or I, and more preferably Br.

Examples of the halogenating agent used in the step (51) include N-bromosuccinimide and N-chlorosuccinimide.

The halogenating agent may be used in an amount of 0.5 to 10.0 mol based on 1 mol of the compound (50).

The reaction of step (51) may be performed in the presence of phosphines such as triphenylphosphine.

The phosphines may be used in an amount of 0.5 to 10.0 mol based on 1 mol of the compound (50).

The reaction in the step (51) may be performed in a solvent. The solvent is preferably an organic solvent, and examples thereof include ethers, halogenated hydrocarbons, and aromatic hydrocarbons.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

The reaction temperature in the step (51) is preferably −78 to 200° C., and more preferably −40 to 150° C.

The reaction pressure in the step (51) is preferably 0 to 5.0 MPa, and more preferably 0.1 to 1.0 MPa.

The reaction duration in the step (51) is preferably 0.1 to 72 hours, and more preferably 0.1 to 48 hours.

In the step (52), the alkylene glycol may be used in an amount of 0.5 to 10.0 mol based on 1 mol of the compound (51).

The reaction in the step (52) may be performed in the presence of a base. Examples of the base include sodium hydride, sodium hydroxide, and potassium hydroxide.

The base may be used in an amount of 0.5 to 10.0 mol based on 1 mol of the compound (51).

The reaction in the step (52) may be performed in a solvent. The solvent is preferably an organic solvent, and examples thereof include nitrogen-containing polar organic compounds, ethers, halogenated hydrocarbons, and aromatic hydrocarbons.

Examples of the nitrogen-containing polar organic compound include N,N-dimethylformamide, N,N-dimethylacetamide, N-methyl-2-pyrrolidone, 2-pyrrolidone, and 1,3-dimethyl-2-imidazolidinone, of which N,N-dimethylformamide, N,N-dimethylacetamide, and N-methyl-2-pyrrolidone are preferred.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

The reaction temperature in the step (52) is preferably −78 to 200° C., and more preferably −40 to 150° C.

The reaction pressure in the step (52) is preferably 0 to 5.0 MPa, and more preferably 0.1 to 1.0 MPa.

The reaction duration in the step (52) is preferably 0.1 to 72 hours, and more preferably 0.1 to 48 hours.

The oxidation in the step (53) may be performed by causing an oxidizing agent to act on the compound (52) in the presence of water and a palladium compound under the same conditions as in the oxidation in the step (41).

The sulfate esterification in the step (54) may be performed by reacting the compound (53) and the sulfating reagent under the same conditions as in the sulfuric-esterification in the step (13).

In any of the production methods described above, after the completion of each step, the solvent may be distilled off, or distillation, purification or the like may be performed to increase the purity of the resulting compounds. Further, when the obtained compound has a group represented by —$OSO_3H$ (that is, when $X^b$ is H), the compounds may be brought into contact with an alkali such as sodium carbonate or ammonia to covert —$OSO_3H$ into a sulfate group.

Among the methods for producing the surfactant (b), production methods including the steps (41b) and (42b) are preferred.

The surfactant (c) will be described.

In the formula (c), $R^{1c}$ is a linear or branched alkyl group having 1 or more carbon atoms or a cyclic alkyl group having 3 or more carbon atoms.

When having 3 or more carbon atoms, the alkyl group optionally contains a carbonyl group (—C(=O)—) between two carbon atoms. When having 2 or more carbon atoms, the alkyl group optionally contains the carbonyl group at an end of the alkyl group. In other words, acyl groups such as an acetyl group represented by $CH_3—C(=O)—$ are also included in the alkyl group.

When having 3 or more carbon atoms, the alkyl group optionally contains a monovalent or divalent heterocycle, or optionally forms a ring. The heterocycle is preferably an unsaturated heterocycle, more preferably an oxygen-containing unsaturated heterocycle, and examples thereof include a furan ring. In $R^{1c}$, a divalent heterocycle may be present between two carbon atoms, or a divalent heterocycle may be present at an end and bind to $—C(=O)—$, or a monovalent heterocycle may be present at an end of the alkyl group.

The "number of carbon atoms" in the alkyl group as used herein includes the number of carbon atoms constituting the carbonyl groups and the number of carbon atoms constituting the heterocycles. For example, the number of carbon atoms in the group represented by $CH_3—C(=O)—CH_2—$ is 3, the number of carbon atoms in the group represented by $CH_3—C(=O)—C_2H_4—C(=O)—C_2H_4—$ is 7, and the number of carbon atoms in the group represented by $CH_3—C(=O)—$ is 2.

In the alkyl group, a hydrogen atom bonded to a carbon atom may be replaced by a functional group such as a hydroxy group (—OH) or a monovalent organic group containing an ester bond. Still, it is preferably not replaced by any functional group.

An example of the monovalent organic group containing an ester bond is a group represented by the formula: $—O—C(=O)—R^{101c}$, wherein $R^{101c}$ is an alkyl group.

In the alkyl group, 75% or less of the hydrogen atoms bonded to the carbon atoms may be replaced by halogen atoms, 50% or less thereof may be replaced by halogen atoms, or 25% or less thereof may be replaced by halogen atoms. The alkyl group is preferably a non-halogenated alkyl group free from halogen atoms such as fluorine atoms and chlorine atoms.

In the formula (c), $R^{2c}$ and $R^{3c}$ are each independently a single bond or a divalent linking group.

Preferably, $R^{2c}$ and $R^{3c}$ are each independently a single bond, a linear or branched alkylene group having 1 or more carbon atoms, or a cyclic alkylene group having 3 or more carbon atoms.

The alkylene group constituting $R^{2c}$ and $R^{3c}$ is preferably free from a carbonyl group.

In the alkylene group, a hydrogen atom bonded to a carbon atom may be replaced by a functional group such as a hydroxy group (—OH) or a monovalent organic group containing an ester bond. Still, it is preferably not replaced by any functional group.

An example of the monovalent organic group containing an ester bond is a group represented by the formula: $—O—C(=O)—R^{102c}$, wherein $R^{102c}$ is an alkyl group.

In the alkylene group, 75% or less of the hydrogen atoms bonded to the carbon atoms may be replaced by halogen atoms, 50% or less thereof may be replaced by halogen atoms, or 25% or less thereof may be replaced by halogen atoms. The alkylene group is preferably a non-halogenated alkylene group free from halogen atoms such as fluorine atoms and chlorine atoms.

The total number of carbon atoms of $R^{1c}$, $R^{2c}$, and $R^{3c}$ is 5 or more. The total number of carbon atoms is preferably 7 or more, more preferably 9 or more, and preferably 20 or less, more preferably 18 or less, still more preferably 15 or less.

Any two of $R^{1c}$, $R^{2c}$, and $R^{3c}$ optionally bind to each other to form a ring.

In the formula (c), $A^c$ is $—COOX^c$ or $—SO_3X^c$, wherein $X^c$ is H, a metal atom, $NR^{4c}_4$, imidazolium optionally having a substituent, pyridinium optionally having a substituent, or phosphonium optionally having a substituent, wherein $R^{4c}$ is H or an organic group and may be the same or different. $R^{4c}$ is preferably H or an organic group having 1 to 10 carbon atoms, and more preferably H or an organic group having 1 to 4 carbon atoms. Examples of the metal atom include monovalent and divalent metal atoms, and examples thereof include alkali metals (Group 1) and alkaline earth metals (Group 2), and preferred is Na, K or Li.

$X^c$ is preferably H, an alkali metal (Group 1), an alkaline earth metal (Group 2), or $NR^{4c}_4$, more preferably H, Na, K, Li, or $NH_4$ because they are easily dissolved in water, still more preferably Na, K, or $NH_4$ because they are more easily dissolved in water, particularly preferably Na or $NH_4$, and most preferably $NH_4$ because it can be easily removed. When $X^c$ is $NH_4$, the solubility of the surfactant in an aqueous medium is excellent, and the metal component is unlikely to remain in the PTFE or the final product.

$R^{1c}$ is preferably a linear or branched alkyl group having 1 to 8 carbon atoms and free from a carbonyl group, a cyclic alkyl group having 3 to 8 carbon atoms and free from a carbonyl group, a linear or branched alkyl group having 2 to 45 carbon atoms and containing 1 to 10 carbonyl groups, a cyclic alkyl group having 3 to 45 carbon atoms and containing a carbonyl group, or an alkyl group having 3 to 45 carbon atoms and containing a monovalent or divalent heterocycle.

$R^{1c}$ is more preferably a group represented by the following formula:

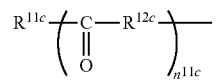

wherein $n^{11c}$ is an integer of 0 to 10; $R^{11c}$ is a linear or branched alkyl group having 1 to 5 carbon atoms or a cyclic alkyl group having 3 to 5 carbon atoms; $R^{12c}$ is an alkylene group having 0 to 3 carbon atoms; and when $n^{11c}$ is an integer of 2 to 10, each $R^{12c}$ may be the same or different.

In the formula, $n^{11c}$ is preferably an integer of 0 to 5, more preferably an integer of 0 to 3, and still more preferably an integer of 1 to 3.

The alkyl group for $R^{11c}$ is preferably free from a carbonyl group.

In the alkyl group for $R^{11c}$, a hydrogen atom bonded to a carbon atom may be replaced by a functional group such as a hydroxy group (—OH) or a monovalent organic group containing an ester bond. Still, it is preferably not replaced by any functional group.

An example of the monovalent organic group containing an ester bond is a group represented by the formula: $—O—C(=O)—R^{103c}$, wherein $R^{103c}$ is an alkyl group.

In the alkyl group for $R^{11b}$, 75% or less of the hydrogen atoms bonded to the carbon atoms may be replaced by halogen atoms, 50% or less thereof may be replaced by halogen atoms, or 25% or less thereof may be replaced by halogen atoms. The alkyl group is preferably a non-halogenated alkyl group free from halogen atoms such as fluorine atoms and chlorine atoms.

$R^{12c}$ is an alkylene group having 0 to 3 carbon atoms. The alkylene group preferably has 1 to 3 carbon atoms.

The alkylene group for $R^{12c}$ may be either linear or branched.

The alkylene group for $R^{12c}$ is preferably free from a carbonyl group. $R^{12c}$ is more preferably an ethylene group ($—C_2H_4—$) or a propylene group ($—C_3H_6—$).

In the alkylene group for $R^{12c}$, a hydrogen atom bonded to a carbon atom may be replaced by a functional group such as a hydroxy group (—OH) or a monovalent organic group containing an ester bond. Still, it is preferably not replaced by any functional group.

An example of the monovalent organic group containing an ester bond is a group represented by the formula: $—O—C(=O)—R^{104c}$, wherein $R^{104c}$ is an alkyl group.

In the alkylene group for $R^{12c}$, 75% or less of the hydrogen atoms bonded to the carbon atoms may be replaced by halogen atoms, 50% or less thereof may be replaced by halogen atoms, or 25% or less thereof may be replaced by halogen atoms. The alkylene group is preferably a non-halogenated alkylene group free from halogen atoms such as fluorine atoms and chlorine atoms.

$R^{2c}$ and $R^{3c}$ are preferably each independently an alkylene group having 1 or more carbon atoms and free from a carbonyl group, more preferably an alkylene group having 1 to 3 carbon atoms and free from a carbonyl group, and still more preferably an ethylene group ($—C_2H_4—$) or a propylene group ($—C_3H_6—$).

Examples of the surfactant (c) include the following surfactants. In each formula, $A^c$ is defined as described above.

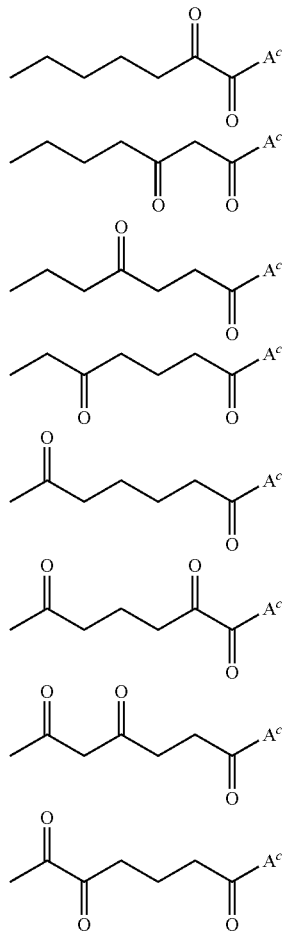

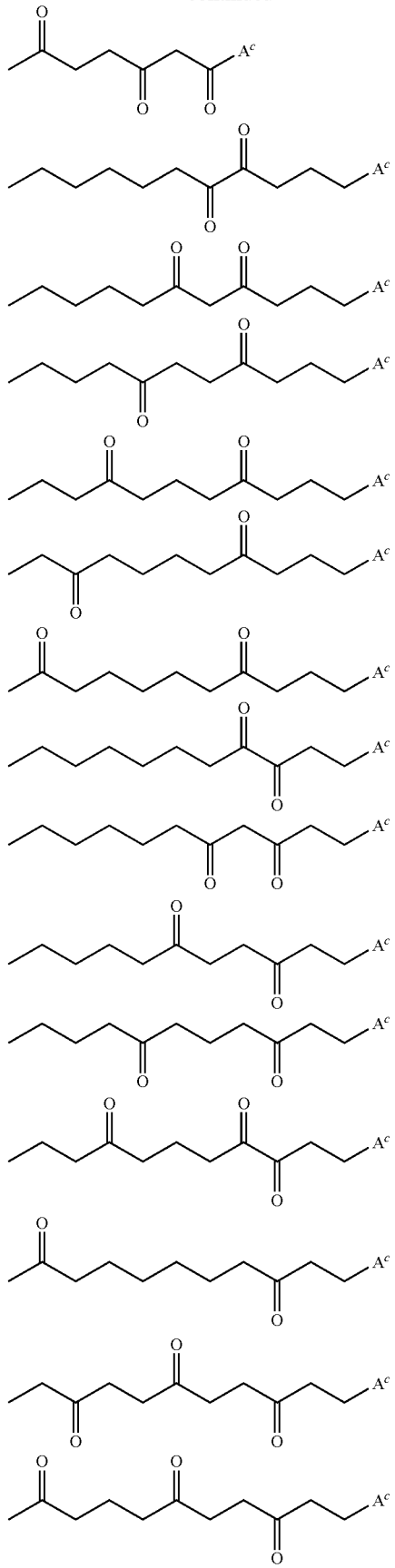

103
-continued
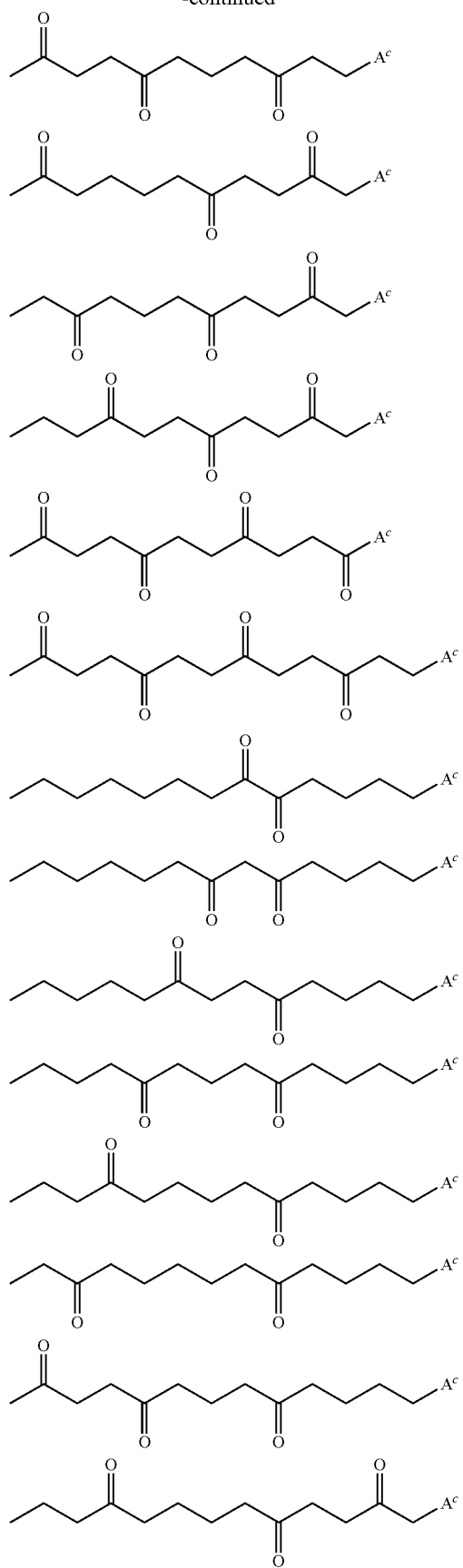
104
-continued
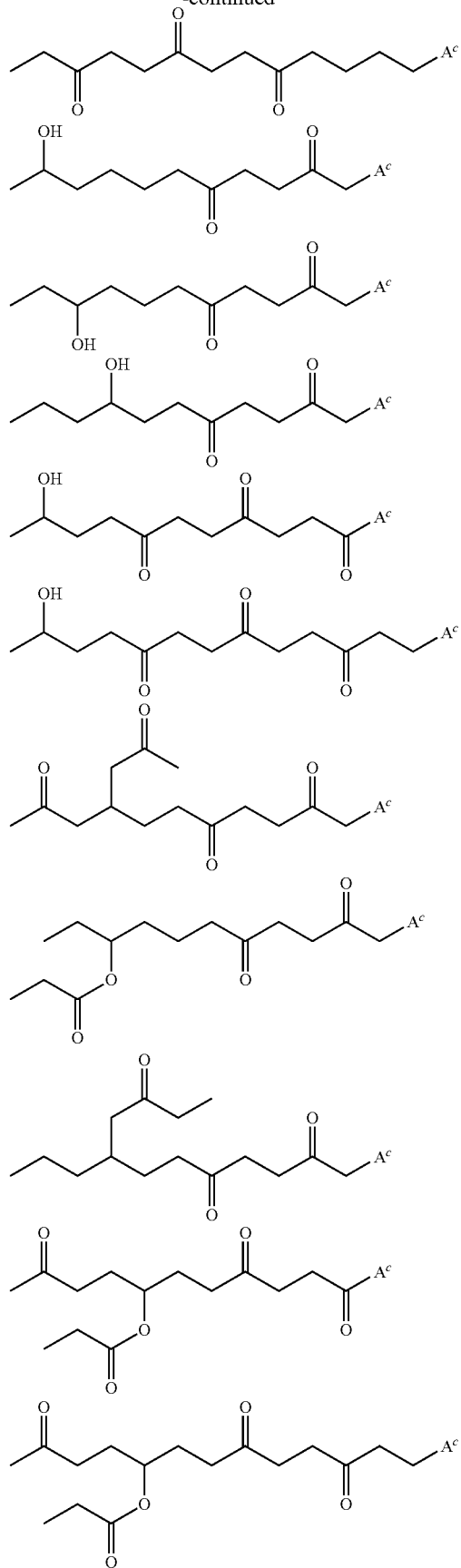

-continued
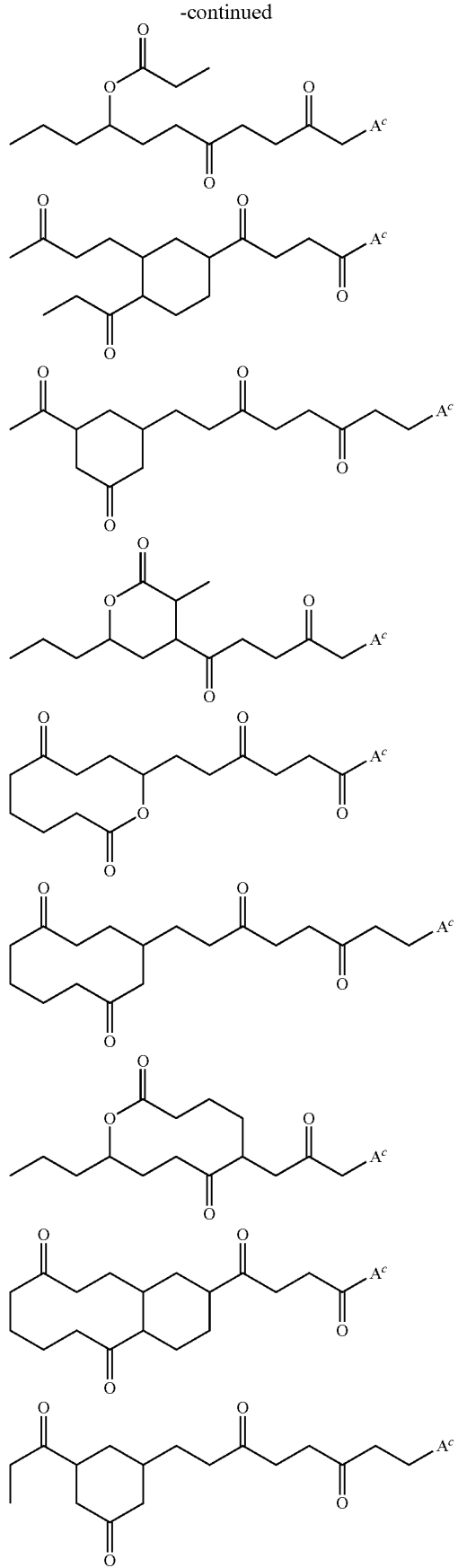
-continued
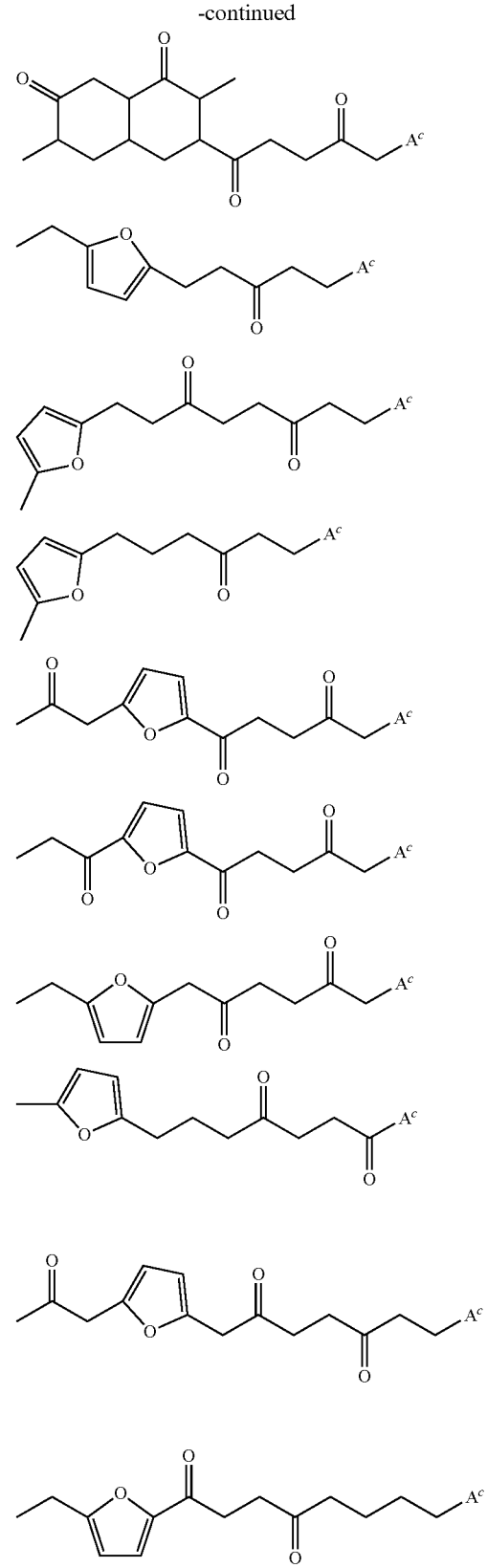
The surfactant (c) is a novel compound, and may be produced by any of the following production methods, for example.

The surfactant (c) may be suitably produced by a production method including:
a step (11c) of reacting a compound (10c) represented by the formula:

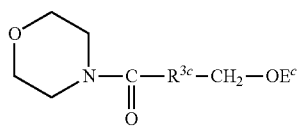

(wherein $R^{3c}$ is defined as described above; and $E^c$ is a leaving group), lithium, and a chlorosilane compound represented by the formula: $R^{201c}{}_3Si$—Cl (wherein each $R^{201c}$ is independently an alkyl group or an aryl group) to provide a compound (11c) represented by the formula:

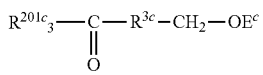

(wherein $R^{3c}$, $R^{201c}$, and $E^c$ are defined as described above);
a step (12c) of reacting the compound (11c) and an olefin represented by the formula:

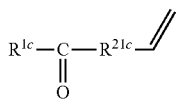

(wherein $R^{1c}$ is defined as described above; and $R^{21c}$ is a single bond or a divalent linking group) to provide a compound (12a) represented by the formula:

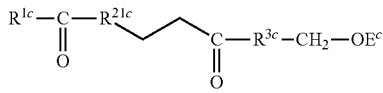

(wherein $R^{1c}$, $R^{21c}$, $R^{3c}$, and $E^c$ are defined as described above);
a step (13c) of eliminating the leaving group in the compound (12c) to provide a compound (13c) represented by the formula:

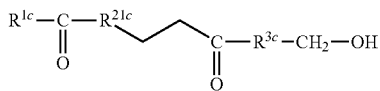

(wherein $R^{1c}$, $R^{21c}$, and $R^{3c}$ are defined as described above); and
a step (14c) of oxidizing the compound (13c) to provide a compound (14a) represented by the formula:

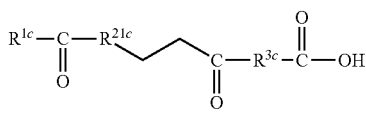

(wherein $R^{1c}$, $R^{21c}$, and $R^{3c}$ are defined as described above).

When $R^{1c}$ contains a furan ring, the furan ring may be cleaved by an acid and converted into a dicarbonyl derivative, for example. Examples of the acid include acetic acid, hydrochloric acid, and p-toluene sulfone, of which acetic acid is preferred.

In the step (11c), it is preferable that lithium and the chlorosilane compound are reacted in advance to obtain a syroxylithium compound, and then the syroxylithium compound and the compound (10c) are reacted to obtain the compound (11c).

$E^c$ represents a leaving group. Examples of the leaving group include a tert-butyldimethylsilyl (TBS) group, a triethylsilyl (TES) group, a triisopropylsilyl (TIPS) group, a tert-butyldiphenylsilyl (TBDPS) group, and a benzyl (Bn) group.

$R^{21c}$ is preferably a single bond or a linear or branched alkylene group having 1 or more carbon atoms.

Examples of the chlorosilane compound include:

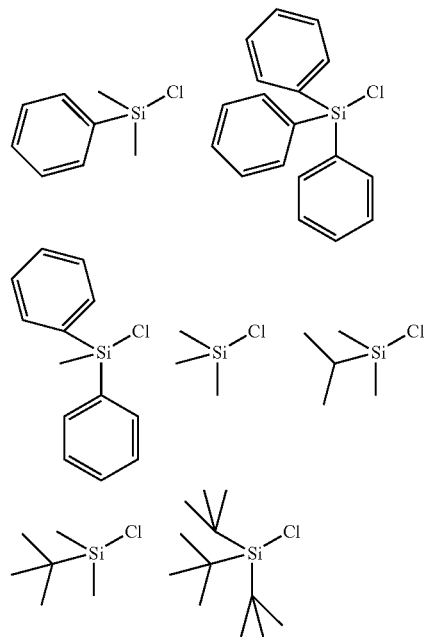

Any of the reactions in the step (11c) may be performed in a solvent. The solvent is preferably an organic solvent, more preferably an aprotic polar solvent, and still more preferably an ether. Examples of the ether include ethyl methyl ether, diethyl ether, monoglyme (ethylene glycol dimethyl ether), diglyme (diethylene glycol dimethyl ether), triglyme (triethylene glycol dimethyl ether), tetrahydrofuran, tetraglyme (tetraethylene glycol dimethyl ether), and crown ether (15-crown-5, 18-crown-6), of which tetrahydrofuran and diethyl ether is preferred.

The reaction temperature of lithium and the chlorosilane compound in the step (11c) is preferably −78 to 100° C., more preferably 10 to 40° C.

The reaction temperature of the siloxylithium compound and the compound (10c) in the step (11c) is preferably −100 to 0° C., more preferably −80 to −50° C.

The reaction pressure of lithium and the chlorosilane compound in the step (11c) is preferably 0.1 to 5 MPa, and more preferably 0.1 to 1 MPa.

The reaction pressure of the siloxylithium compound and the compound (10c) in the step (11c) is preferably 0.1 to 5 MPa, and more preferably 0.1 to 1 MPa.

The reaction time of lithium and the chlorosilane compound in the step (11c) is preferably 0.1 to 72 hours, and more preferably 6 to 10 hours.

The reaction time of the siloxylithium compound and the compound (10c) in the step (11c) is preferably 0.1 to 72 hours, and more preferably 1 to 2 hours.

Regarding the reaction ratio between the compound (11c) and the olefin in the step (12c), the amount of the olefin is preferably 1 to 2 mol, and more preferably 1 to 1.1 mol, based on 1 mol of the compound (11c) in consideration of the improvement of the yield and the reduction of the waste.

The reaction in the step (12c) may be performed in a solvent in the presence of a thiazolium salt and a base.

Examples of the thiazolium salt include 3-ethyl-5-(2-hydroxyethyl)-4-methylthiazolium bromide and 3-benzyl-5-(2-hydroxyethyl)-4-methylthiazolium chloride.

Examples of the base include 1,8-diazabicyclo[5.4.0]-7-undecene and triethylamine.

The solvent is preferably an organic solvent, more preferably an aprotic polar solvent, and still more preferably an alcohol or ether.

Examples of the alcohol include methanol, ethanol, 1-propanol, and isopropanol.

Examples of the ether include ethyl methyl ether, diethyl ether, monoglyme (ethylene glycol dimethyl ether), diglyme (diethylene glycol dimethyl ether), triglyme (triethylene glycol dimethyl ether), tetrahydrofuran, tetraglyme (tetraethylene glycol dimethyl ether), and crown ether (15-crown-5, 18-crown-6), of which tetrahydrofuran and diethyl ether is preferred.

The reaction temperature in the step (12c) is preferably 40 to 60° C., and more preferably 50 to 55° C.

The reaction pressure in the step (12c) is preferably 0.1 to 5 MPa, and more preferably 0.1 to 1 MPa.

The reaction duration in the step (12c) is preferably 0.1 to 72 hours, and more preferably 6 to 10 hours.

The elimination reaction for the leaving group in the step (13c) may be performed using a fluoride ion or an acid. Examples of methods of eliminating the leaving group include a method using hydrofluoric acid; a method using an amine complex of hydrogen fluoride such as pyridine-nHF or triethylamine-nHF; a method using an inorganic salt such as cesium fluoride, potassium fluoride, lithium tetrafluoroborate ($LiBF_4$), or ammonium fluoride; and a method using an organic salt such as tetrabutylammonium fluoride (TBAF).

The elimination reaction for the leaving group in the step (13c) may be performed in a polar solvent. The solvent is preferably an organic solvent, more preferably an aprotic polar solvent, and still more preferably an ether.

Examples of the ether include ethyl methyl ether, diethyl ether, monoglyme (ethylene glycol dimethyl ether), diglyme (diethylene glycol dimethyl ether), triglyme (triethylene glycol dimethyl ether), tetrahydrofuran, tetraglyme (tetraethylene glycol dimethyl ether), and crown ether (15-crown-5, 18-crown-6), of which tetrahydrofuran and diethyl ether is preferred.

The reaction temperature in the step (13c) is preferably 0 to 40° C., and more preferably 0 to 20° C.

The reaction pressure in the step (13c) is preferably 0.1 to 5 MPa, and more preferably 0.1 to 1 MPa.

The reaction duration in the step (13c) is preferably 0.1 to 72 hours, and more preferably 3 to 8 hours.

The oxidation in the step (14c) may be performed in a solvent in the presence of sodium chlorite.

The solvent may be an alcohol, such as methanol, ethanol, 1-propanol, isopropanol, 1-butanol, or tert-butyl alcohol, or water. A disodium hydrogen phosphate solution may be used as the buffer.

The compound (14c) may be brought into contact with an alkali to convert —COOH into a salt form. Examples of the alkali include sodium hydroxide, potassium hydroxide, lithium hydroxide, and ammonia; for example, an aqueous solution of ammonia is preferably used.

After the completion of each step, the solvent may be distilled off, or distillation, purification or the like may be performed to increase the purity of each resulting compound.

The surfactant (c) may also be suitably produced by a production method including:

a step (21c) of reacting a ketone represented by the formula:

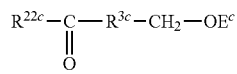

(wherein $R^{3c}$ is defined as described above; $R^{22c}$ is a monovalent organic group; and $E^c$ is a leaving group) and a carboxylate represented by the formula:

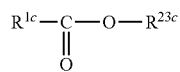

(wherein $R^{1c}$ is defined as described above; and $R^{23c}$ is a monovalent organic group) to provide a compound (21c) represented by the formula:

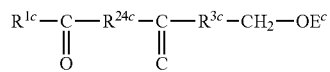

(wherein $R^{1c}$, $R^{3c}$, and $E^c$ are defined as described above; and $R^{24c}$ is a single bond or a divalent linking group);

a step (22c) of eliminating the leaving group in the compound (21c) to provide a compound (22c) represented by the formula:

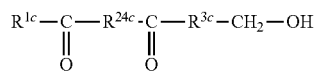

(wherein $R^{1c}$, $R^{24c}$, and $R^{3c}$ are defined as described above); and a step (23c) of oxidizing the compound (22c) to provide a compound (23c) represented by the formula:

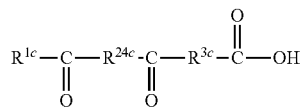

wherein $R^{1c}$, $R^{24c}$, and $R^{3c}$ are defined as described above.

When $R^{1c}$ contains a furan ring, the furan ring may be cleaved by an acid and converted into a dicarbonyl derivative, for example. Examples of the acid include acetic acid, hydrochloric acid, and p-toluene sulfone, of which acetic acid is preferred.

$E^c$ represents a leaving group. Examples of the leaving group include a tert-butyldimethylsilyl (TBS) group, a triethylsilyl (TES) group, a triisopropylsilyl (TIPS) group, a tert-butyldiphenylsilyl (TBDPS) group, and a benzyl (Bn) group.

$R^{22c}$ is preferably a linear or branched alkyl group having 1 or more carbon atoms, and more preferably a methyl group.

$R^{23c}$ is preferably a linear or branched alkyl group having 1 or more carbon atoms, and more preferably a methyl group.

$R^{24c}$ is preferably a linear or branched alkylene group having 1 or more carbon atoms, and more preferably a methylene group ($-CH_2-$).

The reaction in the step (21c) may be performed in a solvent in the presence of a base.

Examples of the base include sodium amide, sodium hydride, sodium methoxide, and sodium ethoxide.

The solvent is preferably an organic solvent, more preferably an aprotic polar solvent, and still more preferably an alcohol or an ether.

Examples of the alcohol include methanol, ethanol, 1-propanol, and isopropanol.

Examples of the ether include ethyl methyl ether, diethyl ether, monoglyme (ethylene glycol dimethyl ether) diglyme (diethylene glycol dimethyl ether), triglyme (triethylene glycol dimethyl ether), tetrahydrofuran, tetraglyme (tetraethylene glycol dimethyl ether), and crown ether (15-crown-5, 18-crown-6), of which tetrahydrofuran and diethyl ether is preferred.

The reaction temperature in the step (21c) is preferably 0 to 40° C., and more preferably 0 to 20.

The reaction pressure in the step (21c) is preferably 0.1 to 5 MPa, and more preferably 0.1 to 1 MPa.

The reaction duration in the step (21c) is preferably 0.1 to 72 hours, and more preferably 3 to 8 hours.

The elimination reaction for the leaving group in the step (22c) may be performed using a fluoride ion or an acid. Examples of methods of eliminating the leaving group include a method using hydrofluoric acid; a method using an amine complex of hydrogen fluoride such as pyridine-nHF or triethylamine-nHF; a method using an inorganic salt such as cesium fluoride, potassium fluoride, lithium tetrafluoroborate ($LiBF_4$), or ammonium fluoride; and a method using an organic salt such as tetrabutylammonium fluoride (TBAF).

The elimination reaction for the leaving group in the step (22c) may be performed in a solvent. The solvent is preferably an organic solvent, more preferably an aprotic polar solvent, and still more preferably an ether.

Examples of the ether include ethyl methyl ether, diethyl ether, monoglyme (ethylene glycol dimethyl ether), diglyme (diethylene glycol dimethyl ether), triglyme (triethylene glycol dimethyl ether), tetrahydrofuran, tetraglyme (tetraethylene glycol dimethyl ether), and crown ether (15-crown-5, 18-crown-6), of which tetrahydrofuran and diethyl ether is preferred.

The reaction temperature in the step (22c) is preferably 0 to 40° C., and more preferably 0 to 20° C.

The reaction pressure in the step (22c) is preferably 0 to 5 MPa, and more preferably 0.1 to 1 MPa.

The reaction duration in the step (22c) is preferably 0.1 to 72 hours, and more preferably 3 to 8 hours.

The oxidation in the step (23c) may be performed in a solvent in the presence of sodium chlorite.

The solvent may be an alcohol or water. A disodium hydrogen phosphate solution may be used as the buffer.

The compound (23c) may be brought into contact with an alkali to convert $-COOH$ into a salt form. Examples of the alkali include sodium hydroxide, potassium hydroxide, lithium hydroxide, and ammonia; for example, an aqueous solution of ammonia is preferably used.

After the completion of each step, the solvent may be distilled off, or distillation, purification or the like may be performed to increase the purity of each resulting compound.

The surfactant (c) may also be suitably produced by a production method including:

a step (31c) of reacting an alkyl halide represented by the formula: $Y^c-R^{3c}-CH_2-OE^c$ (wherein $R^{3c}$ is defined as described above; $Y^c$ is a halogen atom; and $E^c$ is a leaving group) and lithium acetylide represented by the formula:

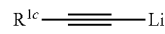

(wherein $R^{1c}$ is defined as described above) to provide a compound (31c) represented by the formula:

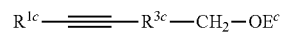

(wherein $R^{1c}$, $R^{3c}$, and $E^c$ are defined as described above);

a step (32c) of oxidizing the compound (31c) to provide a compound (32c) represented by the formula:

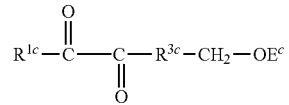

(wherein $R^{1c}$, $R^{3c}$, and $E^c$ are defined as described above);

a step (33c) of eliminating the leaving group in the compound (32c) to provide a compound (33c) represented by the formula:

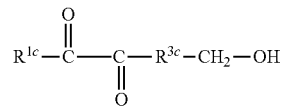

(wherein $R^{1c}$ and $R^{3c}$ are defined as described above); and a step (34c) of oxidizing the compound (33c) to provide a compound (34c) represented by the formula:

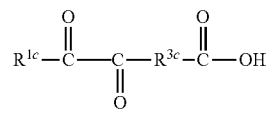

(wherein $R^{1c}$ and $R^{3c}$ are defined as described above).

When $R^{1c}$ contains a furan ring, the furan ring may be cleaved by an acid and converted into a dicarbonyl derivative, for example. Examples of the acid include acetic acid, hydrochloric acid, and p-toluene sulfone, of which acetic acid is preferred.

$E^c$ represents a leaving group. Examples of the leaving group include a tert-butyldimethylsilyl (TBS) group, a triethylsilyl (TES) group, a triisopropylsilyl (TIPS) group, a tert-butyldiphenylsilyl (TBDPS) group, and a benzyl (Bn) group.

Regarding the reaction ratio between the alkyl halide and the lithium acetylide in the step (31c), the lithium acetylide is preferably used in an amount of 1 to 2 mol, and more preferably 1 to 1.2 mol, based on 1 mol of the alkyl halide in consideration of the improvement of the yield and the reduction of the waste.

The reaction in the step (31c) may be performed in a solvent. Hexane is preferable as the solvent.

The reaction temperature in the step (31c) is preferably −100 to −40° C., and more preferably −80 to −50° C.

The reaction pressure in the step (31c) is preferably 0.1 to 5 MPa, and more preferably 0.1 to 1 MPa.

The reaction duration in the step (31c) is preferably 0.1 to 72 hours, and more preferably 6 to 10 hours.

The oxidation in the step (32c) may be performed in a nitrile solvent using a complex generated by treating [(Cn*)Ru$^{III}$(CF$_3$CO$_2$)$_3$]·H$_2$O (wherein Cn* is 1,4,7-trimethyl-1,4,7-triazabicyclononane) with (NH$_4$)$_2$Ce(NO$_3$)$_6$ and trifluoroacetic acid and then adding sodium perchlorate thereto.

After the completion of the oxidation, the product may be neutralized with an alkali, and then an organic solvent such as an ether may be used to extract the compound (32c).

The reaction temperature in the step (32c) is preferably −30 to 100° C., and more preferably 40 to 90° C.

The reaction pressure in the step (32c) is preferably 0.1 to 5 MPa, and more preferably 0.1 to 1 MPa.

The reaction duration in the step (32c) is preferably 0.1 to 72 hours, and more preferably 3 to 8 hours.

The elimination reaction for the leaving group in the step (33c) may be performed using a fluoride ion or an acid. Examples of methods of eliminating the leaving group include a method using hydrofluoric acid; a method using an amine complex of hydrogen fluoride such as pyridine-nHF or triethylamine-nHF; a method using an inorganic salt such as cesium fluoride, potassium fluoride, lithium tetrafluoroborate (LiBF$_4$), or ammonium fluoride; and a method using an organic salt such as tetrabutylammonium fluoride (TBAF).

The elimination reaction for the leaving group in the step (33c) may be performed in a solvent. The solvent is preferably an organic solvent, more preferably an aprotic polar solvent, and still more preferably an ether.

Examples of the ether include ethyl methyl ether, diethyl ether, monoglyme (ethylene glycol dimethyl ether), diglyme (diethylene glycol dimethyl ether), triglyme (triethylene glycol dimethyl ether), tetrahydrofuran, tetraglyme (tetraethylene glycol dimethyl ether), and crown ether (15-crown-5, 18-crown-6), of which tetrahydrofuran and diethyl ether is preferred.

The reaction temperature in the step (33c) is preferably 0 to 40° C., and more preferably 0 to 20° C.

The reaction pressure in the step (33c) is preferably 0.1 to 5 MPa, and more preferably 0.1 to 1 MPa.

The reaction duration in the step (33c) is preferably 0.1 to 72 hours, and more preferably 3 to 8 hours.

The oxidation in the step (34c) may be performed in a solvent in the presence of sodium chlorite.

The solvent may be an alcohol or water. A disodium hydrogen phosphate solution may be used as the buffer.

The compound (34c) may be brought into contact with an alkali to convert —COOH into a salt form. Examples of the alkali include sodium hydroxide, potassium hydroxide, lithium hydroxide, and ammonia; for example, an aqueous solution of ammonia is preferably used.

After the completion of each step, the solvent may be distilled off, or distillation, purification or the like may be performed to increase the purity of each resulting compound.

The surfactant (c) may also be suitably produced by a production method including:
a step (51c) of reacting divinyl ketone represented by the formula:

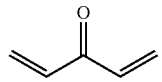

and 2-methylfuran represented by the formula:

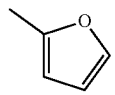

to provide a compound (51c) represented by the formula:

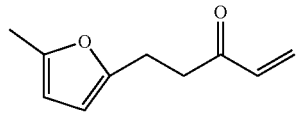

a step (52c) of reacting the compound (51c) and furan represented by the formula:

to provide a compound (52c) represented by the formula:

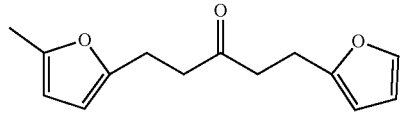 [SMILES: Cc1ccc(CCC(=O)CCc2ccco2)o1]

a step (53c) of heating the compound (52c) in the presence of an acid to provide a compound (53c) represented by the formula:

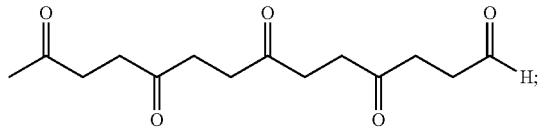

and
a step (54c) of oxidizing the compound (53c) to provide a compound (54c) represented by the formula:

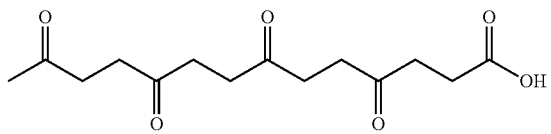 [SMILES: CC(=O)CCC(=O)CCC(=O)CCC(=O)CCC(=O)O]

Regarding the reaction ratio between divinyl ketone and 2-methyl furan in the step (51c), 2-methyl furan is preferably used in an amount of 0.5 to 1 mol, and more preferably 0.6 to 0.9 mol, based on 1 mol of divinyl ketone in consideration of the improvement of the yield and the reduction of the waste.

The reaction in the step (51c) is preferably performed in the presence of an acid. Examples of the acid include acetic acid, hydrochloric acid, and p-toluene sulfone, of which acetic acid is preferred.

The amount of the acid used in the step (51c) is preferably 0.1 to 2 mol, and more preferably 0.1 to 1 mol, based on 1 mol of the divinyl ketone in consideration of the improvement of the yield and the reduction of the waste.

The reaction in the step (51c) may be performed in a polar solvent. The solvent is preferably water or acetonitrile.

The reaction temperature in the step (51c) is preferably 20 to 100° C., and more preferably 40 to 100° C.

The reaction pressure in the step (51c) is preferably 0.1 to 5 MPa, and more preferably 0.1 to 1 MPa.

The reaction duration in the step (51c) is preferably 0.1 to 72 hours, and more preferably 4 to 8 hours.

Regarding the reaction ratio between the compound (51c) and the furan in the step (52c), the amount of the furan is preferably 1 to 2 mol, and more preferably 1 to 1.1 mol, based on 1 mol of the compound (51c) in consideration of the improvement of the yield and the reduction of the waste.

The reaction in the step (52c) is preferably performed in the presence of an acid. Examples of the acid include acetic acid, hydrochloric acid, and p-toluene sulfone, of which acetic acid is preferred.

The amount of the acid used in the step (52c) is preferably 0.1 to 2 mol, and more preferably 0.1 to 1 mol, based on 1 mol of the compound (51c) in consideration of the improvement of the yield and the reduction of the waste.

The reaction in the step (52c) may be performed in a polar solvent. Water is preferable as the solvent.

The reaction temperature in the step (52c) is preferably 20 to 100° C., and more preferably 40 to 100° C.

The reaction pressure in the step (52c) is preferably 0.1 to 5 MPa, and more preferably 0.1 to 1 MPa.

The reaction duration in the step (52c) is preferably 0.1 to 72 hours, and more preferably 4 to 8 hours.

In the step (53c), the furan ring is cleaved by heating the compound (52c) in the presence of an acid.

The acid is preferably hydrochloric acid or sulfuric acid.

The reaction in the step (53c) may be performed in a polar solvent. Water is preferable as the solvent.

The reaction temperature in the step (53c) is preferably 50 to 100° C., and more preferably 70 to 100° C.

The reaction pressure in the step (53c) is preferably 0.1 to 5 MPa, and more preferably 0.1 to 1 MPa.

The reaction duration in the step (53c) is preferably 0.1 to 72 hours, and more preferably 1 to 12 hours.

The oxidation in the step (54c) may be performed in a solvent in the presence of sodium chlorite.

The solvent may be tert-butyl alcohol or water. A disodium hydrogen phosphate solution may be used as the buffer.

The compound (54c) may be brought into contact with an alkali to convert —COOH into a salt form. Examples of the alkali include sodium hydroxide, potassium hydroxide, lithium hydroxide, and ammonia; for example, an aqueous solution of ammonia is preferably used.

After the completion of each step, the solvent may be distilled off, or distillation, purification or the like may be performed to increase the purity of each resulting compound.

The surfactant (c) may also be suitably produced by a production method including:
a step (61c) of reacting an alkene represented by the formula:

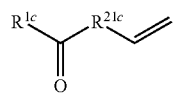

(wherein $R^{1c}$ is defined as described above; and $R^{21c}$ is a single bond or a divalent linking group) and an alkyne represented by the formula:

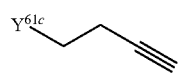

(wherein $Y^{61c}$ is an alkyl ester group) to provide a compound (61c) represented by the formula:

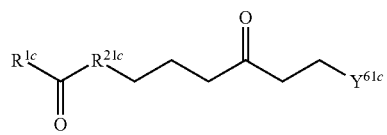

(wherein $R^{1c}$, $R^{21c}$, and $Y^{61c}$ are defined as described above); and
a step (62c) of causing an alkali to act on the compound (61c) and then causing an acid to act thereon to provide a compound (62c) represented by the formula:

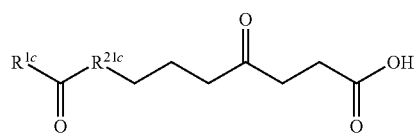

(wherein $R^{1c}$ and $R^{21c}$ are defined as described above).

When $R^{1c}$ contains a furan ring, the furan ring may be cleaved by an acid and converted into a dicarbonyl derivative, for example. Examples of the acid include acetic acid, hydrochloric acid, and p-toluene sulfone, of which acetic acid is preferred.

$R^{21c}$ is preferably a single bond or a linear or branched alkylene group having 1 or more carbon atoms.

Regarding the reaction ratio between the alkene and the alkyne in the step (61c), the alkene is preferably used in an amount of 0.5 to 2 mol, and more preferably 0.6 to 1.2 mol, based on 1 mol of the alkyne in consideration of the improvement of the yield and the reduction of the waste.

The reaction in the step (61c) is preferably performed in the presence of a metal catalyst. An example of the metal is ruthenium.

The amount of the metal catalyst used in the step (61c) is preferably 0.01 to 0.4 mol, and more preferably 0.05 to 0.1 mol, based on 1 mol of the alkene in consideration of the improvement of the yield and the reduction of the waste.

The reaction in the step (61c) may be performed in a polar solvent. The solvent is preferably water, acetonitrile, dimethylacetamide, or dimethylformamide.

The reaction temperature in the step (61c) is preferably 20 to 160° C., and more preferably 40 to 140° C.

The reaction pressure in the step (61c) is preferably 0.1 to 5 MPa, and more preferably 0.1 to 1 MPa.

The reaction duration in the step (61c) is preferably 0.1 to 72 hours, and more preferably 4 to 8 hours.

Regarding the reaction ratio between the compound (61c) and the alkali in the step (62c), the amount of the alkali is preferably 0.6 to 2 mol, and more preferably 0.8 to 1.1 mol, based on 1 mol of the compound (61c) in consideration of the improvement of the yield and the reduction of the waste.

The amount of the acid used in the step (62c) is preferably 1.0 to 20.0 mol, and more preferably 1.0 to 10.0 mol, based on 1 mol of the compound (61c) in consideration of the improvement of the yield and the reduction of the waste.

The reaction in the step (62c) may be performed in a polar solvent. Water is preferable as the solvent.

The reaction temperature in the step (62c) is preferably 0 to 100° C., and more preferably 20 to 100° C.

The reaction pressure in the step (62c) is preferably 0.1 to 5 MPa, and more preferably 0.1 to 1 MPa.

The reaction duration in the step (62c) is preferably 0.1 to 72 hours, and more preferably 4 to 8 hours.

The compound (62c) may be brought into contact with an alkali to convert —COOH into a salt form. Examples of the alkali include sodium hydroxide, potassium hydroxide, lithium hydroxide, and ammonia; for example, an aqueous solution of ammonia is preferably used.

After the completion of each step, the solvent may be distilled off, or distillation, purification or the like may be performed to increase the purity of each resulting compound.

The surfactant (d) will be described.

In the formula (d), $R^{1d}$ is a linear or branched alkyl group having 1 or more carbon atoms and optionally having a substituent or a cyclic alkyl group having 3 or more carbon atoms and optionally having a substituent.

When having 3 or more carbon atoms, the alkyl group optionally contains a monovalent or divalent heterocycle, or optionally forms a ring. The heterocycle is preferably an unsaturated heterocycle, more preferably an oxygen-containing unsaturated heterocycle, and examples thereof include a furan ring. In $R^{1d}$, a divalent heterocycle may be present between two carbon atoms, or a divalent heterocycle may be present at an end and bind to —C(=O)—, or a monovalent heterocycle may be present at an end of the alkyl group.

The "number of carbon atoms" in the alkyl group as used herein includes the number of carbon atoms constituting the heterocycles.

The substituent which may be contained in the alkyl group for $R^{1d}$ is preferably a halogen atom, a linear or branched alkyl group having 1 to 10 carbon atoms, or a cyclic alkyl group having 3 to 10 carbon atoms, or a hydroxy group, and particularly preferably a methyl group or an ethyl group.

The alkyl group for $R^{1d}$ is preferably free from a carbonyl group.

In the alkyl group, 75% or less of the hydrogen atoms bonded to the carbon atoms may be replaced by halogen atoms, 50% or less thereof may be replaced by halogen atoms, or 25% or less thereof may be replaced by halogen atoms. The alkyl group is preferably a non-halogenated alkyl group free from halogen atoms such as fluorine atoms and chlorine atoms.

The alkyl group preferably contains no substituent.

$R^{1d}$ is preferably a linear or branched alkyl group having 1 to 10 carbon atoms and optionally having a substituent or a cyclic alkyl group having 3 to 10 carbon atoms and optionally having a substituent, more preferably a linear or branched alkyl group having 1 to 10 carbon atoms and free from a carbonyl group or a cyclic alkyl group having 3 to 10 carbon atoms and free from a carbonyl group, still more preferably a linear or branched alkyl group having 1 to 10 carbon atoms and not having a substituent, further preferably a linear or branched alkyl group having 1 to 3 carbon atoms and not having a substituent, particularly preferably a methyl group (—$CH_3$) or an ethyl group (—$C_2H_5$), and most preferably a methyl group (—$CH_3$).

In the formula (d), $R^{2d}$ and $R^{4d}$ are each independently H or a substituent. A plurality of $R^{2d}$ and $R^{4d}$ may be the same or different.

The substituent for each of $R^{2d}$ and $R^{4d}$ is preferably a halogen atom, a linear or branched alkyl group having 1 to 10 carbon atoms, a cyclic alkyl group having 3 to 10 carbon atoms, or a hydroxy group, and particularly preferably a methyl group or an ethyl group.

The alkyl group for each of $R^{2d}$ and $R^{4d}$ is preferably free from a carbonyl group.

In the alkyl group, 75% or less of the hydrogen atoms bonded to the carbon atoms may be replaced by halogen atoms, 50% or less thereof may be replaced by halogen atoms, or 25% or less thereof may be replaced by halogen atoms. The alkyl group is preferably a non-halogenated alkyl group free from halogen atoms such as fluorine atoms and chlorine atoms.

The alkyl group preferably contains no substituent.

The alkyl group for each of $R^{2d}$ and $R^{4d}$ is preferably a linear or branched alkyl group having 1 to 10 carbon atoms and free from a carbonyl group or a cyclic alkyl group having 3 to 10 carbon atoms and free from a carbonyl group, more preferably a linear or branched alkyl group having 1 to 10 carbon atoms and free from a carbonyl group, still more preferably a linear or branched alkyl group having 1 to 3 carbon atoms and not having a substituent, and particularly preferably a methyl group (—$CH_3$) or an ethyl group (—$C_2H_5$).

$R^{2d}$ and $R^{4d}$ are preferably each independently H or a linear or branched alkyl group having 1 to 10 carbon atoms and free from a carbonyl group, more preferably H or a linear or branched alkyl group having 1 to 3 carbon atoms and not having a substituent, still more preferably H, a methyl group (—$CH_3$), or an ethyl group (—$C_2H_5$), and particularly preferably H.

In the formula (d), $R^{3d}$ is an alkylene group having 1 to 10 carbon atoms and optionally having a substituent. When a plurality of $R^{3d}$ are present, they may be the same or different.

The alkylene group is preferably free from a carbonyl group.

In the alkylene group, 75% or less of the hydrogen atoms bonded to the carbon atoms may be replaced by halogen atoms, 50% or less thereof may be replaced by halogen atoms, or 25% or less thereof may be replaced by halogen atoms. The alkylene group is preferably a non-halogenated alkyl group free from halogen atoms such as fluorine atoms and chlorine atoms.

The alkylene group preferably does not have any substituent.

The alkylene group is preferably a linear or branched alkylene group having 1 to 10 carbon atoms and optionally having a substituent or a cyclic alkylene group having 3 to 10 carbon atoms and optionally having a substituent, preferably a linear or branched alkylene group having 1 to 10 carbon atoms and free from a carbonyl group or a cyclic alkylene group having 3 to 10 carbon atoms and free from a carbonyl group, more preferably a linear or branched alkylene group having 1 to 10 carbon atoms and not having a substituent, and still more preferably a methylene group (—CH$_2$—), an ethylene group (—C$_2$H$_4$—), an isopropylene group (—CH(CH$_3$) CH$_2$—), or a propylene group (—C$_3$H$_6$—).

Any two of R$^{1b}$, R$^{2b}$, R$^{3b}$, and R$^{4b}$ optionally bind to each other to form a ring.

In the formula (d), n is an integer of 1 or more. In the formula, n is preferably an integer of 1 to 40, more preferably an integer of 1 to 30, and still more preferably an integer of 5 to 25.

In the formula (d), p and q are each independently an integer of 0 or more. p is preferably an integer of 0 to 10, more preferably 0 or 1. q is preferably an integer of 0 to 10, more preferably an integer of 0 to 5.

The sum of n, p, and q is preferably an integer of 6 or more. The sum of n, p, and q is more preferably an integer of 8 or more. The sum of n, p, and q is also preferably an integer of 60 or less, more preferably an integer of 50 or less, and still more preferably an integer of 40 or less.

In the formula (d), A$^d$ is —SO$_3$X$^d$ or —COOX$^d$, wherein X$^d$ is H, a metal atom, NR$^{5d}_4$, imidazolium optionally having a substituent, pyridinium optionally having a substituent, or phosphonium optionally having a substituent, wherein R$^{5d}$ is H or an organic group and may be the same or different. R$^{5d}$ is preferably H or an organic group having 1 to 10 carbon atoms, and more preferably H or an organic group having 1 to 4 carbon atoms. Examples of the metal atom include monovalent and divalent metal atoms, and examples thereof include alkali metals (Group 1) and alkaline earth metals (Group 2), and preferred is Na, K or Li. X$^d$ may be a metal atom or NR$^{5d}_4$, wherein R$^{5d}$ is defined as described above. X$^d$ may be a metal atom or NR$^{5d}_4$, wherein R$^{5d}$ is defined as described above.

X$^d$ is preferably H, an alkali metal (Group 1), an alkaline earth metal (Group 2), or NR$^{5d}_4$, more preferably H, Na, K, Li, or NH$_4$ because they are easily dissolved in water, still more preferably Na, K, or NH$_4$ because they are more easily dissolved in water, particularly preferably Na or NH$_4$, and most preferably NH$_4$ because it can be easily removed. When X$^d$ is NH$_4$, the solubility of the surfactant in an aqueous medium is excellent, and the metal component is unlikely to remain in the PTFE or the final product.

In the formula (d), L is a single bond, —CO$_2$—B—*, —OCO—B—*, —CONR$^{6d}$—B—*, —NR$^{6d}$CO—B—*, or —CO— other than the carbonyl groups in —CO$_2$—B—, —OCO—B—, —CONR$^{6d}$—B—, and —NR$^{6d}$CO—B—, wherein B is a single bond or an alkylene group having 1 to 10 carbon atoms and optionally having a substituent, R$^{6d}$ is H or an alkyl group having 1 to 4 carbon atoms and optionally having a substituent. The alkylene group more preferably has 1 to 5 carbon atoms. R$^{6d}$ is more preferably H or a methyl group. * indicates the side bonded to A$^d$ in the formula.

L is preferably a single bond.

The surfactant preferably has a $^1$H-NMR spectrum in which all peak intensities observed in a chemical shift range of 2.0 to 5.0 ppm give an integral value of 10 or higher.

The surfactant preferably has a $^1$H-NMR spectrum in which all peak intensities observed in a chemical shift range of 2.0 to 5.0 ppm give an integral value within the above range. In this case, the surfactant preferably has a ketone structure in the molecule.

The integral value of the surfactant is more preferably 15 or more, and preferably 95 or less, more preferably 80 or less, and still more preferably 70 or less.

The integral value is determined using a heavy water solvent at room temperature. The heavy water content is adjusted to 4.79 ppm.

Examples of the surfactant (d) include:
CH$_3$C(O)CH$_2$CH$_2$CH$_2$CH$_2$CH$_2$CH$_2$CH$_2$CH$_2$COOK,
CH$_3$C(O)CH$_2$CH$_2$CH$_2$CH$_2$CH$_2$CH$_2$CH$_2$COONa,
CH$_3$C(O)CH$_2$CH$_2$CH$_2$CH$_2$CH$_2$CH$_2$COONa,
CH$_3$C(O)CH$_2$CH$_2$CH$_2$CH$_2$CH$_2$COONa,
CH$_3$C(O)CH$_2$CH$_2$CH$_2$CH$_2$COONa,
CH$_3$C(O)CH$_2$CH$_2$CH$_2$COONa,
CH$_3$C(O) CH$_2$CH$_2$CH$_2$CH$_2$CH$_2$CH$_2$CH$_2$CH$_2$CH$_2$CH$_2$CH$_2$CH$_2$COONa,
CH$_3$C(O) CH$_2$CH$_2$CH$_2$CH$_2$CH$_2$CH$_2$CH$_2$CH$_2$CH$_2$CH$_2$CH$_2$CH$_2$CH$_2$CH$_2$CH$_2$CH$_2$CH$_2$COONa,
(CH$_3$)$_3$CC(O) CH$_2$CH$_2$CH$_2$CH$_2$CH$_2$CH$_2$CH$_2$CH$_2$COONa,
(CH$_3$)$_2$CHC(O) CH$_2$CH$_2$CH$_2$CH$_2$CH$_2$CH$_2$CH$_2$CH$_2$COONa,
(CH$_2$)$_5$CHC(O) CH$_2$CH$_2$CH$_2$CH$_2$CH$_2$CH$_2$CH$_2$CH$_2$COONa,
CH$_3$CH$_2$C(O)CH$_2$CH$_2$CH$_2$CH$_2$CH$_2$CH$_2$CH$_2$COONa,
CH$_3$CH$_2$CH$_2$C(O)CH$_2$CH$_2$CH$_2$CH$_2$CH$_2$CH$_2$COONa,
CH$_3$CH$_2$CH$_2$CH$_2$C(O)CH$_2$CH$_2$CH$_2$CH$_2$CH$_2$COONa,
CH$_3$CH$_2$CH$_2$CH$_2$CH$_2$C(O)CH$_2$CH$_2$CH$_2$CH$_2$COONa,
CH$_3$CH$_2$CH$_2$CH$_2$CH$_2$CH$_2$C(O)CH$_2$CH$_2$CH$_2$COONa,
CH$_3$CH$_2$CH$_2$CH$_2$CH$_2$CH$_2$CH$_2$C(O)CH$_2$CH$_2$COONa,
CH$_3$CH$_2$CH$_2$CH$_2$CH$_2$CH$_2$CH$_2$CH$_2$C(O)CH$_2$COONa,
CH$_3$C(O)CH$_2$CH$_2$CH$_2$CH$_2$CH$_2$CH$_2$CH$_2$CH$_2$OCH$_2$CH$_2$COONa,
CH$_3$C(O)CH$_2$CH$_2$CH$_2$CH$_2$CH$_2$CH$_2$CH$_2$CH$_2$C(O) NHCH$_2$COOK,
CH$_3$C(O)CH$_2$CH$_2$CH$_2$CH$_2$CH$_2$CH$_2$CH$_2$CH$_2$NHC(O) CH$_2$COOK,
CH$_3$C(O)CH$_2$CH$_2$CH$_2$CH$_2$CH$_2$CH$_2$CH$_2$CH$_2$C(O) OCH$_2$COONa,
CH$_3$C(O)CH$_2$CH$_2$CH$_2$CH$_2$CH$_2$CH$_2$CH$_2$CH$_2$OC(O) CH$_2$COONa,
CH$_3$C(O)CH$_2$CH$_2$CH$_2$CH$_2$CH$_2$CH$_2$CH$_2$CH$_2$C(O) COONa,
CH$_3$C(O)CH$_2$CH$_2$CH$_2$CH$_2$CH$_2$CH$_2$CH$_2$CH$_2$C(O) COOH,
CH$_3$C(O)CH$_2$CH$_2$CH$_2$CH$_2$CH$_2$CH$_2$CH$_2$CH$_2$C(O) COOLi,
CH$_3$C(O)CH$_2$CH$_2$CH$_2$CH$_2$CH$_2$CH$_2$CH$_2$CH$_2$C(O) COONH$_4$,
CH$_3$C(O)CH$_2$CH$_2$CH$_2$CH$_2$CH$_2$CH$_2$CH$_2$CH$_2$C(O) COONa, CH$_3$C(O)CH$_2$CH$_2$CH$_2$CH$_2$CH$_2$CH$_2$C(CH$_3$)$_2$COOK, CH$_3$C(O)CH$_2$CH$_2$CH$_2$CH$_2$CH$_2$CH$_2$CH$_2$CH$_2$SO$_3$Na,
CH$_3$C(O)CH$_2$CH$_2$CH$_2$CH$_2$CH$_2$CH$_2$CH$_2$SO$_3$Na,
CH$_3$C(O)CH$_2$CH$_2$CH$_2$CH$_2$CH$_2$CH$_2$CH$_2$SO$_3$Na,
CH$_3$C(O)CH$_2$CH$_2$CH$_2$CH$_2$CH$_2$CH$_2$SO$_3$Na,
CH$_3$C(O)CH$_2$CH$_2$CH$_2$CH$_2$CH$_2$SO$_3$Na,
CH$_3$C(O)CH$_2$CH$_2$CH$_2$CH$_2$SO$_3$Na,
CH$_3$C(O)CH$_2$CH$_2$CH$_2$CH$_2$CH$_2$CH$_2$CH$_2$CH$_2$CH$_2$CH$_2$CH$_2$SO$_3$Na,
CH$_3$C(O)CH$_2$CH$_2$CH$_2$CH$_2$CH$_2$CH$_2$CH$_2$CH$_2$CH$_2$CH$_2$CH$_2$CH$_2$CH$_2$CH$_2$CH$_2$SO$_3$Na,
CH$_3$C(O)CH$_2$CH$_2$CH$_2$CH$_2$CH$_2$CH$_2$CH$_2$CH$_2$CH$_2$SO$_3$Na,
(CH$_3$)$_3$CC(O)CH$_2$CH$_2$CH$_2$CH$_2$CH$_2$CH$_2$CH$_2$CH$_2$CH$_2$SO$_3$Na,
(CH$_3$)$_2$CHC(O)CH$_2$CH$_2$CH$_2$CH$_2$CH$_2$CH$_2$CH$_2$CH$_2$CH$_2$SO$_3$Na,
(CH$_2$)$_5$CHC(O)CH$_2$CH$_2$CH$_2$CH$_2$CH$_2$CH$_2$CH$_2$CH$_2$CH$_2$SO$_3$Na,
CH$_3$C(O)CH$_2$CH$_2$CH$_2$CH$_2$CH$_2$CH$_2$CH$_2$CH$_2$SO$_3$Na,
CH$_3$C(O)CH$_2$CH$_2$CH$_2$CH$_2$CH$_2$CH$_2$CH$_2$SO$_3$Na,
CH$_3$C(O)CH$_2$CH$_2$CH$_2$CH$_2$CH$_2$CH$_2$SO$_3$Na,
CH$_3$C(O)CH$_2$CH$_2$CH$_2$CH$_2$CH$_2$SO$_3$Na,
CH$_3$C(O)CH$_2$CH$_2$CH$_2$CH$_2$SO$_3$Na,
CH$_3$C(O)CH$_2$CH$_2$CH$_2$SO$_3$Na,
CH$_3$C(O)CH$_2$CH$_2$SO$_3$Na,
CH$_3$C(O)CH$_2$SO$_3$Na,
CH$_3$C(O)CH$_2$CH$_2$CH$_2$CH$_2$CH$_2$CH$_2$CH$_2$CH$_2$CH$_2$OCH$_2$CH$_2$CH$_2$SO$_3$Na,
CH$_3$C(O)CH$_2$CH$_2$CH$_2$CH$_2$CH$_2$CH$_2$CH$_2$CH$_2$CH$_2$C(O)NHCH$_2$SO$_3$Na,
CH$_3$C(O)CH$_2$CH$_2$CH$_2$CH$_2$CH$_2$CH$_2$CH$_2$CH$_2$NHC(O)CH$_2$SO$_3$Na,
CH$_3$C(O)CH$_2$CH$_2$CH$_2$CH$_2$CH$_2$CH$_2$CH$_2$CH$_2$CH$_2$C(O)SO$_3$Na,
CH$_3$C(O)CH$_2$CH$_2$CH$_2$CH$_2$CH$_2$CH$_2$CH$_2$CH$_2$CH$_2$C(O)OCH$_2$SO$_3$Na,
CH$_3$C(O)CH$_2$CH$_2$CH$_2$CH$_2$CH$_2$CH$_2$CH$_2$CH$_2$CH$_2$OC(O)CH$_2$SO$_3$Na,
CH$_3$C(O)CH$_2$CH$_2$CH$_2$CH$_2$CH$_2$CH$_2$CH$_2$CH$_2$CH$_2$SO$_3$H,
CH$_3$C(O)CH$_2$CH$_2$CH$_2$CH$_2$CH$_2$CH$_2$CH$_2$CH$_2$CH$_2$SO$_3$K,
CH$_3$C(O)CH$_2$CH$_2$CH$_2$CH$_2$CH$_2$CH$_2$CH$_2$CH$_2$CH$_2$SO$_3$Li,
CH$_3$C(O)CH$_2$CH$_2$CH$_2$CH$_2$CH$_2$CH$_2$CH$_2$CH$_2$CH$_2$SO$_3$NH$_4$, and
CH$_3$C(O)CH$_2$CH$_2$CH$_2$CH$_2$CH$_2$CH$_2$CH$_2$CH$_2$C(CH$_3$)$_2$SO$_3$Na.

The surfactant (d) is a novel compound, and may be produced by any of the following production methods, for example.

The surfactant (d) may be suitably produced by a production method including:

a step (11d) of reacting a compound (10d) represented by the following formula:

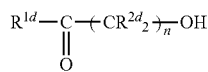

(wherein $R^{1d}$, $R^{2d}$, and n are defined as described above) and a sultone represented by the following formula:

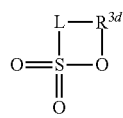

(wherein $R^{3d}$ is defined as described above; L is a single bond, —CO$_2$—B—*, —OCO—B—*, —CONR$^{6d}$—B—*, —NR$^{6d}$CO—B—*, or —CO— other than the carbonyl groups in —CO$_2$—B—, —OCO—B—, —CONR$^{6d}$—B—, and —NR$^{6d}$CO—B—, wherein B is a single bond or an alkylene group having 1 to 10 carbon atoms and optionally having a substituent, $R^{6d}$ is H or an alkyl group having 1 to 4 carbon atoms and optionally having a substituent; and * indicates the side bonded to —S(=O)$_2$— in the formula) to provide a compound (11d) represented by the following formula:

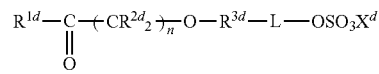

wherein $R^{1d}$ to $R^{3d}$, n, and $X^d$ are defined as described above; L is a single bond, —CO$_2$—B—*, —OCO—B—*, —CONR$^{6d}$—B—*, —NR$^{6d}$CO—B—*, or —CO— other than the carbonyl groups in —CO$_2$—B—, —OCO—B—, —CONR$^{6d}$—B—, and —NR$^{6d}$CO—B—, wherein B is a single bond or an alkylene group having 1 to 10 carbon atoms and optionally having a substituent, $R^{6d}$ is H or an alkyl group having 1 to 4 carbon atoms and optionally having a substituent; and * indicates the side bonded to —OSO$_3$X$^d$ in the formula.

The reaction in the step (11d) may be performed in the presence of a base.

Examples of the base include sodium hydride, sodium hydroxide, potassium hydroxide, and triethylamine. The base may be used in an amount of 0.5 to 20 mol based on 1 mol of the compound (10d).

The reaction in the step (11d) may be performed in a solvent.

The solvent is preferably an organic solvent, and more preferably an aprotic polar solvent. Examples of the organic solvent include ethers, aromatic compounds, nitriles, and halogenated hydrocarbons.

Examples of the ether include diethyl ether, tetrahydrofuran, dioxane, and diethylene glycol diethyl ether, of which diethyl ether and tetrahydrofuran are preferred.

Examples of the aromatic compound include benzene, toluene, and xylene, of which benzene is preferred.

Examples of the nitrile include acetonitrile, propionitrile, butyronitrile, isobutyronitrile, and benzonitrile, of which acetonitrile is preferred.

Examples of the halogenated hydrocarbon include dichloromethane, dichloroethane, chloroform, chlorobenzene, and o-dichlorobenzene, of which dichloromethane and chloroform are preferred.

The reaction temperature in the step (11d) is preferably −78 to 150° C., and more preferably −20 to 100° C.

The reaction pressure in the step (11d) is preferably 0 to 10 MPa, and more preferably 0 to 1.0 MPa.

The reaction duration in the step (11d) is preferably 0.1 to 72 hours, and more preferably 0.1 to 48 hours.

The surfactant (d) may also be suitably produced by a production method including:

a step (21d) of oxidizing a compound (20d) represented by the following formula:

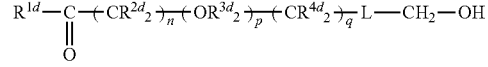

(wherein $R^{1d}$ to $R^{4d}$, n, p, and q are defined as described above; L is a single bond, —CO$_2$—B—*, —OCO—B—*, —CONR$^{6d}$—B—*, —NR$^{6d}$CO—B—*, or —CO— other than the carbonyl groups in —CO$_2$—B—, —OCO—B—, —CONR$^{6d}$—B—, and —NR$^{6d}$CO—B—, wherein B is a single bond or an alkylene group having 1 to 10 carbon atoms and optionally having a substituent, $R^{6d}$ is H or an alkyl group having 1 to 4 carbon atoms and optionally having a substituent; and * indicates the side bonded to —CH$_2$—OH in the formula)

to provide a compound (21d) represented by the following formula:

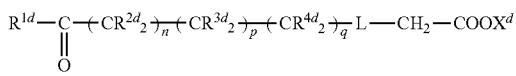

wherein $R^{1d}$ to $R^{4d}$, n, p, q, and $X^d$ are defined as described above; L is a single bond, —CO$_2$—B—*, —OCO—B—*, —CONR$^{6d}$—B—*, —NR$^{6d}$CO—B—*, or —CO— other than the carbonyl groups in —CO$_2$—B—, —OCO—B—, —CONR$^{6d}$—B—, and —NR$^{6d}$CO—B—, wherein B is a single bond or an alkylene group having 1 to 10 carbon atoms and optionally having a substituent, $R^{6d}$ is H or an alkyl group having 1 to 4 carbon atoms and optionally having a substituent; and * indicates the side bonded to —CH$_2$—COOX$^d$ in the formula.

The oxidation in the step (21d) may performed by causing a nitrosating agent to act on the compound (20d).

The nitrosating agent may be sodium nitrite, nitrosyl sulfuric acid, isoamyl nitrite or the like.

The nitrosating agent may be used in an amount of 0.5 to 10 mol based on 1 mol of the compound (20d).

The oxidation in the step (21d) may be performed in a solvent. The solvent may be trifluoroacetic acid, acetonitrile, or the like.

The oxidation temperature in the step (21d) is preferably −78 to 200° C., and more preferably −20 to 100° C.

The oxidation pressure in the step (21d) is preferably 0 to 10 MPa, and more preferably 0 to 1.0 MPa.

The oxidation duration in the step (21d) is preferably 0.1 to 72 hours, and more preferably 0.1 to 24 hours.

The compound (10d) and the compound (20d) may be produced by a production method including:

a step (101d) of hydroxylating a compound (100d) represented by the following formula:

$R^{11d}$—CH=CH—$Y^{1d}$—OH (wherein $R^{11d}$ is H, a linear or branched alkyl group having 1 or more carbon atoms and optionally having a substituent, or a cyclic alkyl group having 3 or more carbon atoms and optionally having a substituent, and optionally contains a monovalent or divalent heterocycle or optionally forms a ring when having 3 or more carbon atoms; $Y^{1d}$ is —(CR$^{2d}_2$)$_n$— or —(CR$^{2d}_2$)$_n$—(OR$^{3d}$)$_p$—(CR$^{4d}_2$)$_q$-L-CH$_2$—, wherein $R^{2d}$ to $R^{4d}$, n, L, p, and q are defined as described above; L is a single bond, —CO$_2$—B—*, —OCO—B—*, —CONR$^{6d}$—B—*, —NR$^{6d}$CO—B—*, or —CO— other than the carbonyl groups in —CO$_2$—B—, —OCO—B—, —CONR$^{6d}$—B—, and —NR$^{6d}$CO—B—, wherein B is a single bond or an alkylene group having 1 to 10 carbon atoms and optionally having a substituent, $R^{6d}$ is H or an alkyl group having 1 to 4 carbon atoms and optionally having a substituent; and * indicates the side bonded to —CH$_2$— in the formula) to provide a compound (101d) represented by the following formula:

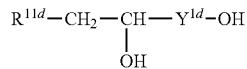

(wherein $R^{11d}$ and $Y^{1d}$ are defined as described above); and a step (102d) of oxidizing the compound (101d) to provide a compound (102d) represented by the following formula:

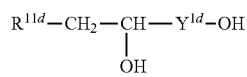

(wherein $R^{11d}$ and $Y^{1d}$ are defined as described above).

The alkyl group for $R^{11d}$ is preferably free from a carbonyl group.

In the alkyl group for $R^{11d}$, 75% or less of the hydrogen atoms bonded to the carbon atoms may be replaced by halogen atoms, 50% or less thereof may be replaced by halogen atoms, or 25% or less thereof may be replaced by halogen atoms. The alkyl group is preferably a non-halogenated alkyl group free from halogen atoms such as fluorine atoms and chlorine atoms.

The alkyl group preferably contains no substituent.

$R^{11d}$ is preferably H, a linear or branched alkyl group having 1 to 9 carbon atoms and optionally having a substituent, or a cyclic alkyl group having 3 to 9 carbon atoms and optionally having a substituent, more preferably H, a linear or branched alkyl group having 1 to 9 carbon atoms and free from a carbonyl group, or a cyclic alkyl group having 3 to 9 carbon atoms and free from a carbonyl group, still more preferably H or a linear or branched alkyl group having 1 to 9 carbon atoms and not having a substituent, further preferably H, a methyl group (—CH$_3$), or an ethyl group (—C$_2$H$_5$), particularly preferably H or a methyl group (—CH$_3$), and most preferably H.

The hydroxylation in the step (101b) may be performed by a method (1d) in which iron(II) phthalocyanine (Fe(Pc)) and sodium borohydride are caused to act on the compound (100d) in an oxygen atmosphere or a method (2d) in which isopinocampheylborane (IpcBH$_2$) is caused to act on the compound (100d) and then the resulting intermediate (dialkyl borane) is oxidized.

In the method (1d), iron(II) phthalocyanine may be used in a catalytic amount, and may be used in an amount of 0.001 to 1.2 mol based on 1 mol of the compound (100b).

In the method (1d), sodium borohydride may be used in an amount of 0.5 to 20 mol based on 1 mol of the compound (100d).

The reaction in the method (1d) may be performed in a solvent. The solvent is preferably an organic solvent, and examples thereof include ethers, halogenated hydrocarbons, aromatic hydrocarbons, nitriles, and nitrogen-containing polar organic compounds.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

Examples of the nitrile include acetonitrile, propionitrile, butyronitrile, isobutyronitrile, and benzonitrile, of which acetonitrile is preferred.

Examples of the nitrogen-containing polar organic compound include N,N-dimethylformamide, N,N-dimethylacetamide, N-methyl-2-pyrrolidone, 2-pyrrolidone, and 1,3-dimethyl-2-imidazolidinone, of which N,N-dimethylformamide, N,N-dimethylacetamide, and N-methyl-2-pyrrolidone are preferred.

The reaction temperature in the method (1d) is preferably −78 to 200° C., and more preferably 0 to 150° C.

The reaction pressure in the method (1d) is preferably 0 to 5.0 MPa, and more preferably 0.1 to 1.0 MPa.

The reaction duration in the method (1d) is preferably 0.1 to 72 hours, and more preferably 0.1 to 48 hours.

In the method (2d), isopinocampheylborane may be used in an amount of 1.0 to 10.0 mol based on 1 mol of the compound (100d).

The reaction of the compound (100d) and isopinocampheylborane may be performed in a solvent. The solvent is preferably an organic solvent, and examples thereof include ethers, halogenated hydrocarbons, and aromatic hydrocarbons.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

The reaction temperature of the compound (100d) and isopinocampheylborane is preferably −78 to 200° C., and more preferably 0 to 150° C.

The reaction pressure of the compound (100d) and isopinocampheylborane is preferably 0 to 5.0 MPa, and more preferably 0.1 to 1.0 MPa.

The duration of the reaction of the compound (100d) and isopinocampheylborane is preferably 0.1 to 72 hours, and more preferably 0.1 to 48 hours.

The oxidation in the method (2d) may be performed by causing an oxidizing agent to act on the intermediate. An example of the oxidizing agent is hydrogen peroxide. The oxidizing agent may be used in an amount of 0.7 to 10 mol based on 1 mol of the intermediate.

The oxidation in the method (2d) may be performed in a solvent. Examples of the solvent include water, methanol, and ethanol, of which water is preferred.

The oxidation temperature in the step (2d) is preferably 0 to 100° C., and more preferably 0 to 80° C.

The oxidation pressure in the method (2d) is preferably 0 to 5.0 MPa, and more preferably 0.1 to 1.0 MPa.

The oxidation duration in the step (2d) is preferably 0.1 to 72 hours, and more preferably 0.1 to 48 hours.

Examples of the method of oxidizing the compound (101d) in the step (102d) include (a) a method of using Jones reagent ($CrO_3/H_2SO_4$) (Jones oxidation), (d) a method of using Dess-Martin periodinane (DMP) (Dess-Martin oxidation), (c) a method of using pyridinium chlorochromate (PCC), (d) a method of causing a bleaching agent (about 5% to 6% aqueous solution of NaOCl) to act in the presence of a nickel compound such as $NiCl_2$, and (e) a method of causing a hydrogen acceptor such as an aldehyde or a ketone to act in the presence of an aluminum catalyst such as $Al(CH_3)_3$ or $Al[OCH(CH_3)_2]_3$ (Oppenauer oxidation).

The oxidation in the step (102d) may be performed in a solvent. The solvent is preferably water or an organic solvent, and examples thereof include water, ketones, ethers, halogenated hydrocarbons, aromatic hydrocarbons, and nitriles.

Examples of the ketones include acetone, methyl ethyl ketone, methyl isobutyl ketone, cyclohexanone, and diacetone alcohol, of which acetone is preferred.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

Examples of the nitrile include acetonitrile, propionitrile, butyronitrile, isobutyronitrile, and benzonitrile, of which acetonitrile is preferred.

The oxidation temperature in the step (102d) is preferably −78 to 200° C., and may appropriately be selected in accordance with the method used.

The oxidation pressure in the step (102d) is preferably 0 to 5.0 MPa, and may appropriately be selected in accordance with the method used.

The oxidation duration in the step (102d) is preferably 0.1 to 72 hours, and may appropriately be selected in accordance with the method used.

The compound (10d) and the compound (20d) may also be produced by a production method including a step (201d) of ozonolyzing a compound (200d) represented by the following formula:

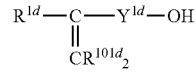

(wherein $R^{1d}$ and $Y^{1d}$ are defined as described above; and $R^{101b}$ is an organic group); and to provide a compound (201d) represented by the following formula:

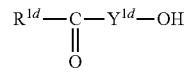

wherein $R^{1d}$ and $Y^{1d}$ are defined as described above.

$R^{101d}$ is preferably an alkyl group having 1 to 20 carbon atoms. The two $R^{101d}$ may be the same as or different from each other.

The ozonolysis in the step (201d) may be performed by causing ozone to act on the compound (200d), followed by post-treatment with a reducing agent.

The ozone may be generated by dielectric barrier discharge in oxygen gas.

Examples of the reducing agent used in the post-treatment include zinc, dimethyl sulfide, thiourea, and phosphines, of which phosphorines are preferred.

The ozonolysis in the step (201d) may be performed in a solvent. The solvent is preferably water or an organic solvent, and examples thereof include water, alcohols, carboxylic acids, ethers, halogenated hydrocarbons, and aromatic hydrocarbons.

Examples of the alcohol include methanol, ethanol, 1-propanol, and isopropanol. Of these, methanol and ethanol are preferred.

Examples of the carboxylic acids include acetic acid and propionic acid. Of these, acetic acid is preferred.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

The ozonolysis temperature in the step (201d) is preferably −78 to 200° C., and more preferably 0 to 150° C.

The ozonolysis pressure in the step (201d) is preferably 0 to 5.0 MPa, and more preferably 0.1 to 1.0 MPa.

The ozonolysis duration in the step (201d) is preferably 0.1 to 72 hours, and more preferably 0.1 to 48 hours.

The compound (10d) and the compound (20d) may also be produced by a production method including:

a step (301d) of epoxidizing a compound (300d) represented by the following formula:

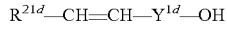

(wherein $Y^{1d}$ is defined as described above; and $R^{21d}$ is H, a linear or branched alkyl group having 1 or more carbon atoms and optionally having a substituent, or a cyclic alkyl group having 3 or more carbon atoms and optionally having a substituent, and optionally contains a monovalent or divalent heterocycle or optionally forms a ring when having 3 or more carbon atoms) to provide a compound (301d) represented by the following formula:

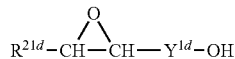

(wherein $R^{21d}$ and $Y^{1d}$ are defined as described above);

a step (302d) of reacting the compound (301d) with a lithium dialkylcopper represented by $R^{22d}{}_2CuLi$ (wherein $R^{22b}$ is a linear or branched alkyl group having 1 or more carbon atoms and optionally having a substituent or a cyclic alkyl group having 3 or more carbon atoms and optionally having a substituent, and optionally contains a monovalent or divalent heterocycle or optionally forms a ring when having 3 or more carbon atoms) to provide a compound (302b) represented by the following formula:

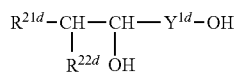

(wherein $R^{21d}$, $R^{22d}$, and $Y^{1d}$ are defined as described above); and a step (303d) of oxidizing the compound (302d) to provide a compound (303d) represented by the following formula:

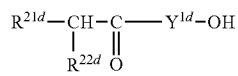

(wherein $R^{21d}$, $R^{22d}$, and $Y^{1d}$ are defined as described above).

The alkyl group for $R^{21d}$ is preferably free from a carbonyl group.

In the alkyl group for $R^{21d}$, 75% or less of the hydrogen atoms bonded to the carbon atoms may be replaced by halogen atoms, 50% or less thereof may be replaced by halogen atoms, or 25% or less thereof may be replaced by halogen atoms. The alkyl group is preferably a non-halogenated alkyl group free from halogen atoms such as fluorine atoms and chlorine atoms.

The alkyl group preferably contains no substituent.

$R^{21d}$ is preferably H, a linear or branched alkyl group having 1 to 8 carbon atoms and optionally having a substituent, or a cyclic alkyl group having 3 to 8 carbon atoms and optionally having a substituent, more preferably H, a linear or branched alkyl group having 1 to 8 carbon atoms and free from a carbonyl group, or a cyclic alkyl group having 3 to 8 carbon atoms and free from a carbonyl group, still more preferably H or a linear or branched alkyl group having 1 to 8 carbon atoms and not having a substituent, particularly preferably H or a methyl group (—CH₃), and most preferably H.

The alkyl group for $R^{22d}$ is preferably free from a carbonyl group.

In the alkyl group for $R^{22d}$, 75% or less of the hydrogen atoms bonded to the carbon atoms may be replaced by halogen atoms, 50% or less thereof may be replaced by halogen atoms, or 25% or less thereof may be replaced by halogen atoms. The alkyl group is preferably a non-halogenated alkyl group free from halogen atoms such as fluorine atoms and chlorine atoms.

The alkyl group preferably contains no substituent.

$R^{22d}$ is preferably a linear or branched alkyl group having 1 to 9 carbon atoms and optionally having a substituent or a cyclic alkyl group having 3 to 9 carbon atoms and optionally having a substituent, more preferably a linear or branched alkyl group having 1 to 9 carbon atoms and free from a carbonyl group or a cyclic alkyl group having 3 to 9 carbon atoms and free from a carbonyl group, still more preferably a linear or branched alkyl group having 1 to 9 carbon atoms and not having a substituent, particularly preferably a methyl group (—CH₃) or an ethyl group (—C₂H₅), and most preferably a methyl group (—CH₃).

The two $R^{22d}$ may be the same as or different from each other.

The total number of carbon atoms of $R^{21d}$ and $R^{22d}$ is preferably 1 to 7, more preferably 1 to 2, and most preferably 1.

The epoxidation in the step (301d) may be performed by causing an epoxidizing agent to act on the compound (300d).

Examples of the epoxidizing agent include peroxy acids such as meta-chloroperbenzoic acid (m-CPBA), perbenzoic acid, hydrogen peroxide, and tert-butyl hydroperoxide, dimethyl dioxolane, and methyl trifluoromethyl dioxolane, of which peroxy acids are preferred, and meta-chloroperbenzoic acid is more preferred.

The epoxidizing agent may be used in an amount of 0.5 to 10.0 mol based on 1 mol of the compound (300d).

The epoxidation in the step (301d) may be performed in a solvent. The solvent is preferably an organic solvent, and examples thereof include ketones, ethers, halogenated hydrocarbons, aromatic hydrocarbons, nitriles, pyridines, nitrogen-containing polar organic compounds, and dimethyl sulfoxide, of which dichloromethane is preferred.

Examples of the ketones include acetone, methyl ethyl ketone, methyl isobutyl ketone, cyclohexanone, and diacetone alcohol, of which acetone is preferred.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

Examples of the nitrile include acetonitrile, propionitrile, butyronitrile, isobutyronitrile, and benzonitrile, of which acetonitrile is preferred.

Examples of the nitrogen-containing polar organic compound include N,N-dimethylformamide, N,N-dimethylacetamide, N-methyl-2-pyrrolidone, 2-pyrrolidone, and 1,3-dimethyl-2-imidazolidinone, of which N,N-dimethylformamide, N,N-dimethylacetamide, and N-methyl-2-pyrrolidone are preferred.

The epoxidation temperature in the step (301d) is preferably −78 to 200° C., and more preferably −40 to 150° C.

The epoxidation pressure in the step (301d) is preferably 0 to 5.0 MPa, and more preferably 0.1 to 1.0 MPa.

The epoxidation duration in the step (301d) is preferably 0.1 to 72 hours, and more preferably 0.1 to 48 hours.

In the step (302d), the lithium dialkylcopper may be used in an amount of 0.5 to 10.0 mol based on 1 mol of the compound (301d).

The reaction in the step (302d) may be performed in a solvent. The solvent is preferably an organic solvent, and examples thereof include ethers, halogenated hydrocarbons, and aromatic hydrocarbons.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

The reaction temperature in the step (302d) is preferably −78 to 200° C., and more preferably −40 to 150° C.

The reaction pressure in the step (302d) is preferably 0 to 5.0 MPa, and more preferably 0.1 to 1.0 MPa.

The reaction duration in the step (302d) is preferably 0.1 to 72 hours, and more preferably 0.1 to 48 hours.

Examples of the method of oxidizing the compound (302d) in the step (303d) include (a) a method of using Jones reagent ($CrO_3/H_2SO_4$) (Jones oxidation), (b) a method of using Dess-Martin periodinane (DMP) (Dess-Martin oxidation), (c) a method of using pyridinium chlorochromate (PCC), (d) a method of causing a bleaching agent (about 5% to 6% aqueous solution of NaOCl) to act in the presence of a nickel compound such as $NiCl_2$, and (e) a method of causing a hydrogen acceptor such as an aldehyde and a ketone to act in the presence of an aluminum catalyst such as $Al(CH_3)_3$ or $Al[OCH(CH_3)_2]_3$ (Oppenauer oxidation).

The oxidation in the step (303d) may be performed in a solvent. The solvent is preferably water or an organic solvent, and examples thereof include water, ketones, alcohols, ethers, halogenated hydrocarbons, aromatic hydrocarbons, and nitriles.

Examples of the ketones include acetone, methyl ethyl ketone, methyl isobutyl ketone, cyclohexanone, and diacetone alcohol, of which acetone is preferred.

Examples of the alcohol include methanol, ethanol, 1-propanol, and isopropanol. Of these, methanol and ethanol are preferred.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the aromatic hydrocarbon include benzene, toluene, and xylene, of which benzene and toluene are preferred.

Examples of the nitrile include acetonitrile, propionitrile, butyronitrile, isobutyronitrile, and benzonitrile, of which acetonitrile is preferred.

The oxidation temperature in the step (303d) is preferably −78 to 200° C., and may appropriately be selected in accordance with the method used.

The oxidation pressure in the step (303d) is preferably 0 to 5.0 MPa, and may appropriately be selected in accordance with the method used.

The oxidation duration in the step (303d) is preferably 0.1 to 72 hours, and may appropriately be selected in accordance with the method used.

The compound (10d) and the compound (20d) may also be produced by a production method including a step (401d) of oxidizing a compound (100d) represented by the following formula:

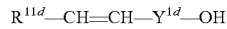

$$R^{11d}-CH=CH-Y^{1d}-OH$$

(wherein $R^{11d}$ and $Y^{1d}$ are defined as described above) to provide a compound (401d) represented by the following formula:

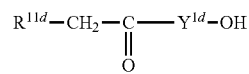

$$R^{11d}-CH_2-\underset{\underset{O}{\|}}{C}-Y^{1d}-OH$$

(wherein $R^{11d}$ and $Y^{1d}$ are defined as described above).

The oxidation in the step (401d) may be performed by causing an oxidizing agent to act on the compound (100d) in the presence of water and a palladium compound.

Examples of the oxidizing agent include monovalent or divalent copper salts such as copper chloride, copper acetate, copper cyanide, and copper trifluoromethanethiolate, iron salts such as iron chloride, iron acetate, iron cyanide, iron trifluoromethanethiolate, and hexacyanoferrates, benzoquinones such as 1,4-benzoquinone, 2,3-dichloro-5,6-dicyano-1,4-benzoquinone, tetrachloro-1,2-benzoquinone, and tetrachloro-1,4-benzoquinone, $H_2O_2$, $MnO_2$, $KMnO_4$, $RuO_4$, m-chloroperbenzoic acid, and oxygen. Of these, copper salts, iron salts, and benzoquinones are preferred, and copper chloride, iron chloride, and 1,4-benzoquinone are more preferred.

The oxidizing agent may be used in an amount of 0.001 to 10 mol based on 1 mol of the compound (100d).

The water may be used in an amount of 0.5 to 1,000 mol based on 1 mol of the compound (100d).

An example of the palladium compound is palladium dichloride. The palladium compound may be used in a catalytic amount, and may be used in an amount of 0.0001 to 1.0 mol based on 1 mol of the compound (100d).

The oxidation in the step (401d) may be performed in a solvent. Examples of the solvent include water, esters, aliphatic hydrocarbons, aromatic hydrocarbons, alcohols, carboxylic acids, ethers, halogenated hydrocarbons, nitrogen-containing polar organic compounds, nitriles, dimethyl sulfoxide, and sulfolane.

Examples of the esters include ethyl acetate, butyl acetate, ethylene glycol monomethyl ether acetate, and propylene glycol monomethyl ether acetate (PGMEA, also known as 1-methoxy-2-acetoxypropane), of which ethyl acetate is preferred.

Examples of the aliphatic hydrocarbons include hexane, cyclohexane, heptane, octane, nonane, decane, undecane, dodecane, and mineral spirits, of which cyclohexane and heptane are preferred.

Examples of the aromatic hydrocarbon include benzene, toluene, and xylene, of which benzene and toluene are preferred.

Examples of the alcohol include methanol, ethanol, 1-propanol, and isopropanol.

Examples of the carboxylic acids include acetic acid and propionic acid. Of these, acetic acid is preferred.

Examples of the ether include diethyl ether, tetrahydrofuran, dioxane, and diethylene glycol diethyl ether, of which diethyl ether and tetrahydrofuran are preferred.

Examples of the halogenated hydrocarbon include dichloromethane, dichloroethane, chloroform, chlorobenzene, and o-dichlorobenzene, of which dichloromethane and chloroform are preferred.

Examples of the nitrogen-containing polar organic compound include N,N-dimethylformamide, N,N-dimethylacetamide, N-methyl-2-pyrrolidone, 2-pyrrolidone, and 1,3-dimethyl-2-imidazolidinone, of which N,N-dimethylformamide, N,N-dimethylacetamide, and N-methyl-2-pyrrolidone are preferred.

Examples of the nitrile include acetonitrile, propionitrile, butyronitrile, isobutyronitrile, and benzonitrile, of which acetonitrile is preferred.

The oxidation temperature in the step (401d) is preferably −78 to 200° C., and more preferably −20 to 150° C.

The oxidation pressure in the step (401d) is preferably 0 to 10 MPa, and more preferably 0.1 to 5.0 MPa.

The oxidation duration in the step (401d) is preferably 0.1 to 72 hours, and more preferably 0.1 to 48 hours.

The surfactant (d) may also be produced by a production method including:

a step (31d) of oxidizing a compound (30d) represented by the following formula:

$$R^{11d}-CH=CH-(CR^{2d}_2)_n-(OR^{3d})_p-(CR^{4d}_2)_q-L-COOX^d$$

(wherein $R^{2d}$ to $R^{4d}$, $R^{11d}$, n, p, q, and $X^d$ are defined as described above; L is a single bond, —$CO_2$—B—*, —OCO—B—*, —$CONR^{6d}$—B—*, —$NR^{6d}CO$—B—*, or —CO— other than the carbonyl groups in —$CO_2$—B—, —OCO—B—, —$CONR^{6d}$—B—, and —$NR^{6d}CO$—B—, wherein B is a single bond or an alkylene group having 1 to 10 carbon atoms and optionally having a substituent, $R^{6d}$ is H or an alkyl group having 1 to 4 carbon atoms and optionally having a substituent; and the alkylene group more preferably has 1 to 5 carbon atoms; $R^{6d}$ is more preferably H or a methyl group; and * indicates the side bonded to —$COOX^d$ in the formula) to provide a compound (31d) represented by the following formula:

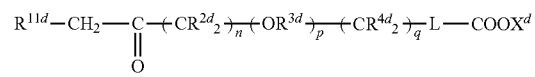

(wherein $R^{2d}$ to $R^{4d}$, L, $R^{11d}$, n, p, q, and $X^d$ are defined as described above).

The oxidation in the step (31d) may be performed by causing an oxidizing agent to act on the compound (30d) in the presence of water and a palladium compound under the same conditions as in the oxidation in the step (401d).

In any of the production methods described above, after the completion of each step, the solvent may be distilled off, or distillation, purification or the like may be performed to increase the purity of the resulting compounds. For the resulting compounds in which $X^d$ is H, such as those containing —$SO_3H$, —COOH, or the like, the compounds may be brought into contact with an alkali such as sodium carbonate or ammonia to covert these groups into the form of a salt.

In the removal method of the present disclosure, two or more of the hydrocarbon surfactants may be used at the same time.

The hydrocarbon surfactant is preferably at least one selected from the group consisting of the surfactant (a) represented by the formula (a), the surfactant (b) represented by the formula (b), the surfactant (c) represented by the formula (c), and the surfactant (d) represented by the above formula (d).

In the removal method of the present disclosure, the hydrocarbon surfactant is particularly suitably a carboxylic acid-type hydrocarbon surfactant because the discharge water does not contain sulfur-containing impurities derived from sulfonic acid-type surfactants.

Examples of the carboxylic acid-type hydrocarbon surfactant include those having a group in which a carboxyl group or a hydrogen atom of the carboxyl group is substituted with M (metal atom, $NR^{11}_4$, imidazolium optionally having a substituent, pyridinium optionally having a substituent, or phosphonium optionally having a substituent) or the like in the formula (α) described above. For example, among the hydrocarbon surfactants described above, a hydrocarbon surfactant having a group in which a carboxyl group or a hydrogen atom of the carboxyl group is substituted with M (wherein M is the same as above) in the formula (α) described above.

The carboxylic acid-type hydrocarbon surfactant is preferably at least one selected from the group consisting of the compound (α), a com compound in which A of the formula (1) is —COOM in the surfactant (1) represented by the formula (1), the surfactant (c) represented by the formula (c), and the surfactant (d) represented by the formula (d). The carboxylic acid-type hydrocarbon surfactant is particularly preferably the compound (α).

Although the embodiments have been described above, it will be understood that various changes in form and details are possible without departing from the gist and scope of the claims.

EXAMPLES

The present disclosure is described with reference to experimental examples, but the present disclosure is not intended to be limited by these examples.

Each numerical value of the experimental example was measured by the following method.

Average Primary Particle Size (Nm)

The PTFE aqueous dispersion was diluted with water to a solid content of 0.15% by mass. The transmittance of incident light at 550 nm relative to the unit length of the resulting diluted latex was determined and the number-based length average primary particle size was determined by measuring the Feret diameter with a transmission electron microscope image. Based on these values, a calibration curve is drawn. Using this calibration curve, the average primary particle size of the PTFE particles in the PTFE aqueous dispersion was determined from the measured transmittance of the projected light at 550 nm of each sample.

PTFE Solid Content (% by Mass)

In an air dryer, 1 g of PTFE aqueous dispersion was dried at a condition of 150° C. for 60 minutes, and the ratio of the mass of the non-volatile matter to the mass of the aqueous dispersion (1 g) was expressed by percentage and taken as the solid concentration thereof.

Standard Specific Gravity (SSG)

Using a sample molded in conformity with ASTM D 4895-89, the SSG was determined by the water replacement method in conformity with ASTM D 792.

Content of the Compound Represented by the General Formula (1) or (2)

The content of the compound was measured under the following conditions using liquid chromatography-mass spectrometry.

[Method of Measuring Content of Compound Represented by General Formula (1)]

Extraction from Aqueous Dispersion

The amount of the solid content in the aqueous dispersion was determined, and the aqueous dispersion in an amount equivalent to 0.5 g of the solid PTFE was put into a 100-mL screw tube. Thereafter, water and methanol were added thereto such that the extraction solvent was to be 40 g (43.14 mL) having a water/methanol ratio by vol % of 50/50 including the water originally contained in the aqueous dispersion. Thereafter, the mixture was well shaken until coagulation occurred. The solid was removed and the liquid phase was centrifuged at 4,000 rpm for one hour, and then the supernatant containing the compound represented by the general formula (1) was extracted.

Extraction from Powder

To 10 g (12.6 mL) of methanol, 1 g of powder was added and ultrasonication was performed on the mixture for 60 minutes, and then the supernatant containing the compound represented by the general formula (1) was extracted.

Measurement of Content of Compound Represented by General Formula (1) Contained in Extract The content of the compound represented by the general formula (1) contained in the extract was determined by conversion in terms of perfluorooctanoic acid equivalent.

Calibration Curve of Perfluorooctanoic Acid

Five methanol standard solutions of perfluorooctanoic acid having known concentrations within 1 ng/mL to 100 ng/mL were prepared, and subjected to analysis using a liquid chromatograph-mass spectrometer (Waters, LC-MS ACQUITY UPLC/TQD). Using the first order approximation from the respective sample concentrations and the peak integral values, the values a and b were determined by the following relational formula (1):

$$A = a \times X + b \quad (1)$$

A: peak area of perfluorooctanoic acid

X: concentration (ng/mL) of perfluorooctanoic acid

Measurement Equipment Configuration and LC-MS Measurement Conditions

TABLE 1

| | LC unit | |
|---|---|---|
| Equipment | Acquity UPLC manufactured by Waters | |
| Column | Acquity UPLC manufactured by Waters BEH C18 1.7 mm (2.1 × 50 mm) | |
| Mobile phase | A CH$_3$CN | |
| | B 20 mM CH$_3$COONH$_4$/H$_2$O | |
| | 0→1.5 min | A:B = 10:90 |
| | 1.5→8.5 min | A:B = 10:90→A:B = 90:10 Linear gradient |
| | 8.5→10 min | A:B = 90:10 |
| Flow rate | 0.4 mL/min | |
| Column temperature | 40° C. | |
| Amount of sample injected | 5 μL | |
| | MS unit | |
| Equipment | TQ Detector | |
| Measurement mode | MRM (Multiple Reaction Monitoring) | |
| Ionization method | Electrospray ionization | |
| | negative mode | |

MRM Measurement Parameters

TABLE 2

| Compound | Precursor | Product |
|---|---|---|
| perfluorooctanoic acid | 413 | 369 |

Content of Compounds Represented by General Formula (1) Having 4 or More and 20 or Less Carbon Atoms Contained in Extract Using a liquid chromatograph-mass spectrometer, compounds represented by the general formula (1) having 4 or more and 20 or less carbon atoms were subjected to analysis. For the extracted liquid phase, the peak areas of the compounds represented by the general formula (1) having the respective numbers of carbon atoms were determined by MRM.

MRM Measurement Parameters

TABLE 3

| Compound name | Number of carbon atoms | Precursor | Product |
|---|---|---|---|
| (H—(CF$_2$)$_3$—COO)M$^1$ | 4 | 195 | 131 |
| (H—(CF$_2$)$_4$—COO)M$^1$ | 5 | 245 | 181 |
| (H—(CF$_2$)$_5$—COO)M$^1$ | 6 | 295 | 231 |
| (H—(CF$_2$)$_6$—COO)M$^1$ | 7 | 345 | 281 |
| (H—(CF$_2$)$_7$—COO)M$^1$ | 8 | 395 | 331 |
| (H—(CF$_2$)$_8$—COO)M$^1$ | 9 | 445 | 381 |
| (H—(CF$_2$)$_9$—COO)M$^1$ | 10 | 495 | 431 |
| (H—(CF$_2$)$_{10}$—COO)M$^1$ | 11 | 545 | 481 |
| (H—(CF$_2$)$_{11}$—COO)M$^1$ | 12 | 595 | 531 |
| (H—(CF$_2$)$_{12}$—COO)M$^1$ | 13 | 645 | 581 |
| (H—(CF$_2$)$_{13}$—COO)M$^1$ | 14 | 695 | 631 |
| (H—(CF$_2$)$_{14}$—COO)M$^1$ | 15 | 745 | 681 |
| (H—(CF$_2$)$_{15}$—COO)M$^1$ | 16 | 795 | 731 |
| (H—(CF$_2$)$_{16}$—COO)M$^1$ | 17 | 845 | 781 |
| (H—(CF$_2$)$_{17}$—COO)M$^1$ | 18 | 895 | 831 |
| (H—(CF$_2$)$_{18}$—COO)M$^1$ | 19 | 945 | 881 |
| (H—(CF$_2$)$_{19}$—COO)M$^1$ | 20 | 995 | 931 |

The content of the compound represented by the general formula (1) having (m+1) carbon atoms in the extract was calculated by the following formula (3). The values a and b in the formula (3) were determined by the formula (1):

$$XCm=((ACm-b)/a)\times((50\times m+45)/413) \quad (3)$$

XCm: content (ng/mL) of compound represented by general formula (1) having (m+1) carbon atoms in extract solution ACm: peak area of compound represented by general formula (1) having (m+1) carbon atoms in extract solution The quantification limit in this measurement is 1 ng/mL.

Content of compound represented by general formula (1) having (m+1) carbon atoms contained in aqueous dispersion The content of the compound represented by the general formula (1) having (m+1) carbon atoms contained in the aqueous dispersion was determined by the following formula (5):

$$ZCm=XCm\times 86.3 \quad (5)$$

ZCm: content (ppb based on PTFE) of compound represented by general formula (1) having (m+1) carbon atoms contained in aqueous dispersion Content of compound represented by general formula (1) having (m+1) carbon atoms contained in powder The content of the compound represented by the general formula (1) having (m+1) carbon atoms contained in the powder was determined by the following formula (4):

$$YCm=XCm\times 12.6 \quad (4)$$

YCm: content (ppb based on PTFE) of compound represented by general formula (1) having (m+1) carbon atoms contained in powder

[Method of Measuring Content of Compound Represented by General Formula (2)]

Extraction from Aqueous Dispersion

The amount of the solid content in the aqueous dispersion was determined, and the aqueous dispersion in an amount equivalent to 0.5 g of the solid PTFE was put into a 100-mL screw tube. Thereafter, water and methanol were added thereto such that the extraction solvent was to be 40 g (43.14 mL) having a water/methanol ratio by vol % of 50/50 including the water originally contained in the aqueous dispersion. Thereafter, the mixture was well shaken until coagulation occurred. The solid was removed and the liquid phase was centrifuged at 4,000 rpm for one hour, and then the supernatant containing the compound represented by the general formula (2) was extracted.

Extraction from Powder

To 10 g (12.6 mL) of methanol, 1 g of powder was added and ultrasonication was performed on the mixture for 60 minutes, and then the supernatant containing the compound represented by the general formula (2) was extracted.

Measurement of Content of Compound Represented by General Formula (2) Contained in Extract The content of the compound represented by the general formula (2) contained in the extract was determined by conversion in terms of perfluorooctanesulfonic acid equivalent.

Calibration Curve of Perfluorooctanesulfonic Acid

Five methanol standard solutions of perfluorooctanesulfonic acid having known concentrations within 1 ng/mL to 100 ng/mL were prepared, and subjected to analysis using a liquid chromatograph-mass spectrometer (Waters, LC-MS ACQUITY UPLC/TQD). Using the first order approximation from the respective sample concentrations and the peak integral values, the values a and b were determined by the following relational formula (1):

$$A=a\times X+b \quad (1)$$

A: peak area of perfluorooctanesulfonic acid
X: concentration (ng/mL) of perfluorooctanesulfonic acid Measurement Equipment Configuration and LC-MS Measurement Conditions

TABLE 4

| | LC unit | |
|---|---|---|
| Equipment | Acquity UPLC manufactured by Waters | |
| Column | Acquity UPLC manufactured by Waters BEH C18 1.7 mm (2.1 × 50 mm) | |
| Mobile phase | A CH$_3$CN | |
| | B 20 mM CH$_3$COONH$_4$/H$_2$O | |
| | 0→1.5 min | A:B = 10:90 |
| | 1.5→8.5 min | A:B = 10:90→A:B = 90:10 Linear gradient |
| | 8.5→10 min | A:B = 90:10 |
| Flow rate | 0.4 mL/min | |
| Column temperature | 40° C. | |
| Amount of sample injected | 5 μL | |

TABLE 4-continued

| MS unit | |
|---|---|
| Equipment | TQ Detecter |
| Measurement mode | MRM (Multiple Reaction Monitoring) |
| Ionization method | Electrospray ionization negative mode |

MRM Measurement Parameters

TABLE 5

| Compound | Precursor | Product |
|---|---|---|
| perfluorooctanesulfonic acid | 499 | 99 |

Content of Compounds Represented by General Formula (2) Having 4 or More and 20 or Less Carbon Atoms Contained in Extract Using a liquid chromatograph-mass spectrometer, compounds represented by the general formula (2) having 4 or more and 20 or less carbon atoms were subjected to analysis. For the extracted liquid phase, the peak areas of the compounds represented by the general formula (2) having the respective numbers of carbon atoms were determined by MRM.

MRM Measurement Parameters

TABLE 6

| Compound name | Number of carbon atoms | Precursor | Product |
|---|---|---|---|
| $H-(CF_2)_4-SO_3)M^2$ | 4 | 281 | 99 |
| $H-(CF_2)_5-SO_3)M^2$ | 5 | 331 | 99 |
| $H-(CF_2)_6-SO_3)M^2$ | 6 | 381 | 99 |
| $H-(CF_2)_7-SO_3)M^2$ | 7 | 431 | 99 |
| $H-(CF_2)_8-SO_3)M^2$ | 8 | 481 | 99 |
| $H-(CF_2)_9-SO_3)M^2$ | 9 | 531 | 99 |
| $H-(CF_2)_{10}-SO_3)M^2$ | 10 | 581 | 99 |
| $H-(CF_2)_{11}-SO_3)M^2$ | 11 | 631 | 99 |
| $H-(CF_2)_{12}-SO_3)M^2$ | 12 | 681 | 99 |
| $H-(CF_2)_{13}-SO_3)M^2$ | 13 | 731 | 99 |
| $H-(CF_2)_{14}-SO_3)M^2$ | 14 | 781 | 99 |
| $H-(CF_2)_{15}-SO_3)M^2$ | 15 | 831 | 99 |
| $H-(CF_2)_{16}-SO_3)M^2$ | 16 | 881 | 99 |
| $H-(CF_2)_{17}-SO_3)M^2$ | 17 | 931 | 99 |
| $H-(CF_2)_{18}-SO_3)M^2$ | 18 | 981 | 99 |
| $H-(CF_2)_{19}-SO_3)M^2$ | 19 | 1031 | 99 |
| $H-(CF_2)_{20}-SO_3)M^2$ | 20 | 1081 | 99 |

The content of the compound represented by the general formula (2) having n carbon atoms in the extract was calculated by the following formula (3). The values a and b in the formula (3) were determined by the formula (1):

$$XSn=((ASn-b)/a)\times((50\times n+81)/499) \quad (3)$$

XSn: content (ng/mL) of compound represented by general formula (2) having n carbon atoms in extract solution ASn: peak area of compound represented by general formula (2) having n carbon atoms in extract solution The quantification limit in this measurement is 1 ng/mL.

Content of Compound Represented by General Formula (2) Having n Carbon Atoms Contained in Aqueous Dispersion The content of the compound represented by the general formula (2) having n carbon atoms contained in the aqueous dispersion was determined by the following formula (5):

$$ZSn=XSn\times86.3 \quad (5)$$

ZSn: content (ppb based on PTFE) of compound represented by general formula (2) having n carbon atoms contained in aqueous dispersion Content of Compound Represented by General Formula (2) Having n Carbon Atoms Contained in Powder The content of the compound represented by the general formula (2) having n carbon atoms contained in the powder was determined by the following formula (4):

$$YSn=XSn\times12.6 \quad (4)$$

YSn: content (ppb based on PTFE) of compound represented by general formula (2) having n carbon atoms contained in powder Synthesis Example 1

To 1.0 M KOH water, 10-oxoundecanoic acid (1.8 g) was added, and the water was distilled off, whereby potassium 10-oxoundecanoate (2.2 g) was obtained. The spectrum data of the resulting potassium 10-oxoundecanoate (hereinafter referred to as surfactant B) is shown below.

$^1$H-NMR (CDCl$_3$) δ ppm: 1.04 (m, 8H), 1.30-1.32 (m, 4H), 1.89-2.01 (m, 5H), 2.27-2.33 (t, J=7.6, 4H)

Synthesis Example 2

To a glass autoclave having an internal volume of 1 L, 550 g of deionized degassed water, 30 g of paraffin wax, and 0.0145 g of the surfactant B were added. The reactor was sealed and the system was purged with nitrogen, so that oxygen was removed. The reactor was heated up to 70° C. and TFE was filled into the reactor such that the reactor was adjusted to 0.78 MPa. Then, 0.110 g of ammonium persulfate (APS) serving as polymerization initiator was charged thereinto. TFE was charged so as to keep the reaction pressure constant at 0.78 MPa. When 50 g of TFE was charged, the stirring was stopped and the pressure was released until the reactor was adjusted to the atmospheric pressure. The aqueous dispersion was collected from the reactor and cooled so that the paraffin wax was separated, whereby a PTFE aqueous dispersion B was obtained. The particles contained in the resulting PTFE aqueous dispersion B had an average primary particle size of 216 nm. Further, the solid content in the resulting PTFE aqueous dispersion B was 8.2% by mass.

The content of the compounds represented by the general formulas (1) and (2) of the resulting PTFE aqueous dispersion B was measured. The results are shown in Table 7 below.

Preparation Example 1

Deionized water was added to the PTFE aqueous dispersion B obtained in Synthesis Example 2 to adjust the specific gravity (25° C.) to 1.080. To a glass coagulation tank having an internal volume of 6 L equipped with an anchor type stirring blade and a baffle plate, 2.5 L of a PTFE aqueous dispersion having a specific gravity adjusted was added, and the temperature was adjusted so that the internal temperature became 34° C. Immediately after the adjustment, 16 g of nitric acid (10%) was added, and at the same time, stirring was started at a stirring speed of 500 rpm. After the start of stirring, it was confirmed that the aqueous dispersion was in a slurry state to form a wet PTFE powder, and stirring was further continued for another 1 minute.

Subsequently, the wet PTFE powder was filtered off, the wet PTFE powder and 2.5 L of deionized water were charged into a coagulation tank, the temperature was adjusted to 25° C., and the polymer powder was washed at a stirring speed of 500 rpm 2 times. After washing, the wet PTFE powder was filtered off and allowed to stand in a hot air circulation type dryer at 150° C. for 18 hours to dry to obtain a PTFE powder.

The resulting PTFE powder had an SSG of 2.261. This demonstrates that the resulting PTFE was a high-molecular-weight PTFE.

The content of the compounds represented by the general formulas (1) and (2) of the resulting PTFE powder was measured. The results are shown in Table 7 below.

The peaks at n of 5, 7, 9, 11, 13, 15, 17, and 19 and m of 4, 6, 8, 10, 12, 14, 16, and 18 were below the quantification limit.

The quantification limit was 86 ppb for the aqueous dispersion and 13 ppb for the powder.

In the present disclosure, "E" in the table represents exponential notation. For example, "8.3E+04" represents $8.3 \times 10^4$.

As shown in Table 1, it is understood that when a fluorine-containing polymer is obtained by polymerization using a hydrocarbon surfactant, the fluorine-containing compound represented by the general formula (1) is present in the aqueous dispersion of the fluorine-containing polymer. When the fluorine-containing polymer is recovered from the aqueous dispersion, discharge water containing the fluorine-containing compound represented by the general formula (1) is produced. By bringing discharge water generated in such a process for producing a fluorine-containing polymer into contact with an adsorbent, the fluorine-containing compound represented by the general formula (1) in the discharge water can be removed from the discharge water.

Hereinafter, the removal method of the present disclosure will be described with reference to an experimental example using a model aqueous solution (an aqueous solution containing a fluorine-containing compound represented by the general formula (1)).

The removal ratios of $H-(CF_2)_6-COOH$ and $H-(CF_2)_8-COOH$ by the adsorption treatment were measured under the following conditions using liquid chromatography-mass spectrometry.

TABLE 7

| | | | Synthesis Example 2 PTFE aqueous dispersion | Preparation Example 1 PTFE powder |
|---|---|---|---|---|
| Content of general formula (2) | n = 4 | ppb/PTFE | below quantification limit | below quantification limit |
| | n = 6 | ppb/PTFE | below quantification limit | below quantification limit |
| | n = 8 | ppb/PTFE | below quantification limit | below quantification limit |
| | n = 10 | ppb/PTFE | below quantification limit | below quantification limit |
| | n = 12 | ppb/PTFE | below quantification limit | below quantification limit |
| | n = 14 | ppb/PTFE | below quantification limit | below quantification limit |
| | n = 16 | ppb/PTFE | below quantification limit | below quantification limit |
| | n = 18 | ppb/PTFE | below quantification limit | below quantification limit |
| | n = 20 | ppb/PTFE | below quantification limit | below quantification limit |
| | Total | ppb/PTFE | below quantification limit | below quantification limit |
| Content of general formula (1) | m = 3 | ppb/PTFE | 8.3E+04 | below quantification limit |
| | m = 5 | ppb/PTFE | 9.3E+04 | below quantification limit |
| | m = 7 | ppb/PTFE | 6.6E+04 | below quantification limit |
| | m = 9 | ppb/PTFE | 9.0E+03 | below quantification limit |
| | m = 11 | ppb/PTFE | 4.4E+02 | below quantification limit |
| | m = 13 | ppb/PTFE | 1.1E+02 | below quantification limit |
| | m = 15 | ppb/PTFE | 8.7E+01 | 1.7E+01 |
| | m = 17 | ppb/PTFE | 1.8E+03 | 3.9E+02 |
| | m = 19 | ppb/PTFE | 1.9E+03 | 4.1E+02 |
| | Total | ppb/PTFE | 2.5E+05 | 8.2E+02 |

Measurement Equipment Configuration and LC-MS Measurement Conditions

TABLE 8

| LC unit | |
|---|---|
| Equipment | Acquity UPLC manufactured by Waters |
| Column | Acquity UPLC manufactured by Waters BEH C18 1.7 mm (2.1 × 50 mm) |
| Mobile phase | A $CH_3CN$ |
| | B 20 mM $CH_3COONH_4/H_2O$ |
| | 0→1.5 min      A:B = 10:90 |
| | 1.5→8.5 min      A:B = 10:90→A:B = 90:10 Linear gradient |
| | 8.5→10 min      A:B = 90:10 |
| Flow rate | 0.4 mL/min |
| Column temperature | 40° C. |
| Amount of sample injected | 5 μL |

| MS unit | |
|---|---|
| Equipment | TQ Detecter |
| Measurement mode | MRM (Multiple Reaction Monitoring) |
| Ionization method | Electrospray ionization negative mode |

MRM Measurement Parameters

TABLE 9

| Compound | Precursor | Product |
|---|---|---|
| H—$(CF_2)_6$—COOH | 345 | 281 |
| H—$(CF_2)_8$—COOH | 445 | 381 |

The removal ratio of H—$(CF_2)_6$—COOH $X_{C7}\%$ was calculated from the formula (6):

$$X_{C7}=(1-(A_{C7}/B_{C7}))\times 100 \quad \text{Formula (6)}$$

$A_{C7}$: peak area of H—$(CF_2)_6$—COOH contained in the sample after adsorption treatment
$B_{C7}$: peak area of H—$(CF_2)_6$—COOH contained in the sample before adsorption treatment The removal ratio of H—$(CF_2)_8$—COOH $X_{C9}\%$ was calculated from the formula (7):

$$X_{C9}=(1-(A_{C9}/B_{C9}))\times 100 \quad \text{Formula (7)}$$

$A_{C9}$: peak area of H—$(CF_2)_8$—COOH contained in the sample after adsorption treatment
$B_{C9}$: peak area of H—$(CF_2)_8$—COOH contained in the sample before adsorption treatment The detection limit is 5 or less in peak area.

The concentration of the fluorine-containing compound represented by the general formula (1) in the following experimental example was as follows. In the experimental examples, "%", "ppm" and "ppb" are based on weight unless otherwise specified.

Experimental Example A

After 5 g of an aqueous solution containing 5 ppm of $H(CF_2)_6COOH$ and 5 ppm of $H(CF_2)_8COOH$ (aqueous solution A) was diluted with 45 g of water, and then $H(CF_2)_6COOH$ and $H(CF_2)_8COOH$ (fluorine-containing compound represented by the general formula (1)) were analyzed. The results of the analysis are shown in the column before the adsorption treatment in Table 10.

Experimental Example 1

To 50 g of an aqueous solution containing 5 ppm of $H(CF_2)_6COOH$ and 5 ppm of $H(CF_2)_8COOH$ (aqueous solution A) as a model aqueous solution, 1.5 g of anion exchange resin Amberjet IRA40020H (trade name, manufactured by Organo Corporation) as an adsorbent was added and stirred using a shaking bath SB-20 (manufactured by AS ONE) at 180 rpm (revolutions per minute) for 3 hours. After the stirring was stopped, the mixture was allowed to stand for 0.5 hours, 5 g of the supernatant was collected and diluted with 45 g of water, and then $H(CF_2)_6COOH$ and $H(CF_2)_8COOH$ (fluorine-containing compound represented by the general formula (1)) were analyzed. The results are shown in Table 10.

Experimental Example 2

The same operation as in Experimental Example 1 was performed except that the amount of the adsorbent charged was changed to 6.5 g.
The results are shown in Table 10.

Experimental Example 3

The same operation as in Experimental Example 1 was performed except that the amount of the adsorbent charged was changed to 13.0 g.
The results are shown in Table 10.

Experimental Example 4

The same operation as in Experimental Example 1 was performed except that the adsorbent was changed to the anion exchange resin Purolite A300 (manufactured by Purolite Co., Ltd.). The results are shown in Table 10.

Experimental Example 5

The same operation as in Experimental Example 4 was performed except that the amount of the adsorbent charged was changed to 6.5 g.
The results are shown in Table 10.

Experimental Example 6

The same operation as in Experimental Example 4 was performed except that the amount of the adsorbent charged was changed to 13.0 g. The results are shown in Table 10.

Experimental Example 7

The same operation as in Experimental Example 1 was performed except that the adsorbent was changed to the anion exchange resin Purolite PFA694E (manufactured by Purolite Co., Ltd.). The results are shown in Table 10.

Experimental Example 8

The same operation as in Experimental Example 7 was performed except that the amount of the adsorbent charged was changed to 6.5 g.
The results are shown in Table 10.

Experimental Example 9

The same operation as in Experimental Example 7 was performed except that the amount of the adsorbent charged was changed to 13.0 g. The results are shown in Table 10.

Experimental Example 10

The same operation as in Experimental Example 1 was performed except that the adsorbent was changed to the synthetic adsorbent Amberlite XAD1180N (manufactured by Organo Corporation, pore diameter 506 Å, specific surface area 623 m$^2$/g). The results are shown in Table 10.

Experimental Example 11

The same operation as in Experimental Example 10 was performed except that the amount of the adsorbent charged was changed to 6.5 g.

The results are shown in Table 10.

Experimental Example 12

The same operation as in Experimental Example 10 was performed except that the amount of the adsorbent charged was changed to 13.0 g. The results are shown in Table 10.

Experimental Example 13

The same operation as in Experimental Example 1 was performed except that the adsorbent was changed to the synthetic adsorbent Amberlite FPX66 (manufactured by Organo Corporation, pore diameter 243 Å, specific surface area 914 m$^2$/g). The results are shown in Table 10.

Experimental Example 14

The same operation as in Experimental Example 13 was performed except that the amount of the adsorbent charged was changed to 6.5 g.
The results are shown in Table 10.

Experimental Example 15

The same operation as in Experimental Example 13 was performed except that the amount of the adsorbent charged was changed to 13.0 g. The results are shown in Table 10.

TABLE 10

| | | | Experimental Example 1 | Experimental Example 2 | Experimental Example 3 | Experimental Example 4 | Experimental Example 5 | Experimental Example 6 | Experimental Example 7 | Experimental Example 8 | Experimental Example 9 |
|---|---|---|---|---|---|---|---|---|---|---|---|
| Adsorbent | | | | Amberjet IRA40020H | | | Purolite A300 | | | Purolite PFA694E | |
| Pore diameter | | Å | — | | | — | | | — | | |
| Specific surface area | | m$^2$/g | — | | | — | | | — | | |
| Amount of adsorbent | | g | 1.5 | 6.5 | 13.0 | 1.5 | 6.5 | 13.0 | 1.5 | 6.5 | 13.0 |
| Amount of adsorbent based on 1000 g of aqueous solution A | | g | 30 | 130 | 260 | 30 | 130 | 260 | 30 | 130 | 260 |
| H(CF2)$_6$COOH contained in aqueous solution A | before adsorption treatment | peak area | | 1.5E+04 | | | 1.5E+04 | | | 1.5E+04 | |
| | after adsorption treatment | peak area | 7.3E+01 | below detection limit | below detection limit | 2.9E+01 | 1.0E+01 | below detection limit | 4.0E+01 | 1.2E+01 | below detection limit |
| | removal rate by adsorbent treatment | % | 100 | 100 | 100 | 100 | 100 | 100 | 100 | 100 | 100 |
| H(CF2)$_8$COOH contained in aqueous solution A | before adsorption treatment | peak area | | 1.2E+04 | | | 1.2E+04 | | | 1.2E+04 | |
| | after adsoiption treatment | peak area | 1.0E+01 | 6.0E+00 | below detection limit | 3.6E+01 | 1.0E+01 | below detection limit | 2.2E+01 | 6.0E+00 | below detection limit |
| | removal rate by adsorbent treatment | % | 100 | 100 | 100 | 100 | 100 | 100 | 100 | 100 | 100 |

TABLE 10-continued

|  |  |  | Experimental Example 10 | Experimental Example 11 | Experimental Example 12 | Experimental Example 13 | Experimental Example 14 | Experimental Example 15 |
|---|---|---|---|---|---|---|---|---|
| Adsorbent |  |  | Amberlite XAD1180N | | | Amberlite FPX66 | | |
| Pore diameter |  | Å | 506 | | | 243 | | |
| Specific surface area |  | m²/g | 623 | | | 914 | | |
| Amount of adsorbent |  | g | 1.5 | 6.5 | 13.0 | 1.5 | 6.5 | 13.0 |
| Amount of adsorbent based on 1000 g of aqueous solution A |  | g | 30 | 130 | 260 | 30 | 130 | 260 |
| H(CF2)$_6$COOH contained in aqueous solution A | before adsorption treatment | peak area |  | 1.5E+04 |  |  | 1.5E+04 |  |
|  | after adsorption treatment | peak area | 9.8E+02 | 9.3E+01 | 1.9E+01 | 1.1E+03 | 1.3E+02 | 1.5E+01 |
|  | removal rate by adsorbent treatment | % | 93 | 99 | 100 | 93 | 99 | 100 |
| H(CF2)$_8$COOH contained in aqueous solution A | before adsorption treatment | peak area |  | 1.2E+04 |  |  | 1.2E+04 |  |
|  | after adsoiption treatment | peak area | 1.3E+02 | 2.8E+01 | 1.0E+01 | 1.3E+02 | 2.2E+01 | 1.6E+01 |
|  | removal rate by adsorbent treatment | % | 99 | 100 | 100 | 99 | 100 | 100 |

Experimental Example 16

As a model aqueous solution, 5 g of an aqueous solution containing 5 ppm of H(CF$_2$)$_6$COOH and 5 ppm of H(CF$_2$)$_8$COOH was diluted with 45 g of water to prepare a 50 g aqueous solution (aqueous Solution B). The aqueous solution B was mixed with 1 g of an aqueous solution containing 2,500 ppm of ammonium persulfate, heated in a constant temperature vessel at 80° C. for 7 hours, cooled to room temperature, and the concentrations of H(CF$_2$)$_6$COOH and H(CF$_2$)$_8$COOH were analyzed. The results are shown in Table 11.

TABLE 11

|  |  |  | Experimental Example 16 |
|---|---|---|---|
| H(CF$_2$)$_6$COOH contained in aqueous solution B | before APS heat treatment | peak area | 1.5 × 10$^4$ |
|  | after APS heat treatment | peak area | below detection limit |
|  | removal rate by APS heat treatment | % | 100 |
| H(CF$_2$)$_8$COOH contained in aqueous solution B | before APS heat treatment | peak area | 1.2 × 10$^4$ |
|  | after APS heat treatment | peak area | below detection limit |
|  | removal rate by APS heat treatment | % | 100 |

From the results shown in Table 11, it is presumed that the fluorine-containing compound contained in the model aqueous solution was changed to a fluorine-containing compound having a reduced number of carbon atoms or the like by treating the model aqueous solution with persulfate ion.

The invention claimed is:

1. A method for removing a fluorine-containing compound from discharge water, comprising:
bringing discharge water containing two or more fluorine-containing compounds represented by the following general formula (1) or (2) into contact with an adsorbent to allow the adsorbent to adsorb the two or more fluorine-containing compounds, wherein the discharge water is obtained in a process for producing a fluorine-containing polymer using a hydrocarbon surfactant:

$$(H-(CF_2)_m-COO)_pM^1 \qquad \text{General Formula (1):}$$

wherein m is 3 to 19, $M^1$ is H, a metal atom, $NR^b_4$, where $R^b$'s are the same or different and are each independently H or an organic group having 1 to 10 carbon atoms, imidazolium optionally having a substituent, pyridinium optionally having a substituent, or phosphonium optionally having a substituent; and p is 1 or 2, $$(H-(CF_2)_n-SO_3)_qM^2 \qquad \text{General Formula (2):}$$

wherein n is 4 to 20; $M^2$ is H, a metal atom, $NR^b_4$, where $R^b$'s are the same or different and are each independently H or an organic group having 1 to 10 carbon atoms, imidazolium optionally having a substituent, pyridinium optionally having a substituent, or phosphonium optionally having a substituent; and q is 1 or 2.

2. The method for removing a fluorine-containing compound from discharge water according to claim 1, wherein the discharge water further includes a hydrocarbon surfactant.

3. The method for removing a fluorine-containing compound from discharge water according to claim 1, wherein the hydrocarbon surfactant is a carboxylic acid hydrocarbon surfactant.

4. The method for removing a fluorine-containing compound from discharge water according to claim 1, wherein the adsorbent is at least one selected from the group consisting of an ion exchange resin, activated carbon, a synthetic adsorbent, silica gel, clay, and zeolite.

5. The method for removing a fluorine-containing compound from discharge water according to claim 1, wherein the adsorbent is an ion exchange resin or a synthetic adsorbent and has a pore diameter of 1 to 5,000 Å.

6. The method for removing a fluorine-containing compound from discharge water according to claim 1, wherein the adsorbent is activated carbon and has a specific surface area of 500 m$^2$/g or more.

7. The method for removing a fluorine-containing compound from discharge water according to claim 1, wherein a temperature in the adsorption is 0 to 50° C.

8. The method for removing a fluorine-containing compound from discharge water according to claim 1, wherein a removal ratio of the fluorine-containing compound in the adsorption is 40% or more.

9. The method for removing a fluorine-containing compound from discharge water according to claim 1, further comprising a pretreatment for removing a solid component from the discharge water before the adsorption.

10. The method for removing a fluorine-containing compound from discharge water according to claim 1, wherein the two or more fluorine-containing compounds include at least a fluorine-containing compound having m of 7 or more in the general formula (1) or a fluorine-containing compound having n of 8 or more in the general formula (2).

* * * * *